US012655120B2

(12) United States Patent
Bucknell et al.

(10) Patent No.: US 12,655,120 B2
(45) Date of Patent: Jun. 16, 2026

(54) GPR52 MODULATOR COMPOUNDS

(71) Applicant: NXERA PHARMA UK LIMITED, Cambridge (GB)

(72) Inventors: Sarah Joanne Bucknell, Cambridge (GB); Stephen Paul Watson, Cambridge (GB); Michael Alistair O'Brien, Cambridge (GB)

(73) Assignee: NXERA PHARMA UK LIMITED, Cambridge (GB)

( * ) Notice: Subject to any disclaimer, the term of this patent is extended or adjusted under 35 U.S.C. 154(b) by 817 days.

(21) Appl. No.: 17/909,792

(22) PCT Filed: Mar. 15, 2021

(86) PCT No.: PCT/GB2021/050638

§ 371 (c)(1),
(2) Date: Sep. 7, 2022

(87) PCT Pub. No.: WO2021/181122

PCT Pub. Date: Sep. 16, 2021

(65) Prior Publication Data

US 2024/0254101 A1 Aug. 1, 2024

(30) Foreign Application Priority Data

Mar. 13, 2020 (GB) .................................... 2003668

(51) Int. Cl.

| | |
|---|---|
| ***C07D 401/04*** | (2006.01) |
| ***A61K 31/4439*** | (2006.01) |
| ***C07D 401/14*** | (2006.01) |
| ***C07D 405/14*** | (2006.01) |

(52) U.S. Cl.

CPC ........ *C07D 401/04* (2013.01); *A61K 31/4439* (2013.01); *C07D 401/14* (2013.01); *C07D 405/14* (2013.01)

(58) Field of Classification Search

CPC .. C07D 401/04; C07D 401/14; C07D 405/14; A61K 31/4439

See application file for complete search history.

(56) References Cited

U.S. PATENT DOCUMENTS

| | | | |
|---|---|---|---|
| 2001/0044445 | A1 | 11/2001 | Bamaung et al. |
| 2004/0220170 | A1 | 11/2004 | Atkinson et al. |

FOREIGN PATENT DOCUMENTS

| | | | | |
|---|---|---|---|---|
| EP | 1 355 889 | B1 | 6/2006 | |
| EP | 2 518 054 | A1 | 10/2012 | |
| KR | 10-2010-0097077 | A | 9/2010 | |
| RU | 2 274 639 | C2 | 4/2006 | |
| RU | 2 688 938 | C2 | 5/2019 | |
| WO | WO 99/51580 | A1 | 10/1999 | |
| WO | WO 2005/037797 | A1 | 4/2005 | |
| WO | WO 2011/078360 | A1 | 6/2011 | |
| WO | WO 2015/049574 | A1 | 4/2015 | |
| WO | WO 2016/176571 | A1 | 11/2016 | |
| WO | WO 2017/077280 | A1 | 5/2017 | |
| WO | WO 2018/098561 | A1 | 6/2018 | |
| WO | WO-2019053090 | A1 * | 3/2019 | ........... C07D 417/10 |
| WO | WO 2019/079485 | A1 | 4/2019 | |
| WO | WO 2019/079596 | A1 | 4/2019 | |
| WO | WO 2019/079607 | A1 | 4/2019 | |
| WO | WO 2021/090030 | A1 | 5/2021 | |
| WO | WO 2021/181122 | A1 | 9/2021 | |
| WO | WO 2022/043714 | A1 | 3/2022 | |

OTHER PUBLICATIONS

Thornber, Chemical Society Reviews, 4, 1979 (Year: 1979).*
Ali, Drug Discovery Today, vol. 29, No. 4, Apr. 2024 (Year: 2024).*
Rautio, Nature Reviews Drug Discovery, vol. 7, Mar. 2008 (Year: 2008).*
International Search Report for International Application No. PCT/GB2021/050638, dated Apr. 26, 2021.
Tokumaru et al., "Design, synthesis, and pharmacological evaluation of 4-azolyl-benzamide derivatives as novel GPR52 agonists," Bioorganic & Medicinal Chemistry, vol. 25, 2017 (Available online Apr. 1, 2017), pp. 3098-3115.
Written Opinion of the International Searching Authority for International Application No. PCT/GB2021/050638, dated Apr. 26, 2021.
Komatsu et al., "Anatomical Transcriptome of G Protein-Coupled Receptors Leads to the Identification of a Novel Therapeutic Candidate GPR52 for Psychiatric Disorders," PLOS One, vol. 9, Issue 2, Feb. 2014, e90134, pp. 1-16.
Batista et al., "Effects of aripiprazole on caffeine-induced hyperlocomotion and neural activation in the striatum," Naunyn-Schmiedeberg's Archives of Pharmacology, vol. 389, 2016, pp. 11-16.
Cunha et al., "Potential therapeutic interest of adenosine A2A receptors in psychiatric disorders," Current Pharmaceutical Design, vol. 14, No. 15, 2008, pp. 1512-1524.
Garrett et al., "D1 and D2 Dopamine Receptor Antagonists Block Caffeine-Induced Stimulation of Locomotor Activity in Rats," Pharmacology Biochemistry and Behavior, vol. 47, 1994, pp. 89-94.

(Continued)

*Primary Examiner* — Andrew D Kosar
*Assistant Examiner* — Phillip Matthew Rzeczycki
(74) *Attorney, Agent, or Firm* — Birch, Stewart, Kolasch & Birch, LLP

(57) ABSTRACT

The disclosures herein relate to novel compounds of Formula (1); and salts thereof, wherein X, Y, $R^1$, $R^2$, $R^3$ and $R^4$ are defined herein, and their use in treating, preventing, ameliorating, controlling or reducing the risk of disorders associated with GPR52 receptors.

(1)

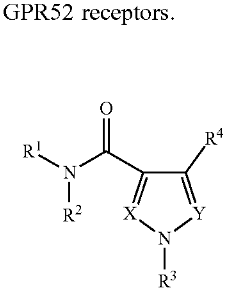

37 Claims, 1 Drawing Sheet

(56) References Cited

OTHER PUBLICATIONS

Hettinger et al., "Ultrastructural Localization of Adenosine A2A Receptors Suggests Multiple Cellular Sites for Modulation of GABAergic Neurons in Rat Striatum," Journal of Comparative Neurology, vol. 431, 2001, pp. 331-346.
Nakahata et al., "Design and synthesis of 1-(1-benzothiophen-7-yl)-1H-pyrazole, a novel series of G protein-coupled receptor 52 (GPR52) agonists," Bioorganic & Medicinal Chemistry, vol. 26, 2018, pp. 1598-1608.
Rosin et al., "Immunohistochemical Localization of Adenosine A2A Receptors in the Rat Central Nervous System," Journal of Comparative Neurology, vol. 401, 1998, pp. 163-186.
Setoh et al., "Discovery of the First Potent and Orally Available Agonist of the Orphan G-Protein-Coupled Receptor 52," Journal of Medicinal Chemistry, vol. 57, 2014, pp. 5226-5237.
Yacoubi et al., "The stimulant effects of caffeine on locomotor behaviour in mice are mediated through its blockade of adenosine A2A receptors," British Journal of Pharmacology, vol. 129, 2000, pp. 1465-1473.

* cited by examiner

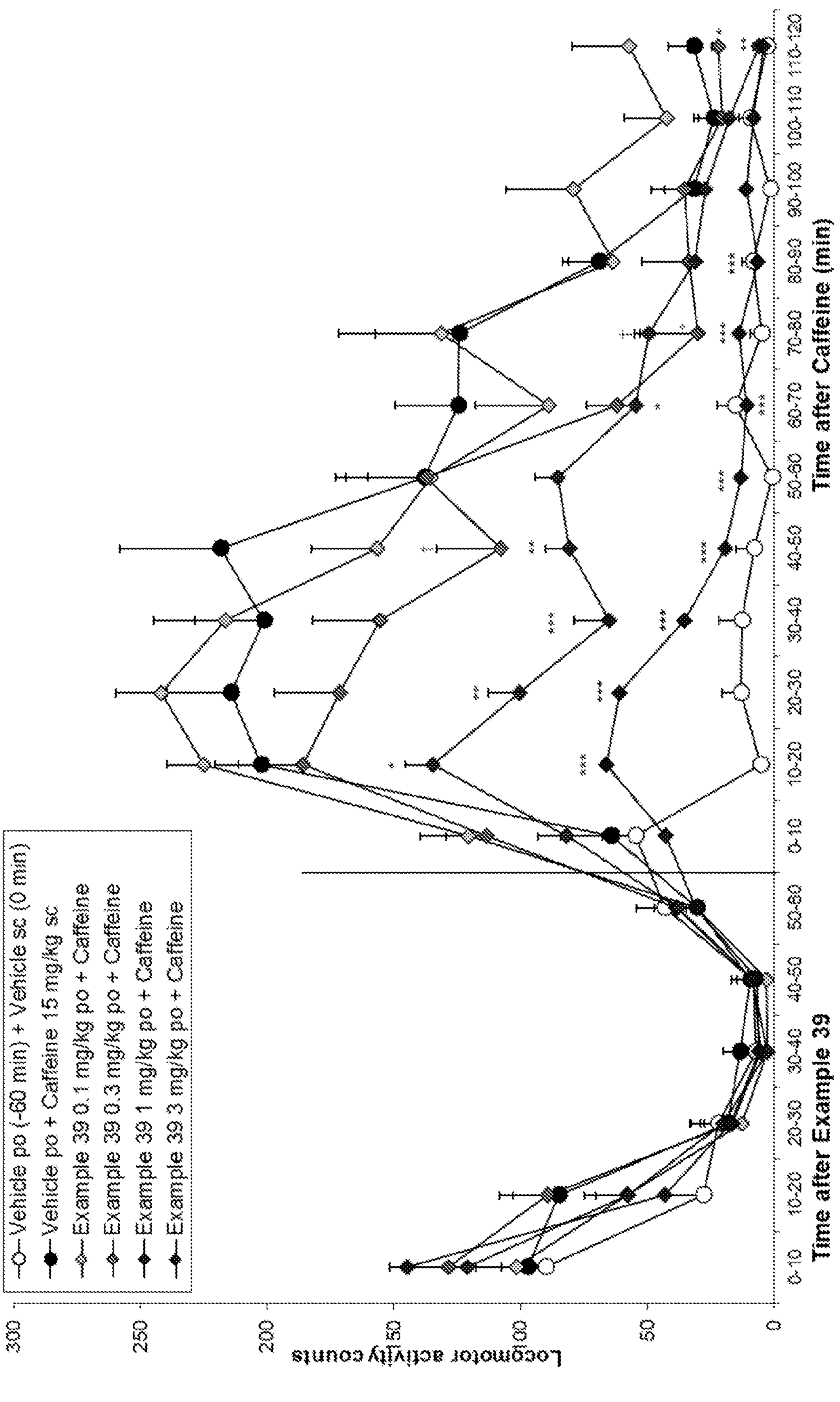
Vehicle po (-60 min) + Vehicle sc (0 min)
Vehicle po + Caffeine 15 mg/kg sc
Example 39 0.1 mg/kg po + Caffeine
Example 39 0.3 mg/kg po + Caffeine
Example 39 1 mg/kg po + Caffeine
Example 39 3 mg/kg po + Caffeine
Locomotor activity counts
300
250
200
150
100
50
0
0-10
10-20
20-30
30-40
40-50
50-60
Time after Example 39
0-10
10-20
20-30
30-40
40-50
50-60
60-70
70-80
80-90
90-100
100-110
110-120
Time after Caffeine (min)

GPR52 MODULATOR COMPOUNDS

This application relates to novel compounds and their use as G-protein coupled receptor 52 (GPR52) modulators. Compounds described herein may be useful in the treatment or prevention of diseases in which GPR52 receptors are involved or in which modulation of GPR52 receptors may be beneficial. The application is also directed to pharmaceutical compositions comprising these compounds and the manufacture and use of these compounds and compositions in the prevention or treatment of diseases in which GPR52 receptors are involved or in which modulation of GPR52 receptors may be beneficial.

BACKGROUND OF THE INVENTION

G-protein coupled receptor 52 (GPR52) is a constitutively active Gs coupled orphan receptor which is highly expressed in the striatum and cortex. In the striatum GPR52 is expressed exclusively on dopamine D2 medium spiny neurons and in the cortex it is found on cortical pyramidal neurons expressing dopamine D1 receptors (Komatsu et al, 2014, PLoS One 9: e90134). Based on its localization and functional coupling, GPR52 is proposed to play a role in the modulation of fronto-striatal and limbic dopamine and may therefore have utility in the treatment of neuropsychiatric disorders. GPR52 agonists are thought to be particularly relevant to the treatment of schizophrenia, where they are hypothesized to improve cognition and negative symptoms indirectly by potentiating D1 signalling but alleviate positive symptoms through inhibition of D2-mediated signalling in the striatum.

GPR52 agonists could be used to treat psychiatric disorders related to dysfunction of the mesolimbic and mesocortical pathways. Examples include treatment of the positive, negative and cognitive symptoms of schizophrenia, depression, attention-deficit hyperactivity disorder, anxiety disorders (generalised anxiety disorder, obsessive compulsive disorder, panic disorder), bipolar disorder, addiction/impulse-control disorders and autism spectrum disorders. Neuropsychiatric symptoms (e.g. psychosis, anhedonia, agitation, etc) of neurodegenerative diseases (e.g. Alzheimer's disease, Parkinson's disease, Huntington's disease, etc) could also be treated by GPR52 agonists. GPR52 expression in the pituitary gland and hypothalamus suggests utility for GPR52 modulators in pituitary and hypothalamic disorders, and there is preclinical evidence (Xiong et al, 2016, WO2016/176571) to suggest that GPR52 agonists could be useful in the treatment of hyperprolactinemia.

WO2019/053090 discloses diphenyl compounds as growth factor pathway activators.

The Invention

The present invention provides compounds having activity as G protein-coupled receptor 52 (GPR52) modulators.

Accordingly, the invention provides a compound of Formula (1):

(1)

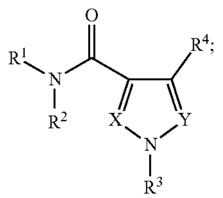

or a salt thereof, wherein;

X is N or $CR^5$;

Y is N or $CR^6$—

$R^1$ is H, $C_{1-6}$ alkyl optionally substituted with OH or 1 to 6 fluorine atoms, $C_{3-6}$ cycloalkyl optionally substituted with OH or 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by an O atom which is not directly attached to the N or attached to a carbon atom which is directly attached to the N; or $R^1$ is joined to $R^2$ to form a 4, 5, 6 or 7-membered ring which is optionally substituted with OH or 1 to 6 fluorine atoms;

$R^2$ is H or $C_{1-3}$ alkyl optionally substituted with OH or 1 to 6 fluorine atoms; or $R^2$ is joined to $R^1$ to form a 4, 5, 6 or 7-membered ring which is optionally substituted with OH or 1 to 6 fluorine atoms;

$R^4$, $R^5$ and $R^6$ are independently selected from H, CN, halo, $C_{1-6}$ alkyl optionally substituted with OH or 1 to 6 fluorine atoms, $C_{3-6}$ cycloalkyl optionally substituted with OH or 1 to 6 fluorine atoms and $C_{1-6}$ alkoxy optionally substituted with 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by O;

$R^3$ is a group of the formula:

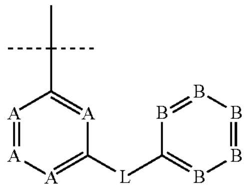

wherein, each A is independently N or $CR^7$;

L is $CH_2$ or CHOH;

each B is independently N, $CR^B$, $CR^9$ or $CR^{10}$;

$R^7$ is selected from H, halo, CN and $C_{1-3}$ alkyl optionally substituted with 1 to 6 fluorine atoms;

$R^8$, $R^9$ and $R^{10}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein one atom of the $C_{1-6}$ alkyl group may be optionally replaced by a heteroatom selected from O, N, S and oxidised forms thereof.

Compounds of the present invention may be used as GPR52 modulators. Compounds of the present invention may be used as GPR52 agonists. Compounds of the present invention may be used in the manufacture of medicaments. The compounds or medicaments may be for use in treating, preventing, ameliorating, controlling or reducing the risk of diseases or disorders in which GPR52 receptors are involved. The compounds or medicaments may be for use in treating, preventing, ameliorating, controlling or reducing the risk of diseases or disorders in which modulation of GPR52 receptors may be beneficial. Compounds of the present invention may be useful in the treatment of psychiatric disorders; neuropsychiatric disorders; neurodegenerative disorders; psychotic disorders; cognitive disorders; neurocognitive disorders; extrapyramidal disorders; movement disorders; motor disorders; hyperkinetic movement disorders; catatonia; mood disorders; depressive disorders; anxiety disorders; obsessive-compulsive disorder (OCD); autism spectrum disorders; depressive disorders; hypothalamic disorders; pituitary disorders; prolactin-related disorders; trauma- or stressor-related disorders; disruptive, impulse-control or conduct disorders; sleep-wake disorders; substance-related disorders; addictive disorders; behavioral disorders; hypofrontality; abnormalities in the tuberoinfundibular, mesolimbic, mesocortical, or nigrostriatal pathway; decreased activity in the striatum; cortical dysfunction; neurocognitive dysfunction or conditions or symptoms related thereto.

Compounds of the present invention may be useful in the treatment of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, anhedonia, agitation, Alzheimer's disease, Parkinson's disease, Huntington's disease, vascular dementia, Lewy body disease, frontotemporal dementia, Tourette's syndrome, hyperprolactinemia, pituitary adenoma, prolactinoma, craniopharyngioma, Cushing's disease, diabetes insipidus, non-functioning tumours, obesity, posttraumatic stress disorder (PTSD), akathisia and associated movements, athetosis, ataxia, ballismus, hemiballismus, chorea, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, tremor, Wilson's disease, schizotypal personality disorder, delusional disorder, brief psychotic disorder, schizophreniform disorder, schizoaffective disorder, substance- or medication-induced psychotic disorder, delusions, hallucinations, disorganized thinking, grossly disorganized or abnormal motor behavior, catatonia, major depressive disorder, bipolar I disorder, bipolar II disorder, cyclothymic disorder, substance- or medication-induced bipolar and related disorders, bipolar and related disorders due to another medical condition, separation anxiety disorder, selective mutism, specific phobia, social anxiety disorder, panic disorder, agoraphobia, generalized anxiety disorder, substance- or medication-induced anxiety disorder, anxiety disorders due to another medical condition, delirium, major neurocognitive disorder, minor neurocognitive disorder, amnesia, dementia, developmental coordination disorder, stereotypic movement disorder, a post-stroke effect, dentatorubral-pallidoluysian atrophy, diminished emotional expression, avolition, alogia and asociality.

DETAILED DESCRIPTION OF THE INVENTION

The invention relates to novel compounds. The invention also relates to the use of novel compounds as modulators of the GPR52 receptor. The invention further relates to the use of novel compounds in the manufacture of medicaments for use as GPR52 modulators. Compounds of the present invention may be used as GPR52 agonists. The compounds or medicaments may be for use in treating, preventing, ameliorating, controlling or reducing the risk of diseases or disorders in which GPR52 receptors are involved. The compounds or medicaments may be for use in treating, preventing, ameliorating, controlling or reducing the risk of diseases or disorders in which modulation of GPR52 receptors may be beneficial.

The invention further relates to compounds, compositions and medicaments that may be useful in the treatment of psychiatric disorders; neuropsychiatric disorders; neurodegenerative disorders; psychotic disorders; cognitive disorders; neurocognitive disorders; extrapyramidal disorders; movement disorders; motor disorders; hyperkinetic movement disorders; catatonia; mood disorders; depressive disorders; anxiety disorders; obsessive-compulsive disorder (OCD); autism spectrum disorders; depressive disorders; prolactin-related disorders; trauma- or stressor-related disorders; disruptive, impulse-control or conduct disorders; sleep-wake disorders; substance-related disorders; addictive disorders; behavioral disorders; hypofrontality; abnormalities in the tuberoinfundibular, mesolimbic, mesocortical, or nigrostriatal pathway; decreased activity in the striatum; cortical dysfunction; neurocognitive dysfunction or conditions or symptoms related thereto.

The invention provides a compound of Formula (1):

(1)

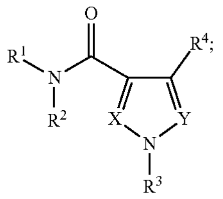

or a salt thereof, wherein;

X is N or $CR^5$;

Y is N or $CR^6$—

$R^1$ is H, $C_{1-6}$ alkyl optionally substituted with OH or 1 to 6 fluorine atoms, $C_{3-6}$ cycloalkyl optionally substituted with OH or 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by an O atom which is not directly attached to the N or attached to a carbon atom which is directly attached to the N; or $R^1$ is joined to $R^2$ to form a 4, 5, 6 or 7-membered ring which is optionally substituted with OH or 1 to 6 fluorine atoms;

$R^2$ is H or $C_{1-3}$ alkyl optionally substituted with OH or 1 to 6 fluorine atoms; or $R^2$ is joined to $R^1$ to form a 4, 5, 6 or 7-membered ring which is optionally substituted with OH or 1 to 6 fluorine atoms;

$R^4$, $R^5$ and $R^6$ are independently selected from H, CN, halo, $C_{1-6}$ alkyl optionally substituted with OH or 1 to 6 fluorine atoms, $C_{3-6}$ cycloalkyl optionally substituted with OH or 1 to 6 fluorine atoms and $C_{1-6}$ alkoxy optionally substituted with 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by O;

$R^3$ is a group of the formula:

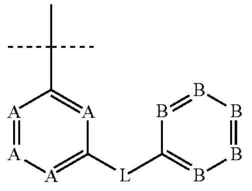

wherein, each A is independently N or $CR^7$;

L is $CH_2$ or CHOH;

each B is independently N, $CR^8$, $CR^9$ or $CR^{10}$;

$R^7$ is selected from H, halo, CN and $C_{1-3}$ alkyl optionally substituted with 1 to 6 fluorine atoms;

$R^8$, $R^9$ and $R^{10}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein one atom of the $C_{1-6}$ alkyl group may be optionally replaced by a heteroatom selected from O, N, S and oxidised forms thereof.

Also provided is a compound of Formula (1a):

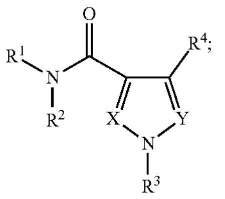

(1a)

or a salt thereof, wherein;

X is N or $CR^5$;

Y is N or $CR^6$—

$R^1$ is H, $C_{1-6}$ alkyl optionally substituted with OH or 1 to 6 fluorine atoms, $C_{3-6}$ cycloalkyl optionally substituted with OH or 1 to 6 fluorine atoms, wherein one atom of the $C_{1-6}$ alkyl or $C_{3-6}$ cycloalkyl group may be optionally replaced by O; or $R^1$ is joined to $R^2$ to form a 4, 5, 6 or 7-membered ring which is optionally substituted with OH or 1 to 6 fluorine atoms;

$R^2$ is H or $C_{1-3}$ alkyl optionally substituted with OH or 1 to 6 fluorine atoms; or $R^2$ is joined to $R^1$ to form a 4, 5, 6 or 7-membered ring which is optionally substituted with OH or 1 to 6 fluorine atoms;

$R^4$, $R^5$ and $R^6$ are independently selected from H, CN, halo, $C_{1-6}$ alkyl optionally substituted with OH or 1 to 6 fluorine atoms and $C_{1-6}$ alkoxy optionally substituted with OH or 1 to 6 fluorine atoms, wherein when the $C_{1-6}$ alkyl group is not substituted with OH, any one atom of the $C_{1-6}$ alkyl group may be optionally replaced by O;

$R^3$ is a group of the formula:

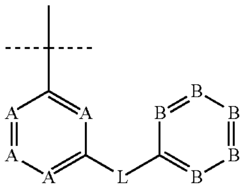

wherein, each A is independently N or $CR^7$;

L is $CH_2$ or CHOH;

each B is independently N, $CR^B$, $CR^9$ or $CR^{10}$;

$R^7$ is selected from H, halo, CN and $C_{1-3}$ alkyl optionally substituted with 1 to 6 fluorine atoms;

$R^8$, $R^9$ and $R^{10}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein one atom of the $C_{1-6}$ alkyl group may be optionally replaced by a heteroatom selected from O, N, S and oxidised forms thereof.

In the compounds herein, X can be N, CH, $CCH_3$ or $CCH_2OH$. X can be N. X can be $CR^5$. X can be CH. X can be $CCH_3$. X can be $CCH_2OH$.

In the compounds herein, Y can be N, CH, $CCH_3$ or $CCH_2OH$. Y can be N. Y can be $CR^6$. Y can be CH. Y can be $CCH_3$.

In the compounds herein, X can be N and Y can be $CR^5$. X can be N and Y can be N. X can be $CR^5$ and Y can be $CR^6$. X can be $CR^5$ and Y can be N. At least one of X and Y can be N.

The ring comprising X and Y can be selected from a pyrrole, pyrazole and a 1,2,3-triazole ring system. The ring comprising X and Y can be a pyrrole ring system. The ring comprising X and Y can be a pyrazole ring system. The ring comprising X and Y can be a 1,2,3-triazole ring system.

In the compounds herein, $R^1$ can be H, $C_{1-6}$ alkyl optionally substituted with OH or 1 to 6 fluorine atoms, $C_{3-6}$ cycloalkyl optionally substituted with OH or 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by an O atom which is not directly attached to the N or attached to a carbon atom which is directly attached to the N. $R^1$ can be H, $C_{1-6}$ alkyl optionally substituted with OH or 1 to 6 fluorine atoms, $C_{3-6}$ cycloalkyl optionally substituted with OH or 1 to 6 fluorine atoms, wherein one atom of the $C_{1-6}$ alkyl or $C_{3-6}$ cycloalkyl group may be optionally replaced by O. $R^1$ can be joined to $R^2$ to form a 4, 5, 6 or 7-membered ring which is optionally substituted with OH or 1 to 6 fluorine atoms. $R^1$ can be joined to $R^2$ to form a 4, 5, 6 or 7-membered ring. $R^1$ can be H, $C_{1-6}$ alkyl optionally substituted with OH or 1 to 6 fluorine atoms or $C_{3-6}$, cycloalkyl optionally substituted with OH or 1 to 6 fluorine atoms. $R^1$ can be H, $C_{1-6}$ alkyl or $C_{3-6}$ cycloalkyl. $R^1$ can be selected from: H, methyl, oxetanyl, $CH_2CH_2OH$ and $CH_2CH_2OCH_3$, or $R^1$ can be joined to $R^2$ to form a 5-membered ring. $R^1$ can be joined to $R^2$ to form a pyrrolidine ring. $R^1$ can be H. $R^1$ can be $C_{1-6}$ alkyl optionally substituted with OH or 1 to 6 fluorine atoms. $R^1$ can be $C_{3-6}$ cycloalkyl optionally substituted with OH or 1 to 6 fluorine atoms. $R^1$ can be $C_{1-6}$ alkyl optionally substituted with 1 to 6 fluorine atoms. $R^1$ can be $C_{3-6}$ cycloalkyl optionally substituted with 1 to 6 fluorine atoms. $R^1$ can be $C_{1-6}$ alkyl. $R^1$ can be $C_{3-6}$ cycloalkyl. $R^1$ can be methyl. $R^1$ can be oxetanyl. $R^1$ can be $CH_2CH_2OH$. $R^1$ can be $CH_2CH_2OCH_3$, In the compounds herein, $R^2$ can be H or $C_{1-3}$ alkyl optionally substituted with OH or 1 to 6 fluorine atoms. $R^2$ can be joined to $R^1$ to form a 4, 5, 6 or 7-membered ring which is optionally substituted with OH or 1 to 6 fluorine atoms. $R^2$ can be H or methyl or can be joined to $R^1$ to form a 5-membered ring. $R^2$ can be H or methyl. $R^2$ can be joined to $R^1$ to form a 5-membered ring. $R^2$ can be joined to $R^1$ to form a pyrrolidine ring. $R^2$ can be H. $R^2$ can be methyl.

In the compounds herein, $R^4$ can be selected from H, CN, halo, $C_{1-6}$ alkyl optionally substituted with OH or 1 to 6 fluorine atoms, $C_{3-6}$ cycloalkyl optionally substituted with OH or 1 to 6 fluorine atoms and $C_{1-6}$ alkoxy optionally substituted with 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by O. $R^4$ can be selected from H, CN, halo, $C_{1-6}$ alkyl optionally substituted with OH or 1 to 6 fluorine atoms and $C_{1-6}$ alkoxy optionally substituted with 1 to 6 fluorine atoms, wherein when the $C_{1-6}$ alkyl group is not substituted with OH, any one atom of the $C_{1-6}$ alkyl group may be optionally replaced by O. $R^4$ can be selected from H, CN, halo, $C_{1-6}$ alkyl optionally substituted with OH or 1 to 6 fluorine atoms and $C_{1-6}$ alkoxy optionally substituted with 1 to 6 fluorine atoms. $R^4$ can be selected from H, CN, halo, $C_{1-6}$ alkyl optionally substituted with 1 to 6 fluorine atoms and $C_{1-6}$ alkoxy optionally substituted with 1 to 6 fluorine atoms. $R^4$ can be selected from H, CN, halo, $C_{1-6}$ alkyl and $C_{1-6}$ alkoxy. $R^4$ can be selected from: H, methyl, methoxy, Cl, $CHF_2$, $CF_3$, ethyl, CN, cyclopropyl, $CH_2OH$ and $CH_2OCH_3$. $R^4$ can be H. $R^4$ can be methyl.

In the compounds herein, $R^5$ can be selected from H, CN, halo, $C_{1-6}$ alkyl optionally substituted with OH or 1 to 6 fluorine atoms, $C_{3-6}$ cycloalkyl optionally substituted with OH or 1 to 6 fluorine atoms and $C_{1-6}$ alkoxy optionally substituted with 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by O. $R^5$ can be selected from H, CN, halo, $C_{1-6}$ alkyl optionally substituted with OH or 1 to 6 fluorine atoms and $C_{1-6}$ alkoxy optionally substituted with 1 to 6 fluorine atoms, wherein when the $C_{1-6}$ alkyl group is not substituted with OH, any one atom of the $C_{1-6}$ alkyl group may be optionally replaced by O. $R^5$ can be selected from H, CN, halo, $C_{1-6}$ alkyl optionally substituted with OH or 1 to 6 fluorine atoms and $C_{1-6}$ alkoxy optionally substituted with 1 to 6 fluorine atoms. $R^5$ can be selected from H, CN, halo, $C_{1-6}$ alkyl optionally substituted with 1 to 6 fluorine atoms and $C_{1-6}$ alkoxy optionally substituted with 1 to 6 fluorine atoms. $R^5$ can be selected from H, CN, halo, $C_{1-6}$ alkyl and $C_{1-6}$ alkoxy. $R^5$ can be selected from H, methyl and $CH_2OH$. $R^5$ can be H. $R^5$ can be methyl.

In the compounds herein, $R^6$ can be selected from H, CN, halo, $C_{1-6}$ alkyl optionally substituted with OH or 1 to 6 fluorine atoms, $C_{3-6}$ cycloalkyl optionally substituted with OH or 1 to 6 fluorine atoms and $C_{1-6}$ alkoxy optionally substituted with 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by O. $R^6$ can be selected from H, CN, halo, $C_{1-6}$ alkyl optionally substituted with OH or 1 to 6 fluorine atoms and $C_{1-6}$ alkoxy optionally substituted with 1 to 6 fluorine atoms, wherein when the $C_{1-6}$ alkyl group is not substituted with OH, any one atom of the $C_{1-6}$ alkyl group may be optionally replaced by O. $R^6$ can be selected from H, CN, halo, $C_{1-6}$ alkyl optionally substituted with OH or 1 to 6 fluorine atoms and $C_{1-6}$ alkoxy optionally substituted with 1 to 6 fluorine atoms. $R^6$ can be selected from H, CN, halo, $C_{1-6}$ alkyl optionally substituted with 1 to 6 fluorine atoms and $C_{1-6}$ alkoxy optionally substituted with 1 to 6 fluorine atoms. $R^6$ can be selected from H, CN, halo, $C_{1-6}$ alkyl and $C_{1-6}$ alkoxy. $R^6$ can be selected from H, methyl and $CH_2OH$. $R^6$ can be H. $R^6$ can be methyl.

In the compounds herein, $R^3$ can be a group of the formula:

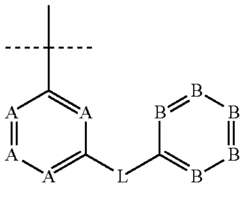

wherein, each A is independently N or $CR^7$;

L is $CH_2$ or CHOH;

each B is independently N, $CR^B$, $CR^9$ or $CR^{10}$;

$R^7$, $R^8$, $R^9$ and $R^{10}$ are independently selected from H, halo, CN and $C_{1-3}$ alkyl optionally substituted with 1 to 6 fluorine atoms.

In the compounds herein, A can be N or CH. A can be N. A can be $CR^7$. A can be CH. Each A can be CH; or one A can be N and each remaining A can be $CR^7$. Each A can be CH; or one A can be N and each remaining A can be CH.

In the compounds herein, L can be $CH_2$. L can be CHOH.

In the compounds herein, B can be N. B can be $CR^B$, $CR^9$ or $CR^{10}$. B can be CH. Each B can be $CR^B$, $CR^9$ or $CR^{10}$. Each B can be CH.

$R^7$ can be selected from H, halo, CN and $C_{1-3}$ alkyl optionally substituted with 1 to 6 fluorine atoms. $R^7$ can be selected from H, F, $CHF_2$ and $CF_3$. $R^7$ can be H.

$R^8$ can be selected from H, CN, halo, $C_{1-6}$ alkyl optionally substituted with 1 to 6 fluorine atoms and $C_{1-6}$ alkoxy optionally substituted with 1 to 6 fluorine atoms, wherein one atom of the $C_{1-6}$ alkyl group may be optionally replaced by a heteroatom selected from O, N, S and oxidised forms thereof. $R^8$ can be selected from H, halo, CN and $C_{1-3}$ alkyl optionally substituted with 1 to 6 fluorine atoms. $R^8$ can be selected from H, F, $CHF_2$ and $CF_3$. $R^8$ can be H. $R^8$ can be F. $R^8$ can be $CHF_2$. $R^8$ can be $CF_3$.

$R^9$ can be selected from H, CN, halo, $C_{1-6}$ alkyl optionally substituted with 1 to 6 fluorine atoms and $C_{1-6}$ alkoxy optionally substituted with 1 to 6 fluorine atoms, wherein one atom of the $C_{1-6}$ alkyl group may be optionally replaced by a heteroatom selected from O, N, S and oxidised forms thereof. $R^9$ can be selected from H, halo, CN and $C_{1-3}$ alkyl optionally substituted with 1 to 6 fluorine atoms. $R^9$ can be selected from H, F, $CHF_2$ and $CF_3$. $R^9$ can be H. $R^9$ can be F. $R^9$ can be $CHF_2$. $R^9$ can be $CF_3$.

$R^{10}$ can be selected from H, CN, halo, $C_{1-6}$ alkyl optionally substituted with 1 to 6 fluorine atoms and $C_{1-6}$ alkoxy optionally substituted with 1 to 6 fluorine atoms, wherein one atom of the $C_{1-6}$ alkyl group may be optionally replaced by a heteroatom selected from O, N, S and oxidised forms thereof. $R^{10}$ can be selected from H, halo, CN and $C_{1-3}$ alkyl optionally substituted with 1 to 6 fluorine atoms. $R^{10}$ can be selected from H, F, $CHF_2$ and $CF_3$. $R^{10}$ can be H. $R^{10}$ can be F. $R^{10}$ can be $CHF_2$. $R^{10}$ can be $CF_3$.

$R^B$, $R^9$ and $R^{10}$ can be independently selected from H, F, $CHF_2$ and $CF_3$.

$R^3$ can be:

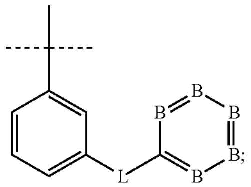
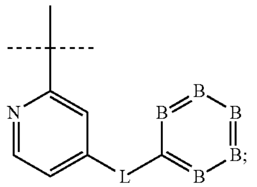
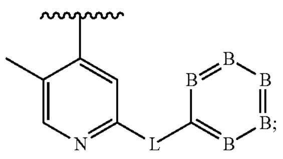
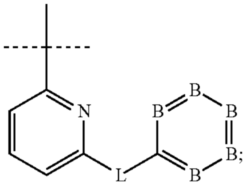
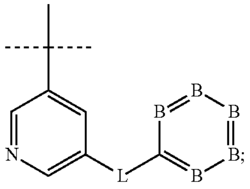
or
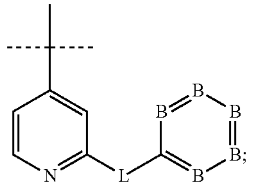

wherein L and B are as defined above.

In the compounds herein, the group:

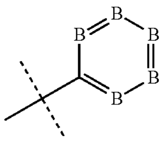

can be:

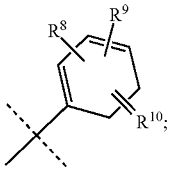

wherein $R^8$, $R^9$ and $R^{10}$ are as defined above.

In the compounds herein, the group:

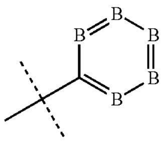

can be:

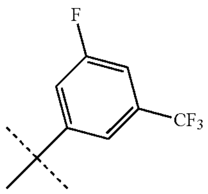

or

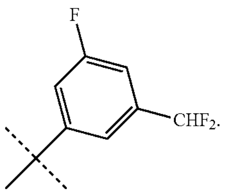

The compound may be a compound of formula (2a):

(2a)

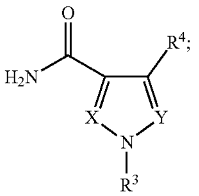

or a salt thereof, wherein X, Y, $R^3$ and $R^4$ are as defined above.

The compound may be a compound of formula (3a), (3b), (3c) or (3d):

(3a)

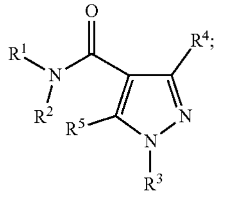

(3b)

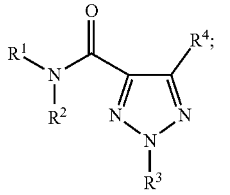

(3c)

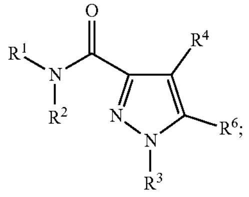

(3d)

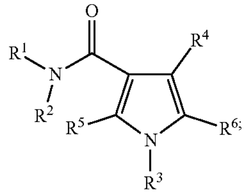

or a salt thereof, wherein $R^1$, $R^2$, $R^3$, $R^4$, $R^5$ and $R^6$ are as defined above.

The compound may be a compound of formula (4a), (4b), (4c), (4d), (4e) or (4f):

(4a)

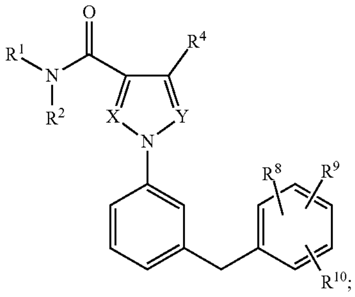

(4b)

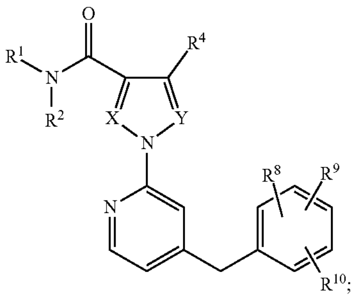

-continued
(4c)
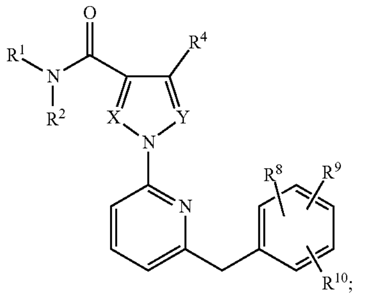
(4d)
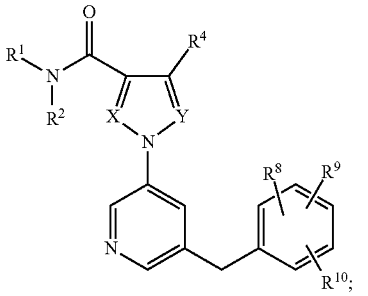
(4e)
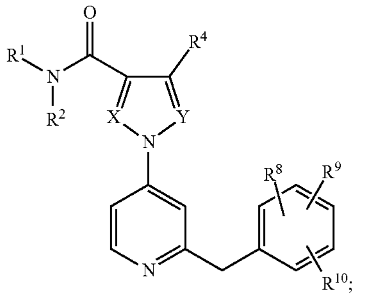
(4f)
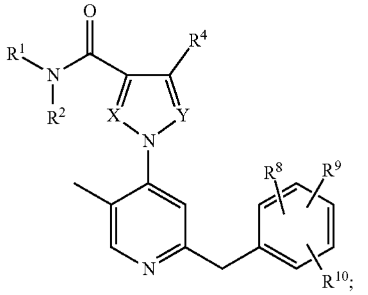
or a salt thereof, wherein X, Y, $R^1$, $R^2$, $R^4$, $R^8$, $R^9$ and $R^{10}$ are as defined above.
The compound may be a compound of formula (5a), (5b), (5c) or (5d):
(5a)
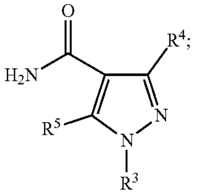
-continued
(5b)
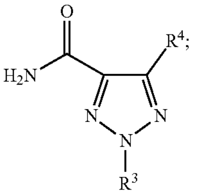
(5c)
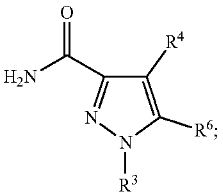
(5d)
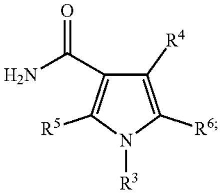
or a salt thereof, wherein $R^3$, $R^4$, $R^5$ and $R^6$ are as defined above.
The compound may be a compound of formula (6a), (6b), (6c), (6d), (6e) or (6f):
(6a)
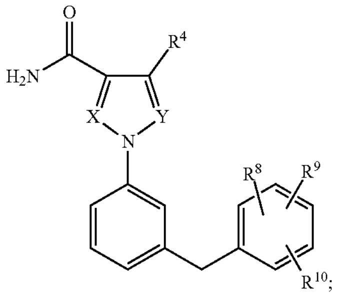
(6b)
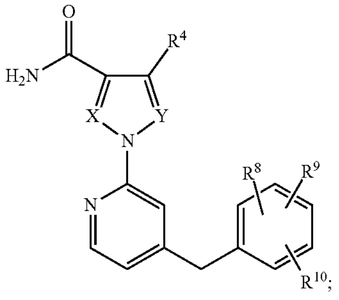

-continued
(6c)
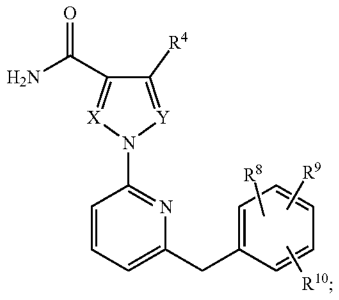
(6d)
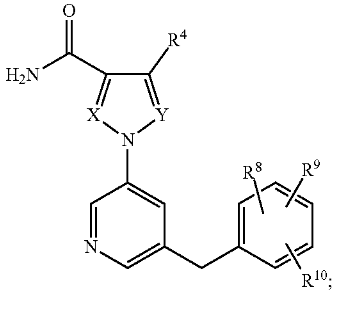
(6e)
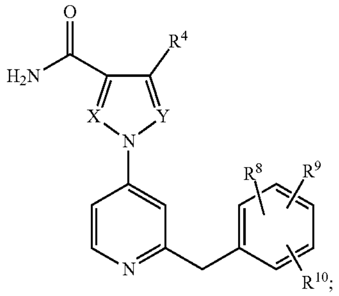
(6f)
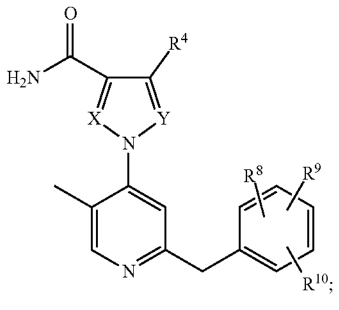
or a salt thereof, wherein X, Y, $R^4$, $R^8$, $R^9$ and $R^{10}$ are as defined above.
The compound may be a compound of formula (7a), (7b), (7c), (7d), (7e) or (7f):
(7a)
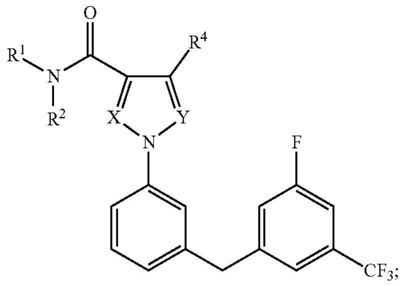
(7b)
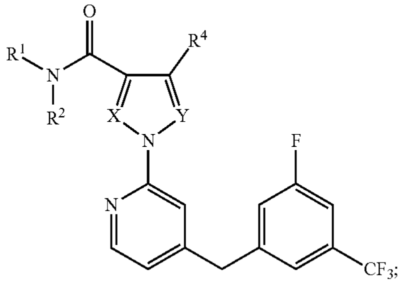
(7c)
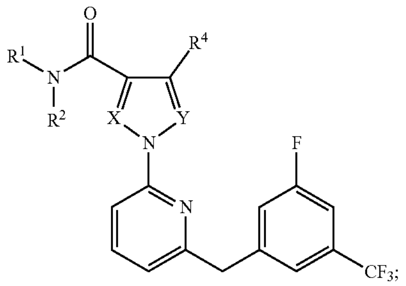
(7d)
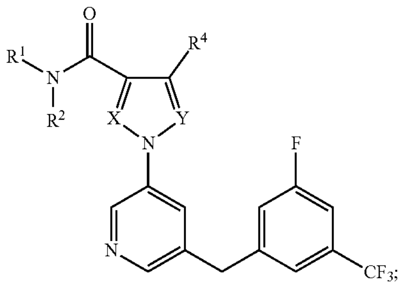
(7e)
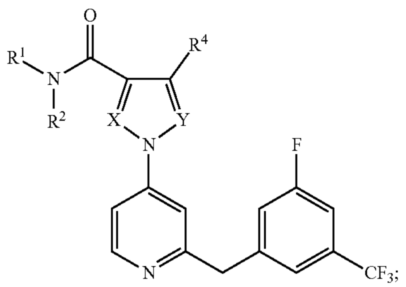

-continued
(7f)
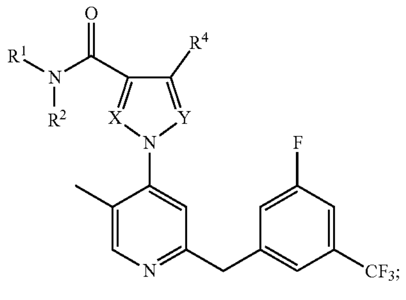
or a salt thereof, wherein X, Y, $R^1$, $R^2$ and $R^4$ are as defined above.
The compound can be selected from the group consisting of:
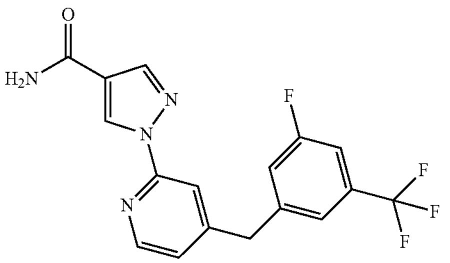
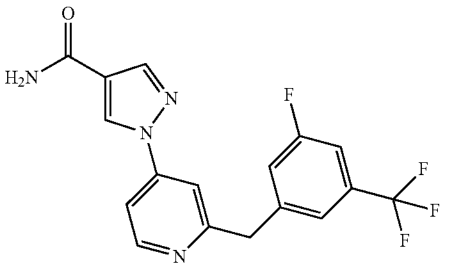
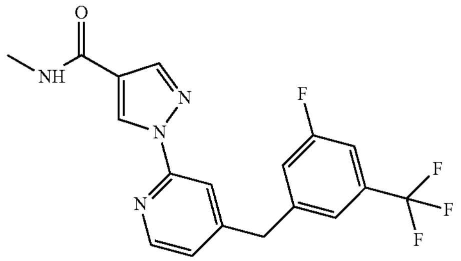
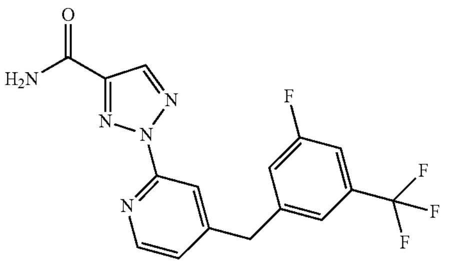
-continued
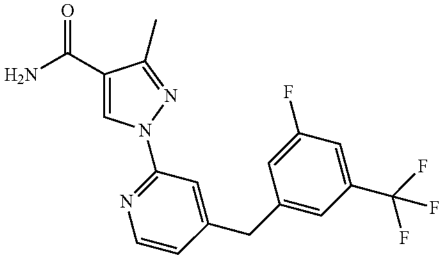
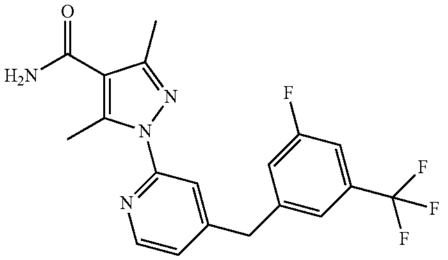
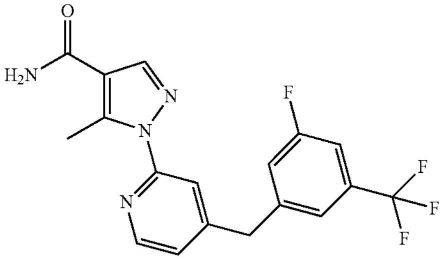
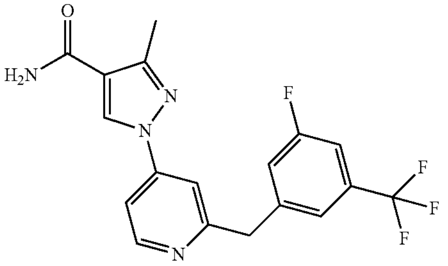
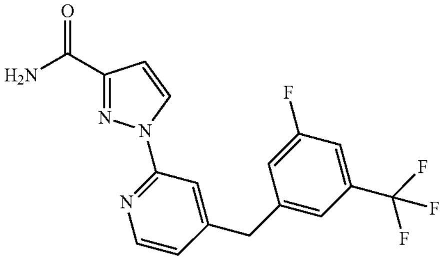
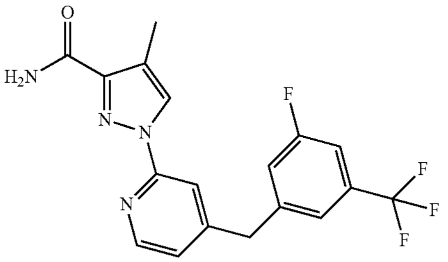

-continued
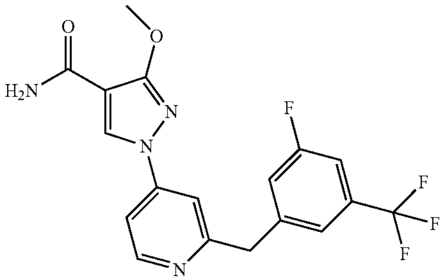
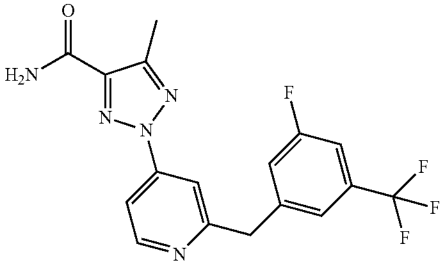
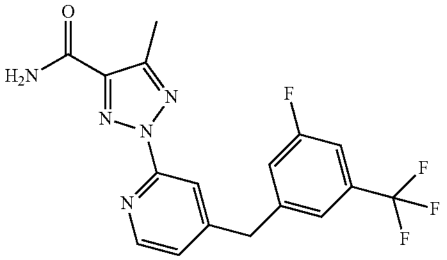
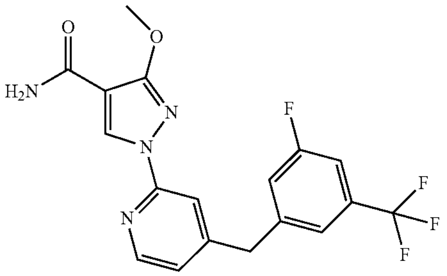
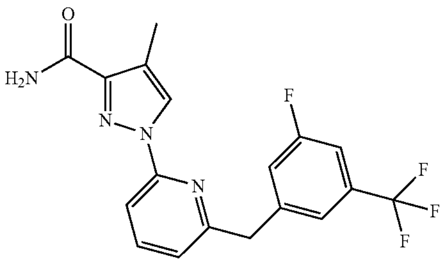
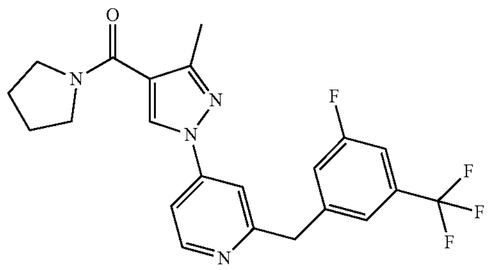
-continued
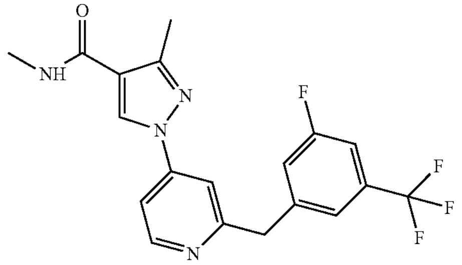
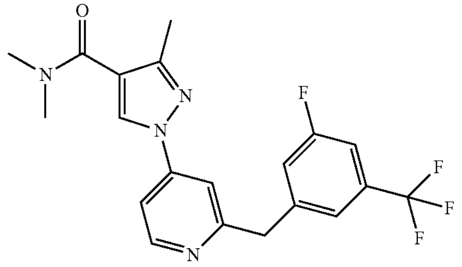
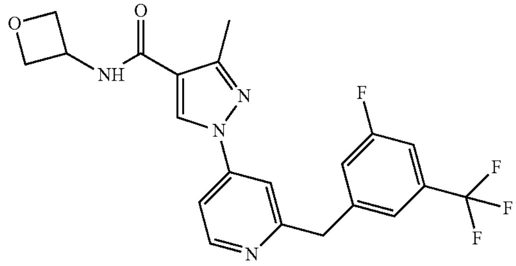
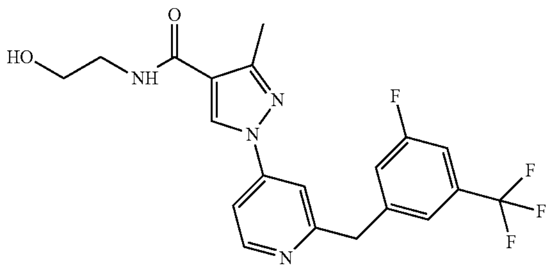
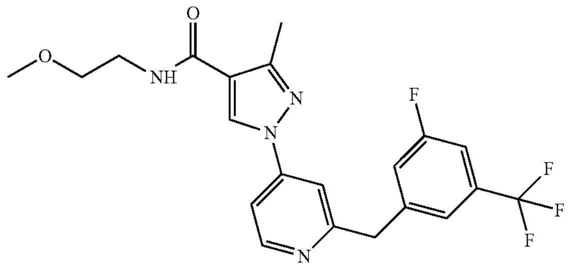
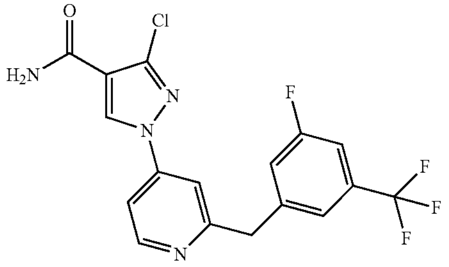

-continued
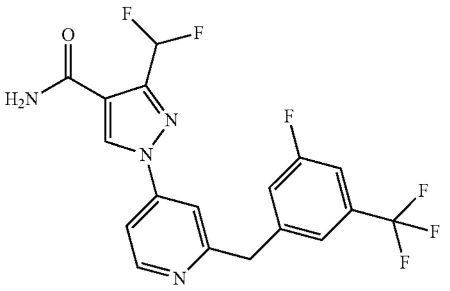
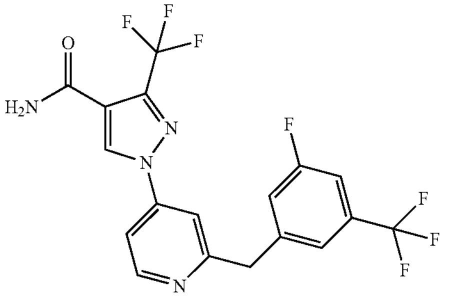
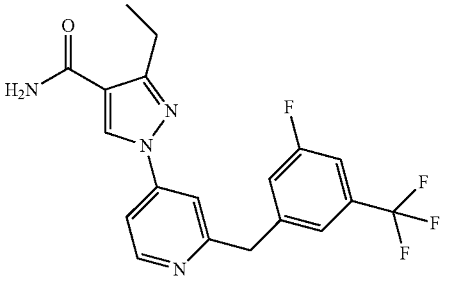
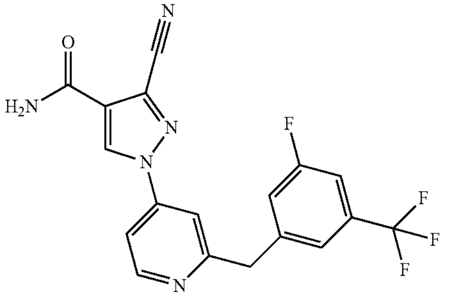
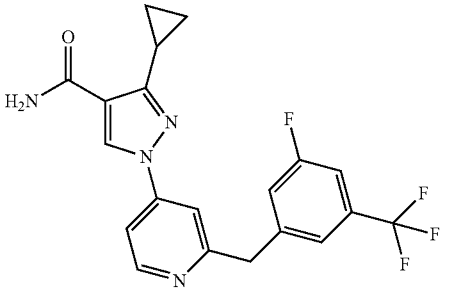
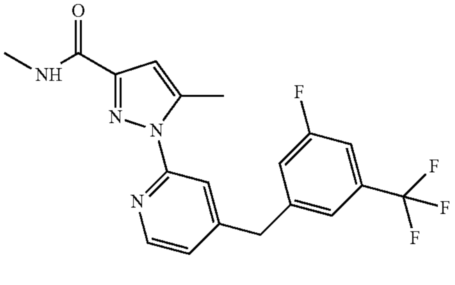
-continued
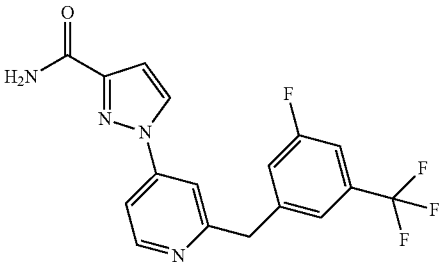
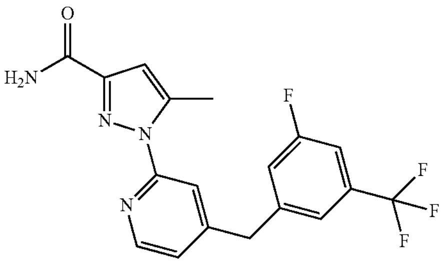
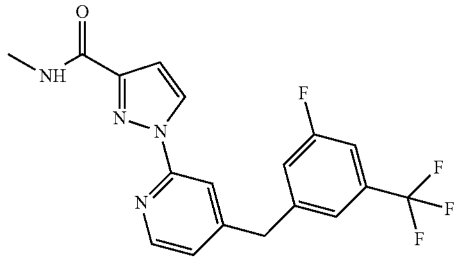
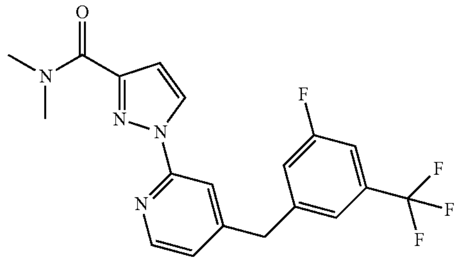
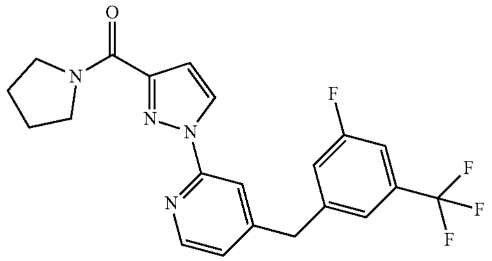
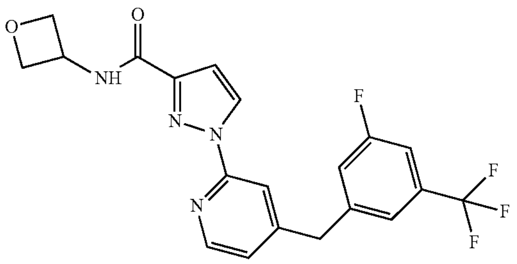

-continued
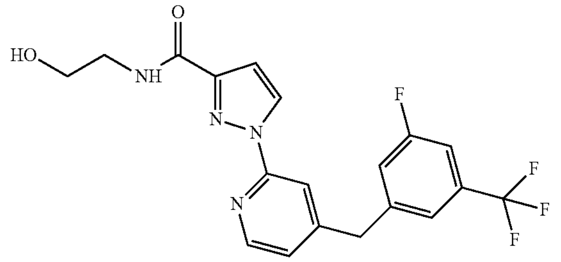
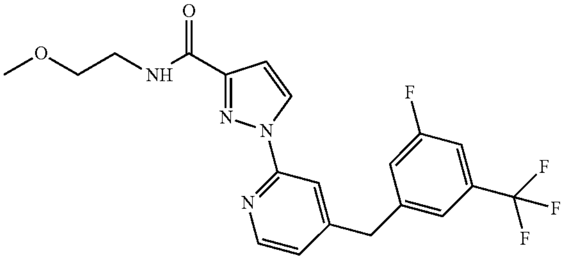
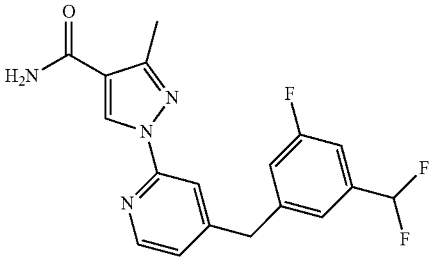
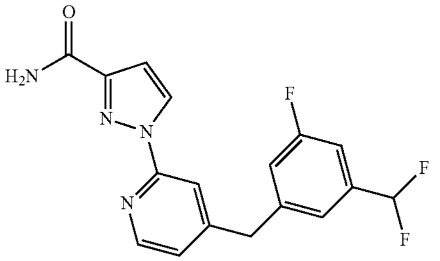
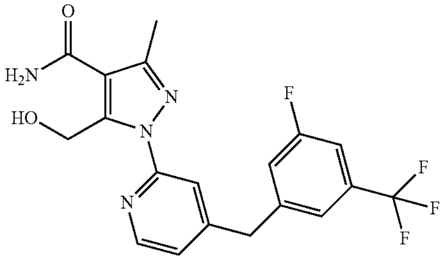
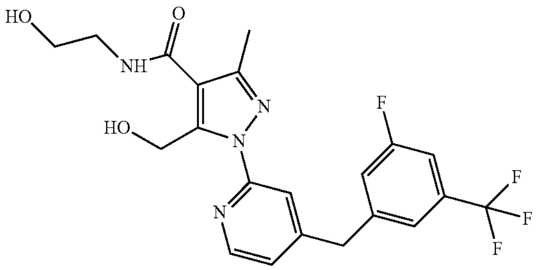
-continued
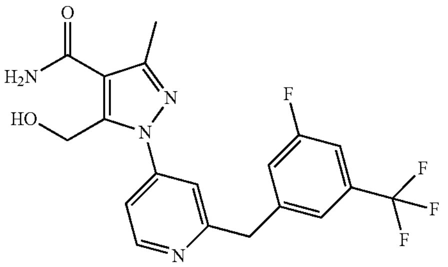
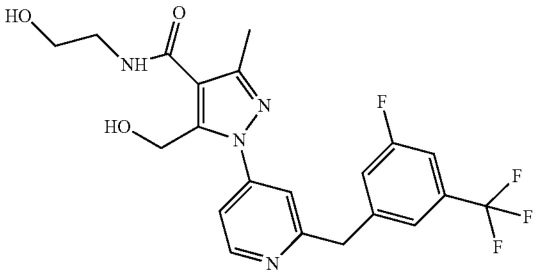
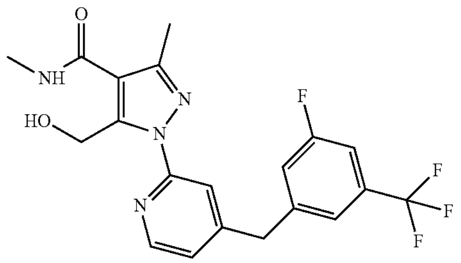
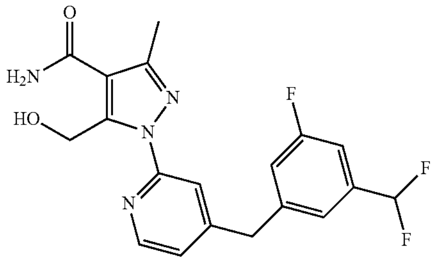
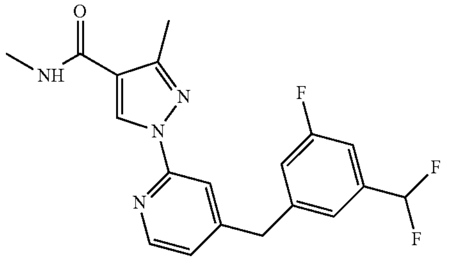
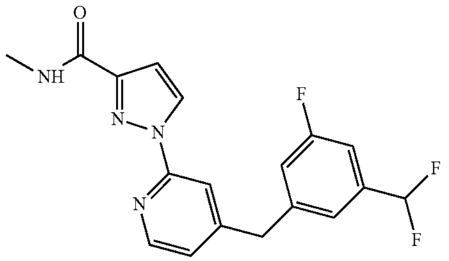

-continued
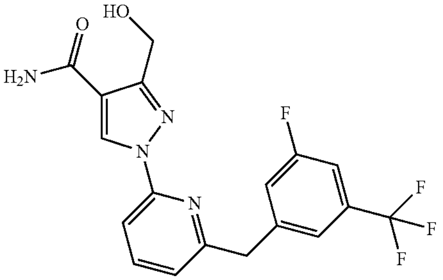
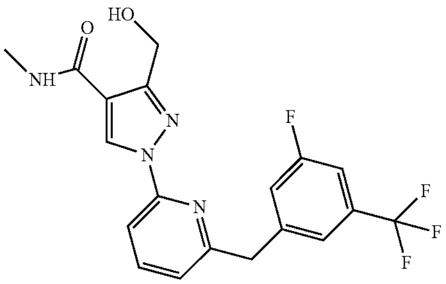
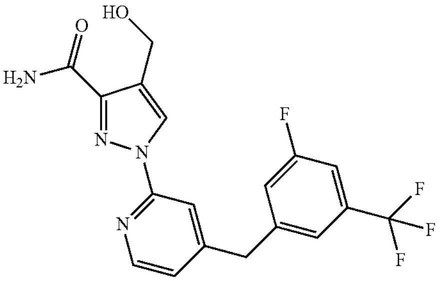
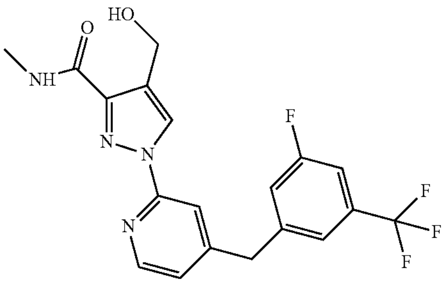
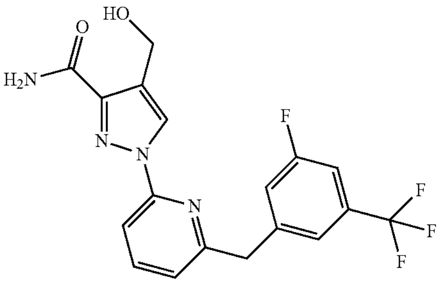
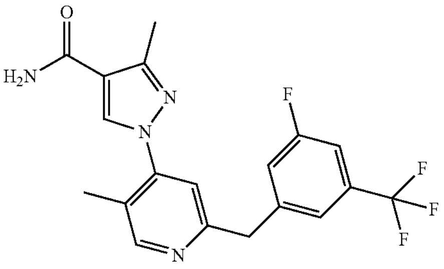
-continued
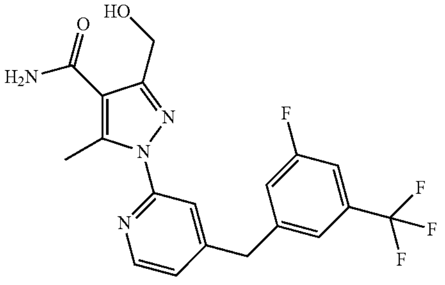
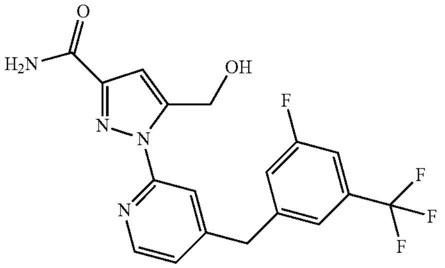
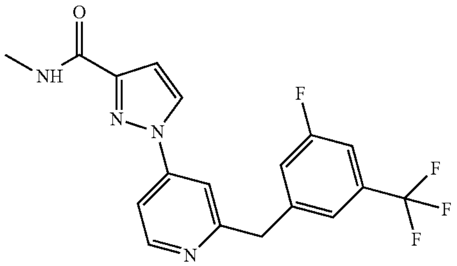
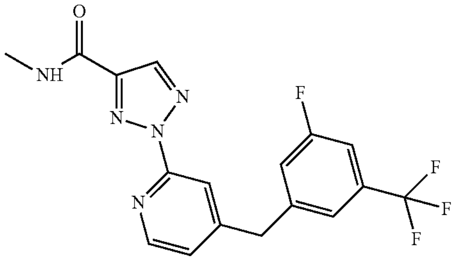
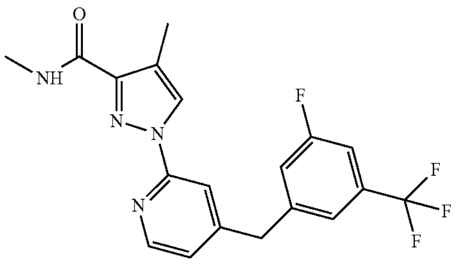
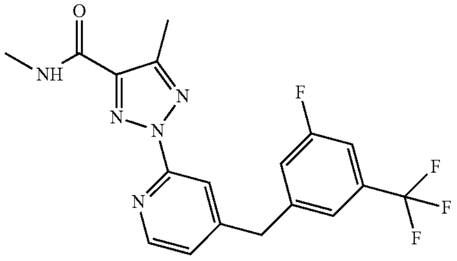

-continued

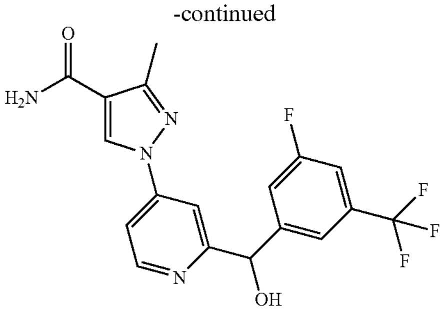

or a salt thereof.

The compound can be selected from the group consisting of:

1-(4-(3-fluoro-5-(trifluoromethyl)benzyl)pyridin-2-yl)-1H-pyrazole-4-carboxamide;
1-(2-(3-fluoro-5-(trifluoromethyl)benzyl)pyridin-4-yl)-1H-pyrazole-4-carboxamide;
1-(4-(3-fluoro-5-(trifluoromethyl)benzyl)pyridin-2-yl)-N-methyl-1H-pyrazole-4-carboxamide;
2-(4-(3-fluoro-5-(trifluoromethyl)benzyl)pyridin-2-yl)-2H-1,2,3-triazole-4-carboxamide;
1-(4-(3-fluoro-5-(trifluoromethyl)benzyl)pyridin-2-yl)-3-methyl-1H-pyrazole-4-carboxamide;
1-(4-(3-fluoro-5-(trifluoromethyl)benzyl)pyridin-2-yl)-3,5-dimethyl-1H-pyrazole-4-carboxamide;
1-(4-(3-fluoro-5-(trifluoromethyl)benzyl)pyridin-2-yl)-5-methyl-1H-pyrazole-4-carboxamide;
1-(2-(3-fluoro-5-(trifluoromethyl)benzyl)pyridin-4-yl)-3-methyl-1H-pyrazole-4-carboxamide;
1-(4-(3-fluoro-5-(trifluoromethyl)benzyl)pyridin-2-yl)-1H-pyrazole-3-carboxamide;
1-(4-(3-fluoro-5-(trifluoromethyl)benzyl)pyridin-2-yl)-4-methyl-1H-pyrazole-3-carboxamide;
1-(2-(3-fluoro-5-(trifluoromethyl)benzyl)pyridin-4-yl)-3-methoxy-1H-pyrazole-4-carboxamide;
2-(2-(3-fluoro-5-(trifluoromethyl)benzyl)pyridin-4-yl)-5-methyl-2H-1,2,3-triazole-4-carboxamide;
2-(4-(3-fluoro-5-(trifluoromethyl)benzyl)pyridin-2-yl)-5-methyl-2H-1,2,3-triazole-4-carboxamide;
1-(4-(3-fluoro-5-(trifluoromethyl)benzyl)pyridin-2-yl)-3-methoxy-1H-pyrazole-4-carboxamide;
1-(6-(3-fluoro-5-(trifluoromethyl)benzyl)pyridin-2-yl)-4-methyl-1H-pyrazole-3-carboxamide;
(1-(2-(3-fluoro-5-(trifluoromethyl)benzyl)pyridin-4-yl)-3-methyl-1H-pyrazol-4-yl)(pyrrolidin-1-yl)methanone;
1-(2-(3-fluoro-5-(trifluoromethyl)benzyl)pyridin-4-yl)-N,3-dimethyl-1H-pyrazole-4-carboxamide;
1-(2-(3-fluoro-5-(trifluoromethyl)benzyl)pyridin-4-yl)-N,N,3-trimethyl-1H-pyrazole-4-carboxamide;
1-(2-(3-fluoro-5-(trifluoromethyl)benzyl)pyridin-4-yl)-3-methyl-N-(oxetan-3-yl)-1H-pyrazole-4-carboxamide;
1-(2-(3-fluoro-5-(trifluoromethyl)benzyl)pyridin-4-yl)-N-(2-hydroxyethyl)-3-methyl-1H-pyrazole-4-carboxamide;
1-(2-(3-fluoro-5-(trifluoromethyl)benzyl)pyridin-4-yl)-N-(2-methoxyethyl)-3-methyl-1H-pyrazole-4-carboxamide;
3-chloro-1-(2-(3-fluoro-5-(trifluoromethyl)benzyl)pyridin-4-yl)-1H-pyrazole-4-carboxamide;
3-(difluoromethyl)-1-(2-(3-fluoro-5-(trifluoromethyl)benzyl)pyridin-4-yl)-1H-pyrazole-4-carboxamide;
1-(2-(3-fluoro-5-(trifluoromethyl)benzyl)pyridin-4-yl)-3-(trifluoromethyl)-1H-pyrazole-4-carboxamide;
3-ethyl-1-(2-(3-fluoro-5-(trifluoromethyl)benzyl)pyridin-4-yl)-1H-pyrazole-4-carboxamide;
3-cyano-1-(2-(3-fluoro-5-(trifluoromethyl)benzyl)pyridin-4-yl)-1H-pyrazole-4-carboxamide;
3-cyclopropyl-1-(2-(3-fluoro-5-(trifluoromethyl)benzyl)pyridin-4-yl)-1H-pyrazole-4-carboxamide;
1-(4-(3-fluoro-5-(trifluoromethyl)benzyl)pyridin-2-yl)-N,5-dimethyl-1H-pyrazole-3-carboxamide;
1-(2-(3-fluoro-5-(trifluoromethyl)benzyl)pyridin-4-yl)-1H-pyrazole-3-carboxamide;
1-(4-(3-fluoro-5-(trifluoromethyl)benzyl)pyridin-2-yl)-5-methyl-1H-pyrazole-3-carboxamide;
1-(4-(3-fluoro-5-(trifluoromethyl)benzyl)pyridin-2-yl)-N-methyl-1H-pyrazole-3-carboxamide;
1-(4-(3-fluoro-5-(trifluoromethyl)benzyl)pyridin-2-yl)-N,N-dimethyl-1H-pyrazole-3-carboxamide;
(1-(4-(3-fluoro-5-(trifluoromethyl)benzyl)pyridin-2-yl)-1H-pyrazol-3-yl)(pyrrolidin-1-yl)methanone:
1-(4-(3-fluoro-5-(trifluoromethyl)benzyl)pyridin-2-yl)-N-(oxetan-3-yl)-1H-pyrazole-3-carboxamide;
1-(4-(3-fluoro-5-(trifluoromethyl)benzyl)pyridin-2-yl)-N-(2-hydroxyethyl)-1H-pyrazole-3-carboxamide;
1-(4-(3-fluoro-5-(trifluoromethyl)benzyl)pyridin-2-yl)-N-(2-methoxyethyl)-1H-pyrazole-3-carboxamide;
1-(4-(3-(difluoromethyl)-5-fluorobenzyl)pyridin-2-yl)-3-methyl-1H-pyrazole-4-carboxamide;
1-(4-(3-(difluoromethyl)-5-fluorobenzyl)pyridin-2-yl)-1H-pyrazole-3-carboxamide;
1-(4-(3-fluoro-5-(trifluoromethyl)benzyl)pyridin-2-yl)-5-(hydroxymethyl)-3-methyl-1H-pyrazole-4-carboxamide;
1-(4-(3-fluoro-5-(trifluoromethyl)benzyl)pyridin-2-yl)-N-(2-hydroxyethyl)-5-(hydroxymethyl)-3-methyl-1H-pyrazole-4-carboxamide;
1-(2-(3-fluoro-5-(trifluoromethyl)benzyl)pyridin-4-yl)-5-(hydroxymethyl)-3-methyl-1H-pyrazole-4-carboxamide;
1-(2-(3-fluoro-5-(trifluoromethyl)benzyl)pyridin-4-yl)-N-(2-hydroxyethyl)-5-(hydroxymethyl)-3-methyl-1H-pyrazole-4-carboxamide;
1-(4-(3-fluoro-5-(trifluoromethyl)benzyl)pyridin-2-yl)-5-(hydroxymethyl)-N,3-dimethyl-1H-pyrazole-4-carboxamide;
1-(4-(3-(difluoromethyl)-5-fluorobenzyl)pyridin-2-yl)-5-(hydroxymethyl)-3-methyl-1H-pyrazole-4-carboxamide;
1-(4-{[3-(difluoromethyl)-5-fluorophenyl]methyl}pyridin-2-yl)-N,3-dimethyl-1H-pyrazole-4-carboxamide;
1-(4-(3-(difluoromethyl)-5-fluorobenzyl)pyridin-2-yl)-N-methyl-1H-pyrazole-3-carboxamide;
1-(6-(3-fluoro-5-(trifluoromethyl)benzyl)pyridin-2-yl)-3-(hydroxymethyl)-1H-pyrazole-4-carboxamide;
1-(6-(3-fluoro-5-(trifluoromethyl)benzyl)pyridin-2-yl)-3-(hydroxymethyl)-N-methyl-1H-pyrazole-4-carboxamide;
1-(4-(3-fluoro-5-(trifluoromethyl)benzyl)pyridin-2-yl)-4-(hydroxymethyl)-1H-pyrazole-3-carboxamide;
1-(4-(3-fluoro-5-(trifluoromethyl)benzyl)pyridin-2-yl)-4-(hydroxymethyl)-N-methyl-1H-pyrazole-3-carboxamide;
1-(6-(3-fluoro-5-(trifluoromethyl)benzyl)pyridin-2-yl)-4-(hydroxymethyl)-1H-pyrazole-3-carboxamide;
1-(2-(3-fluoro-5-(trifluoromethyl)benzyl)-5-methylpyridin-4-yl)-3-methyl-1H-pyrazole-4-carboxamide;
1-(4-(3-fluoro-5-(trifluoromethyl)benzyl)pyridin-2-yl)-3-(hydroxymethyl)-5-methyl-1H-pyrazole-4-carboxamide:
1-(4-(3-fluoro-5-(trifluoromethyl)benzyl)pyridin-2-yl)-5-(hydroxymethyl)-1H-pyrazole-3-carboxamide;
1-(2-(3-fluoro-5-(trifluoromethyl)benzyl)pyridin-4-yl)-N-methyl-1H-pyrazole-3-carboxamide;
2-(4-(3-fluoro-5-(trifluoromethyl)benzyl)pyridin-2-yl)-N-methyl-2H-1,2,3-triazole-4-carboxamide;
1-(4-(3-fluoro-5-(trifluoromethyl)benzyl)pyridin-2-yl)-N,4-dimethyl-1H-pyrazole-3-carboxamide;

2-(4-(3-fluoro-5-(trifluoromethyl)benzyl)pyridin-2-yl)-N,5-dimethyl-2H-1,2,3-triazole-4-carboxamide;

1-(2-((3-fluoro-5-(trifluoromethyl)phenyl)(hydroxy)methyl)pyridin-4-yl)-3-methyl-1H-pyrazole-4-carboxamide;

or a salt thereof.

Further embodiments of the invention include the use of a compound of Formula (1) or a salt thereof or a pharmaceutical composition comprising a compound of Formula (1) as a GPR52 receptor modulator or a GPR52 receptor agonist. Compounds of the present invention may be used as GPR52 modulators. Compounds of the present invention may be used as GPR52 agonists. General references to Formula (1) throughout the specification include all compounds of Formula (1) and Formula (1a).

Compounds of the present invention may be used in the treatment of psychiatric disorders; neuropsychiatric disorders; neurodegenerative disorders; psychotic disorders; cognitive disorders; neurocognitive disorders; extrapyramidal disorders; movement disorders; motor disorders; hyperkinetic movement disorders; catatonia; mood disorders; depressive disorders; anxiety disorders; obsessive-compulsive disorder (OCD); autism spectrum disorders; depressive disorders; hypothalamic disorders; pituitary disorders; prolactin-related disorders; trauma- or stressor-related disorders; disruptive, impulse-control or conduct disorders; sleep-wake disorders; substance-related disorders; addictive disorders; behavioral disorders; hypofrontality; abnormalities in the tuberoinfundibular, mesolimbic, mesocortical, or nigrostriatal pathway; decreased activity in the striatum; cortical dysfunction; neurocognitive dysfunction or conditions or symptoms related thereto.

Compounds of the present invention may be used in the treatment of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, anhedonia, agitation, Alzheimer's disease, Parkinson's disease, Huntington's disease, vascular dementia, Lewy body disease, frontotemporal dementia, Tourette's syndrome, hyperprolactinemia, pituitary adenoma, prolactinoma, craniopharyngioma, Cushing's disease, diabetes insipidus, non-functioning tumours, obesity, posttraumatic stress disorder (PTSD), akathisia and associated movements, athetosis, ataxia, ballismus, hemiballismus, chorea, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, tremor, Wilson's disease, schizotypal personality disorder, delusional disorder, brief psychotic disorder, schizophreniform disorder, schizoaffective disorder, substance- or medication-induced psychotic disorder, delusions, hallucinations, disorganized thinking, grossly disorganized or abnormal motor behavior, catatonia, major depressive disorder, bipolar I disorder, bipolar II disorder, cyclothymic disorder, substance- or medication-induced bipolar and related disorders, bipolar and related disorders due to another medical condition, separation anxiety disorder, selective mutism, specific phobia, social anxiety disorder, panic disorder, agoraphobia, generalized anxiety disorder, substance- or medication-induced anxiety disorder, anxiety disorders due to another medical condition, delirium, major neurocognitive disorder, minor neurocognitive disorder, amnesia, dementia, developmental coordination disorder, stereotypic movement disorder, a post-stroke effect, dentatorubral-pallidoluysian atrophy, diminished emotional expression, avolition, alogia and asociality.

Compounds of the present invention may be used in the treatment of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, neurocognitive disorder, delirium, anhedonia, agitation, Alzheimer's disease, Parkinson's disease, Huntington's disease, vascular dementia, Lewy body disease, frontotemporal dementia, Tourette's syndrome, hyperprolactinemia, obesity, and posttraumatic stress disorder (PTSD). Compounds of the present invention may be used in the treatment of schizophrenia.

Definitions

In this application, the following definitions apply, unless indicated otherwise.

The term "GPR52 modulator" as used herein refers to any compound which binds to and modulates the function of the GPR52 receptor. The term "modulator" should be interpreted to include modulation by modalities including, but not limited to, agonists, partial agonists and inverse agonists.

The term "treatment", in relation to the uses of any of the compounds described herein, including those of Formula (1) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

Terms such as "alkyl", "cycloalkyl" "alkoxy" and "halo" are all used in their conventional sense (e.g. as defined in the IUPAC Gold Book), unless indicated otherwise. "optionally substituted" as applied to any group means that the said group may if desired be substituted with one or more substituents, which may be the same or different.

Examples of heteroatom replacements for carbon atoms include replacement of a carbon atom in a $-CH_2-CH_2-CH_2-$ chain with oxygen or sulfur to give an ether $-CH_2-O-CH_2-$ or thioether $-CH_2-S-CH_2-$, replacement of a carbon atom in a group $CH_2-C{\equiv}C-H$ with nitrogen to give a nitrile (cyano) group $CH_2-C{\equiv}N$, replacement of a carbon atom in a group $-CH_2-CH_2-CH_2-$ with $C{=}O$ to give a ketone $-CH_2-C(O)-CH_2-$, replacement of a carbon atom in a group $-CH_2-CH{=}CH_2$ with $C{=}O$ to give an aldehyde $-CH_2-C(O)H$, replacement of a carbon atom in a group $-CH_2-CH_2-CH_3$ with O to give an alcohol $-CH_2-CH_2-CH_2OH$, replacement of a carbon atom in a group $-CH_2-CH_2-CH_3$ with O to give an ether $-CH_2-O-CH_3$, replacement of a carbon atom in a group $-CH_2-CH_2-CH_3$ with S to give an thiol $-CH_2-CH_2-CH_2SH$, replacement of a carbon atom in a group $-CH_2-CH_2-CH_2-$ with $S{=}O$ or $SO_2$ to give a sulfoxide $-CH_2-S(O)-CH_2-$ or sulfone $-CH_2-S(O)_2-CH_2-$, replacement of a carbon atom in a $-CH_2-CH_2-CH_2-$ chain with C(O)NH to give an amide $-CH_2-CH_2-C(O)-NH-$, replacement of a carbon atom in a $-CH_2-CH_2-CH_2-$ chain with nitrogen to give an amine $-CH_2-NH-CH_2-$, and replacement of a carbon atom in a $-CH_2-CH_2-CH_2-$ chain with C(O)O to give an ester (or carboxylic acid) $-CH_2-CH_2-C(O)-O-$. In each such replacement, at least one carbon atom of the alkyl group must remain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$ In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound.

Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in some embodiments of the invention, there is provided a pharmaceutical composition comprising at least one compound of Formula (1) as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the Formula (1) can be formulated in accordance with known techniques, see for example, Remington's Pharmaceutical Sciences, Mack Publishing Company, Easton, PA, USA. The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments.

Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack. The compounds of the Formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the following examples shown in Table 1.

TABLE 1
Examples
Example 1
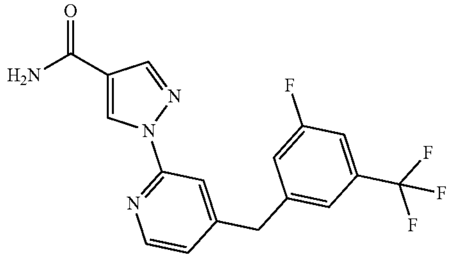 [SMILES: NC(=O)c1cnn(-c2cc(Cc3cc(F)cc(C(F)(F)F)c3)ccn2)c1]
Example 2
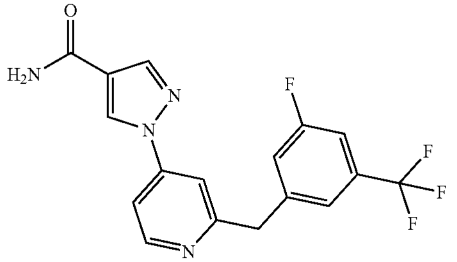 [SMILES: NC(=O)c1cnn(-c2ccnc(Cc3cc(F)cc(C(F)(F)F)c3)c2)c1]
Example 3
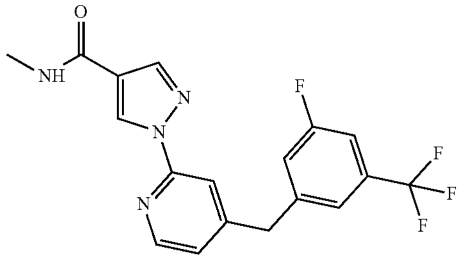 [SMILES: CNC(=O)c1cnn(-c2cc(Cc3cc(F)cc(C(F)(F)F)c3)ccn2)c1]
Example 4
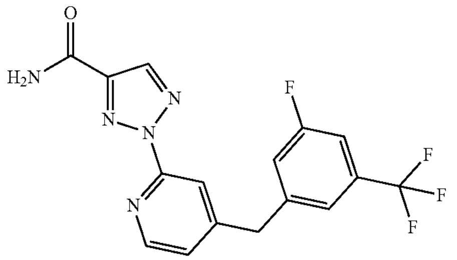 [SMILES: NC(=O)c1cnn(-c2cc(Cc3cc(F)cc(C(F)(F)F)c3)ccn2)n1]
Example 5
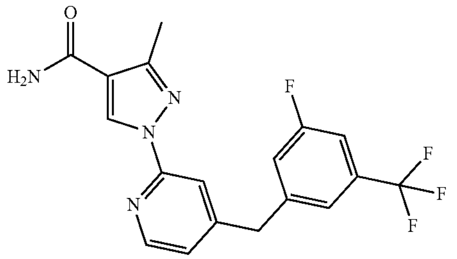 [SMILES: Cc1nn(-c2cc(Cc3cc(F)cc(C(F)(F)F)c3)ccn2)cc1C(N)=O]
Example 6
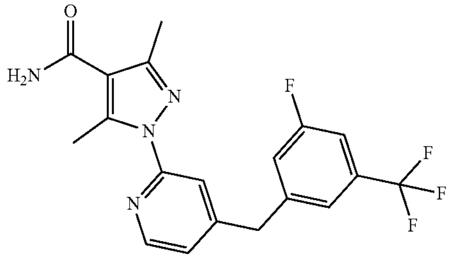 [SMILES: Cc1nn(-c2cc(Cc3cc(F)cc(C(F)(F)F)c3)ccn2)c(C)c1C(N)=O]
TABLE 1-continued
Examples
Example 7
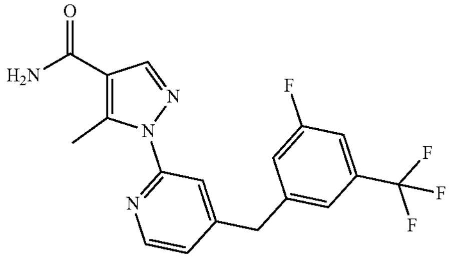 [SMILES: Cc1c(C(N)=O)cnn1-c1cc(Cc2cc(F)cc(C(F)(F)F)c2)ccn1]
Example 8
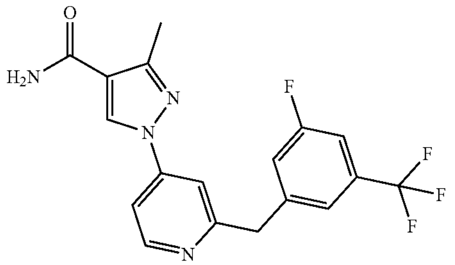 [SMILES: Cc1nn(-c2ccnc(Cc3cc(F)cc(C(F)(F)F)c3)c2)cc1C(N)=O]
Example 9
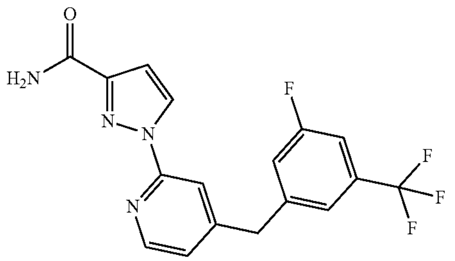 [SMILES: NC(=O)c1ccn(-c2cc(Cc3cc(F)cc(C(F)(F)F)c3)ccn2)n1]
Example 10
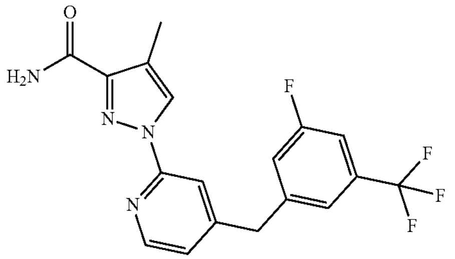 [SMILES: Cc1cn(-c2cc(Cc3cc(F)cc(C(F)(F)F)c3)ccn2)nc1C(N)=O]
Example 11
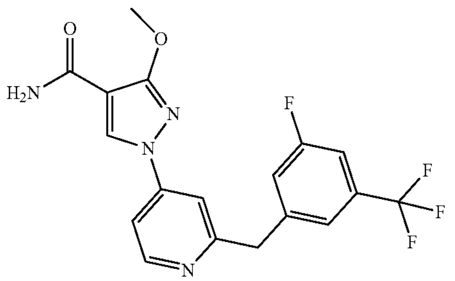 [SMILES: COc1nn(-c2ccnc(Cc3cc(F)cc(C(F)(F)F)c3)c2)cc1C(N)=O]

TABLE 1-continued
Examples
Example 12
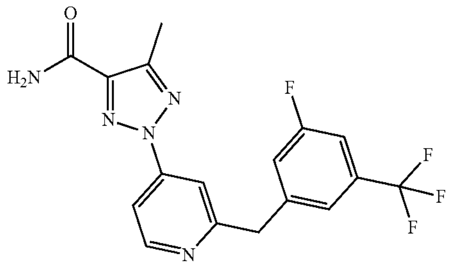 [SMILES: Cc1nn(-c2ccnc(Cc3cc(F)cc(C(F)(F)F)c3)c2)nc1C(N)=O]
Example 13
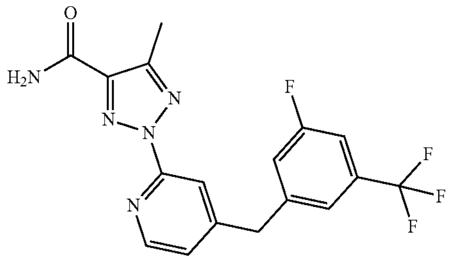 [SMILES: Cc1nn(-c2cc(Cc3cc(F)cc(C(F)(F)F)c3)ccn2)nc1C(N)=O]
Example 14
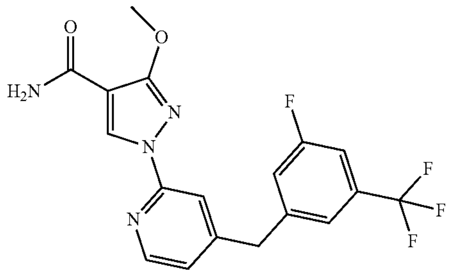 [SMILES: COc1nn(-c2cc(Cc3cc(F)cc(C(F)(F)F)c3)ccn2)cc1C(N)=O]
Example 15
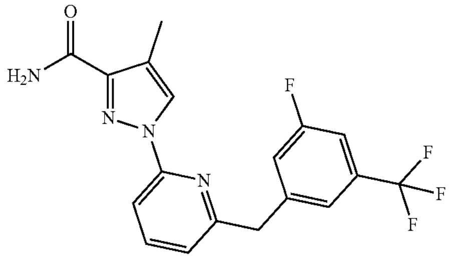 [SMILES: Cc1cn(-c2cccc(Cc3cc(F)cc(C(F)(F)F)c3)n2)nc1C(N)=O]
Example 16
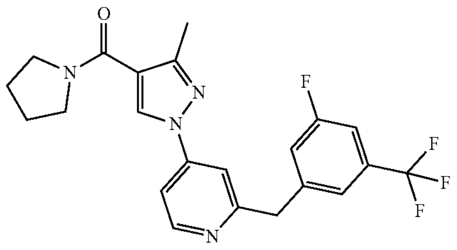 [SMILES: Cc1nn(-c2ccnc(Cc3cc(F)cc(C(F)(F)F)c3)c2)cc1C(=O)N1CCCC1]
Example 17
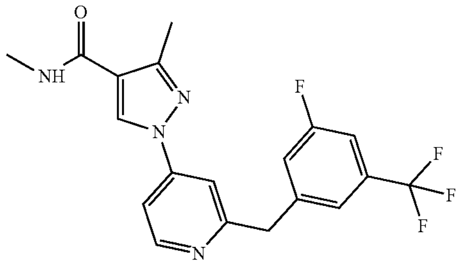 [SMILES: CNC(=O)c1cn(-c2ccnc(Cc3cc(F)cc(C(F)(F)F)c3)c2)nc1C]
TABLE 1-continued
Examples
Example 18
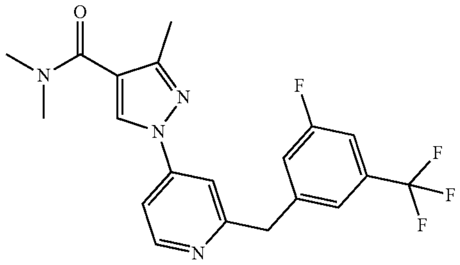 [SMILES: Cc1nn(-c2ccnc(Cc3cc(F)cc(C(F)(F)F)c3)c2)cc1C(=O)N(C)C]
Example 19
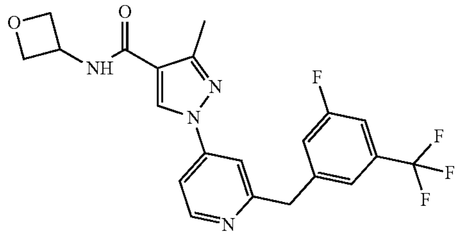 [SMILES: Cc1nn(-c2ccnc(Cc3cc(F)cc(C(F)(F)F)c3)c2)cc1C(=O)NC1COC1]
Example 20
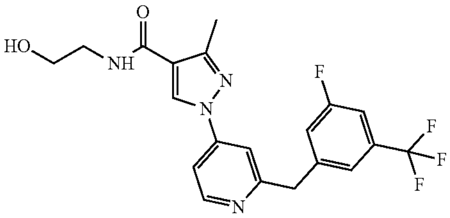 [SMILES: Cc1nn(-c2ccnc(Cc3cc(F)cc(C(F)(F)F)c3)c2)cc1C(=O)NCCO]
Example 21
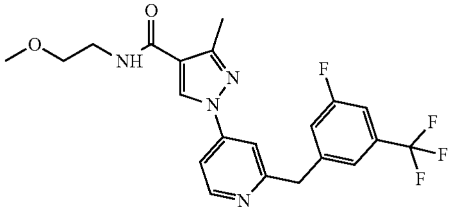 [SMILES: COCCNC(=O)c1cn(-c2ccnc(Cc3cc(F)cc(C(F)(F)F)c3)c2)nc1C]
Example 22
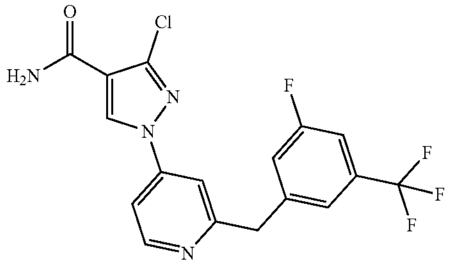 [SMILES: NC(=O)c1cn(-c2ccnc(Cc3cc(F)cc(C(F)(F)F)c3)c2)nc1Cl]
Example 23
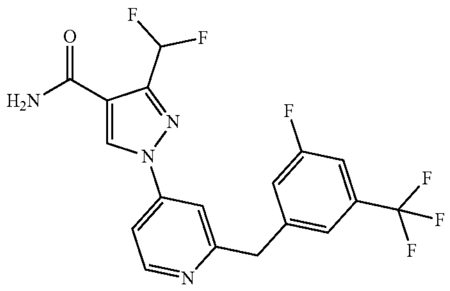 [SMILES: NC(=O)c1cn(-c2ccnc(Cc3cc(F)cc(C(F)(F)F)c3)c2)nc1C(F)F]

TABLE 1-continued
Examples
Example 24
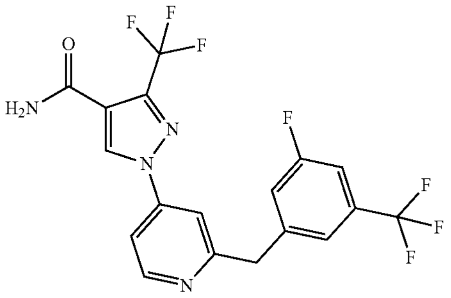 [SMILES: NC(=O)c1cn(-c2ccnc(Cc3cc(F)cc(C(F)(F)F)c3)c2)nc1C(F)(F)F]
Example 25
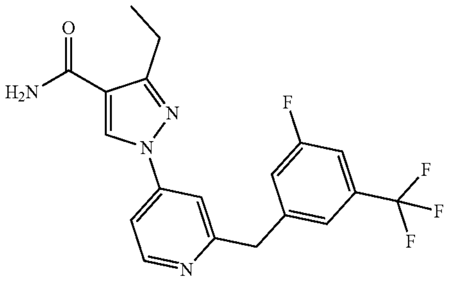 [SMILES: CCc1nn(-c2ccnc(Cc3cc(F)cc(C(F)(F)F)c3)c2)cc1C(N)=O]
Example 26
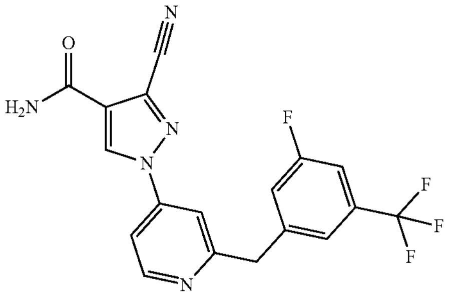 [SMILES: N#Cc1nn(-c2ccnc(Cc3cc(F)cc(C(F)(F)F)c3)c2)cc1C(N)=O]
Example 27
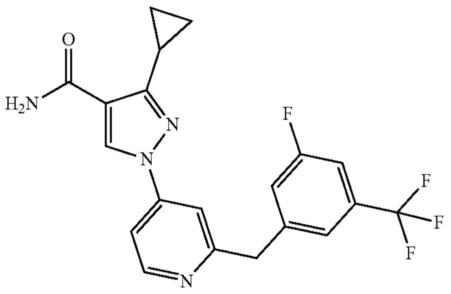 [SMILES: NC(=O)c1cn(-c2ccnc(Cc3cc(F)cc(C(F)(F)F)c3)c2)nc1C1CC1]
Example 28
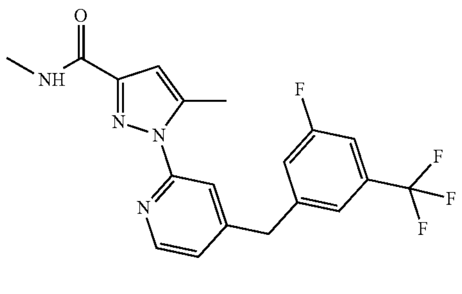 [SMILES: CNC(=O)c1cc(C)n(-c2cc(Cc3cc(F)cc(C(F)(F)F)c3)ccn2)n1]
TABLE 1-continued
Examples
Example 29
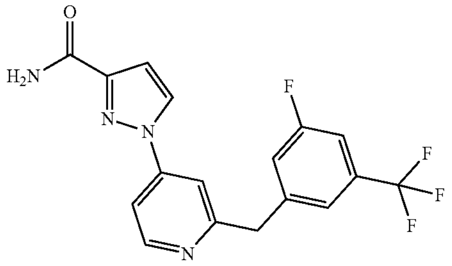 [SMILES: NC(=O)c1ccn(-c2ccnc(Cc3cc(F)cc(C(F)(F)F)c3)c2)n1]
Example 30
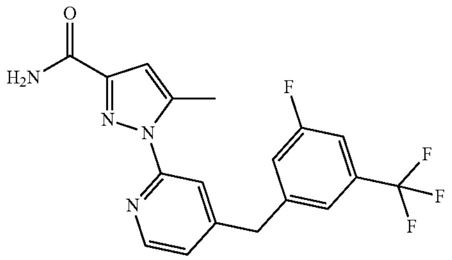 [SMILES: Cc1cc(C(N)=O)nn1-c1cc(Cc2cc(F)cc(C(F)(F)F)c2)ccn1]
Example 31
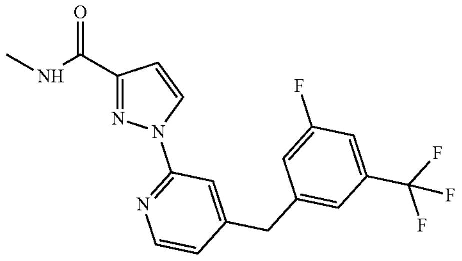 [SMILES: CNC(=O)c1ccn(-c2cc(Cc3cc(F)cc(C(F)(F)F)c3)ccn2)n1]
Example 32
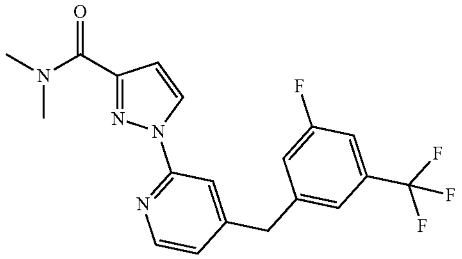 [SMILES: CN(C)C(=O)c1ccn(-c2cc(Cc3cc(F)cc(C(F)(F)F)c3)ccn2)n1]
Example 33
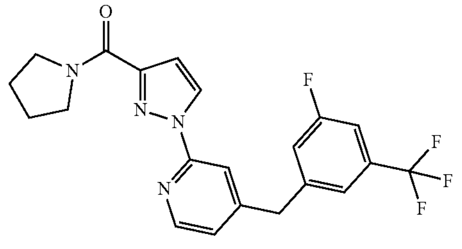 [SMILES: O=C(c1ccn(-c2cc(Cc3cc(F)cc(C(F)(F)F)c3)ccn2)n1)N1CCCC1]
Example 34
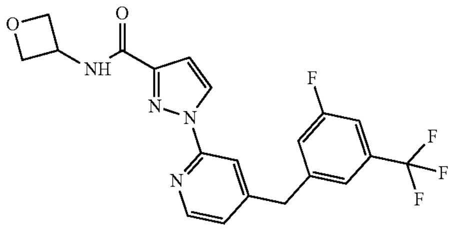 [SMILES: O=C(NC1COC1)c1ccn(-c2cc(Cc3cc(F)cc(C(F)(F)F)c3)ccn2)n1]

TABLE 1-continued
| Examples |
| --- |
| Example 35 |
| 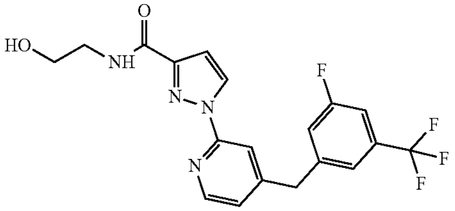 [SMILES: O=C(NCCO)c1ccn(-c2cc(Cc3cc(F)cc(C(F)(F)F)c3)ccn2)n1] |
| Example 36 |
| 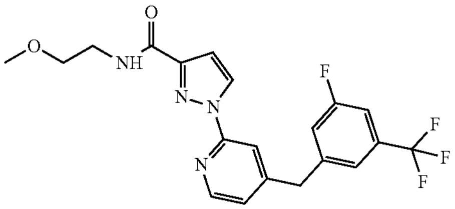 [SMILES: COCCNC(=O)c1ccn(-c2cc(Cc3cc(F)cc(C(F)(F)F)c3)ccn2)n1] |
| Example 37 |
| 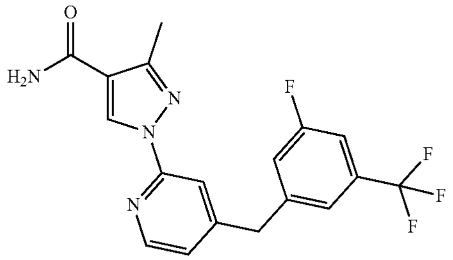 |
| Example 38 |
| 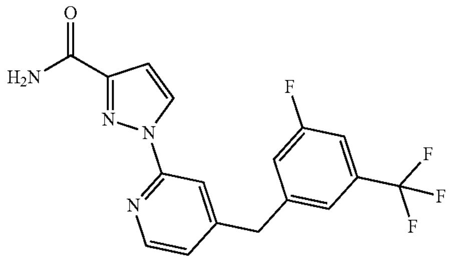 [SMILES: NC(=O)c1ccn(-c2cc(Cc3cc(F)cc(C(F)(F)F)c3)ccn2)n1] |
| Example 39 |
| 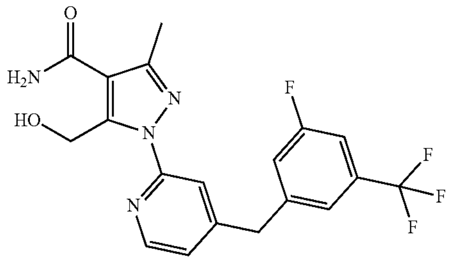 [SMILES: Cc1nn(-c2cc(Cc3cc(F)cc(C(F)(F)F)c3)ccn2)c(CO)c1C(N)=O] |
| Example 40 |
| 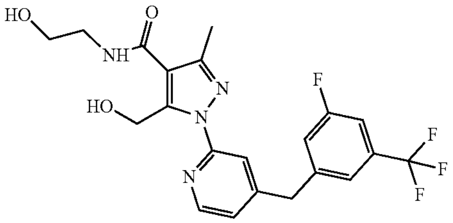 [SMILES: Cc1nn(-c2cc(Cc3cc(F)cc(C(F)(F)F)c3)ccn2)c(CO)c1C(=O)NCCO] |
TABLE 1-continued
| Examples |
| --- |
| Example 41 |
| 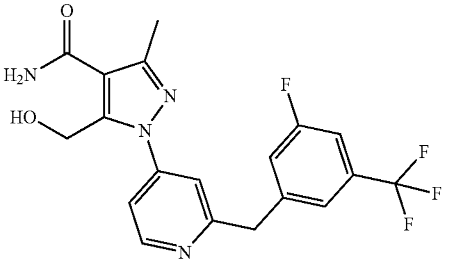 [SMILES: Cc1nn(-c2ccnc(Cc3cc(F)cc(C(F)(F)F)c3)c2)c(CO)c1C(N)=O] |
| Example 42 |
| 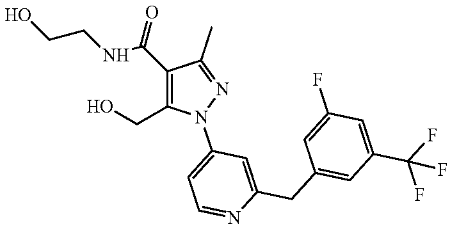 [SMILES: Cc1nn(-c2ccnc(Cc3cc(F)cc(C(F)(F)F)c3)c2)c(CO)c1C(=O)NCCO] |
| Example 43 |
| 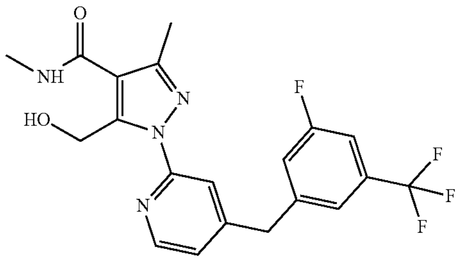 [SMILES: CNC(=O)c1c(C)nn(-c2cc(Cc3cc(F)cc(C(F)(F)F)c3)ccn2)c1CO] |
| Example 44 |
| 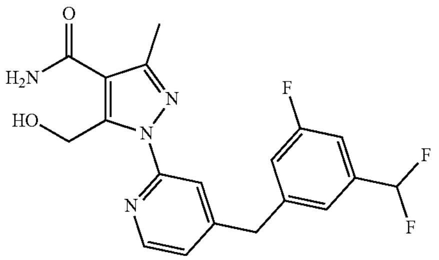 [SMILES: Cc1nn(-c2cc(Cc3cc(F)cc(C(F)F)c3)ccn2)c(CO)c1C(N)=O] |
| Example 45 |
| 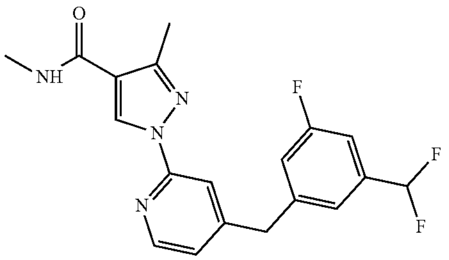 [SMILES: CNC(=O)c1cn(-c2cc(Cc3cc(F)cc(C(F)F)c3)ccn2)nc1C] |
| Example 46 |
| 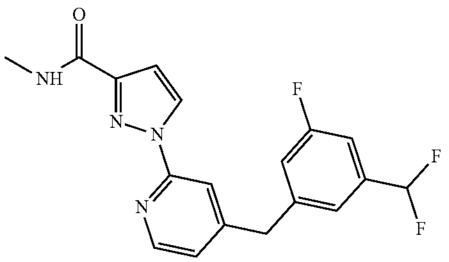 [SMILES: CNC(=O)c1ccn(-c2cc(Cc3cc(F)cc(C(F)F)c3)ccn2)n1] |

TABLE 1-continued
TABLE 1-continued
| Examples |
|---|
| Example 47 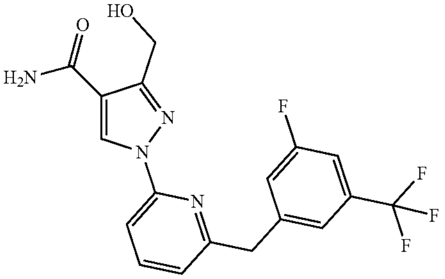 [SMILES: NC(=O)c1cn(-c2cccc(Cc3cc(F)cc(C(F)(F)F)c3)n2)nc1CO] |
| Example 48 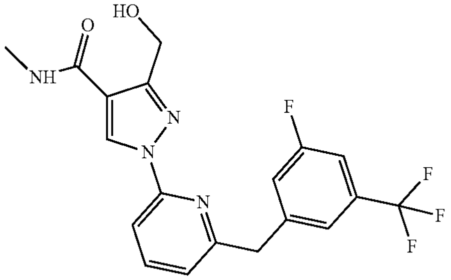 [SMILES: CNC(=O)c1cn(-c2cccc(Cc3cc(F)cc(C(F)(F)F)c3)n2)nc1CO] |
| Example 49 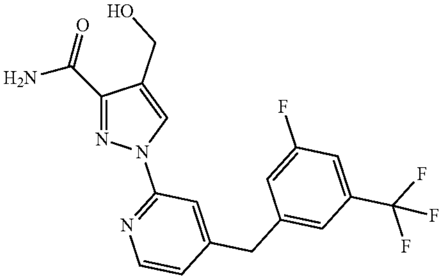 [SMILES: NC(=O)c1nn(-c2cc(Cc3cc(F)cc(C(F)(F)F)c3)ccn2)cc1CO] |
| Example 50 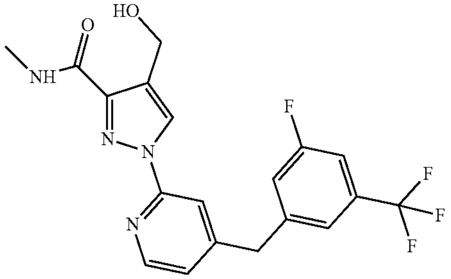 [SMILES: CNC(=O)c1nn(-c2cc(Cc3cc(F)cc(C(F)(F)F)c3)ccn2)cc1CO] |
| Example 51 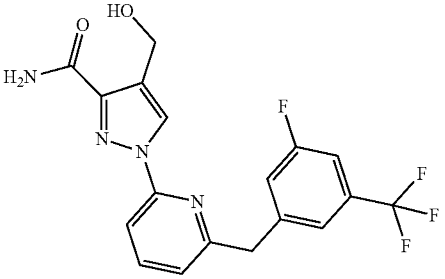 [SMILES: NC(=O)c1nn(-c2cccc(Cc3cc(F)cc(C(F)(F)F)c3)n2)cc1CO] |
| Example 52 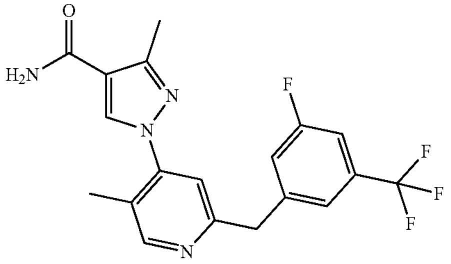 [SMILES: Cc1cnc(Cc2cc(F)cc(C(F)(F)F)c2)cc1-n1cc(C(N)=O)c(C)n1] |
| Example 53 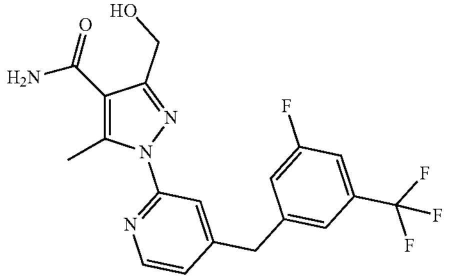 [SMILES: Cc1c(C(N)=O)c(CO)nn1-c1cc(Cc2cc(F)cc(C(F)(F)F)c2)ccn1] |
| Example 54 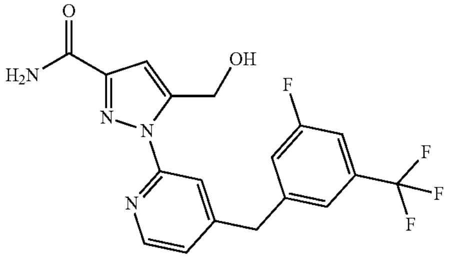 [SMILES: NC(=O)c1cc(CO)n(-c2cc(Cc3cc(F)cc(C(F)(F)F)c3)ccn2)n1] |
| Example 55 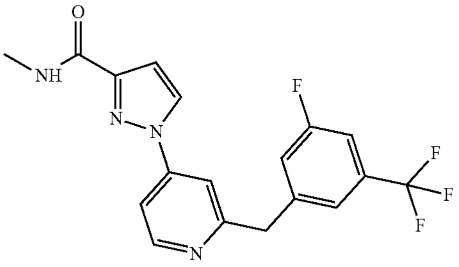 [SMILES: CNC(=O)c1ccn(-c2ccnc(Cc3cc(F)cc(C(F)(F)F)c3)c2)n1] |
| Example 56 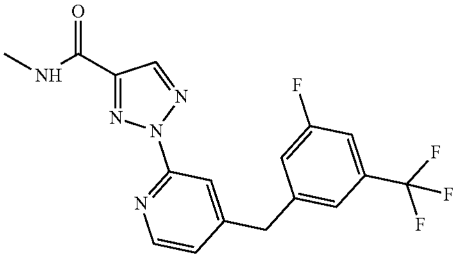 |

TABLE 1-continued

| Examples |
| --- |
| Example 57 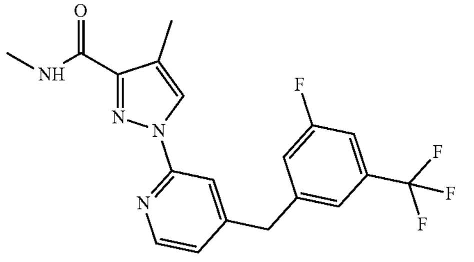 [SMILES: CNC(=O)c1nn(-c2cc(Cc3cc(F)cc(C(F)(F)F)c3)ccn2)cc1C] |
| Example 58 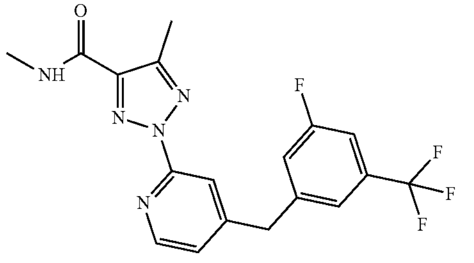 [SMILES: CNC(=O)c1nn(-c2cc(Cc3cc(F)cc(C(F)(F)F)c3)ccn2)nc1C] |
| Example 59 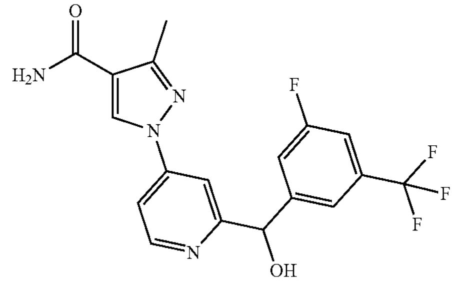 [SMILES: Cc1nn(-c2ccnc(C(O)c3cc(F)cc(C(F)(F)F)c3)c2)cc1C(N)=O] |

Preparation of the Compounds of the Invention

Compounds of Formula (1) can be prepared in accordance with synthetic methods known to the skilled person. The invention also provides a process for the preparation of a compound as defined in Formula (1) above. Where intermediates are commercially available, they are identified by their chemical abstracts service (CAS) reference number in Table 3, where not commercially available the synthesis of the intermediates using standard transformations is detailed herein. Commercial reagents were utilized without further purification.

General Procedures Room temperature (RT) refers to approximately 20-27° C. $^1$H NMR spectra were typically recorded at 400 MHz at ambient temperature unless otherwise specified. Chemical shift values are expressed in parts per million (ppm), i.e. (δ)-values. Standard abbreviations, or their combinations, are used for the multiplicity of the NMR signals, for example: s=singlet, br=broad, d=doublet, t=triplet, q=quartet, quin=quintet or p=pentet, h=heptet, dd=doublet of doublets, dt=doublet of triplets, m=multiplet. Coupling constants are listed as J values, measured in Hz. NMR and mass spectroscopy results were corrected to account for background peaks. Chromatography refers to column chromatography performed using silica or C18 silica and executed under positive pressure (flash chromatography) conditions.

LCMS Methods

LCMS experiments were carried out using electrospray conditions under the conditions below (Solvents: A1=0.1% TFA in $H_2O$:MeCN (95:5); A2=5 mM ammonium acetate in $H_2O$; A3=2.5 L $H_2O$+2.5 mL 28% ammonia in $H_2O$ solution; A4=0.1% $HCO_2H$ in $H_2O$:MeCN (95:5); A5=10 mM $NH_4HCO_3$ in $H_2O$; A6=0.2% of 28% ammonia solution in $H_2O$; A7=0.1% TFA in $H_2O$; A8=50 mM ammonium acetate pH 7.4; A9=10 mM ammonium acetate in $H_2O$; 1=0.1% TFA in MeCN; B2=MeCN; B3=2.5 L MeCN+135 mL $H_2O$+2.5 mL 28% ammonia in $H_2O$ solution. LCMS data are given in the format: Mass ion, electrospray mode (positive or negative), retention time (experimental text and Table 2); Mass ion, electrospray mode (positive or negative), retention time, approximate purity (Table 3).

Method 1. Instruments: Agilent Technologies 1290 Infinity II Series LC, 6125 Quadrupole MSD SL; Column: Zorbax XDB C18, 5 micron; Gradient [time (min)/solvent B2 in A4 (%)]:0.00/5, 2.50/95, 4.00/95, 4.50/5, 6.00/5; Injection volume 1 μL; UV detection 210-400 nm; Column temperature 25° C.; Flow rate 1.5 mL/min.

Method 2. Instruments: Waters Acquity UPLC, Waters 3100 PDA Detector, SQD; Column: Acquity BEH C-18, 1.7 micron, 2.1×100 mm; Gradient [time (min)/solvent B2 in A2 (%)]: 0.00/2, 2.00/2, 7.00/50, 8.50/80, 9.50/2, 10.0/2; Injection volume 1 μL; Detection wavelength 214 nm; Column temperature 30° C.; Flow rate 0.3 mL per min.

Method 3. Instruments: Hewlett Packard 1100 with G1315A DAD, Micromass ZQ; Column: Phenomenex Gemini-NX C18, 3 micron, 2.0×30 mm; Gradient [time (min)/solvent B3 in A3 (%)]: 0.00/2, 0.10/2, 8.40/95, 10.00/95; Injection volume 1 μL; UV detection 230 to 400 nM; Column temperature 45° C.; Flow rate 1.5 mL/min.

Method 4. Instruments: Waters Acquity UPLC, Waters 3100 PDA Detector, SQD; Column: Acquity BEH C-18, 1.7 micron, 2.1×100 mm; Gradient [time (min)/solvent B2 in A2 (%)]: 0.00/5, 0.25/5, 1.50/35, 2.50/95, 3.20/95 3.60/5, 4.00/5; Injection volume 1 μL; Detection wavelength 214 nm; Column temperature 35° C.; Flow rate 0.6 mL per min to 3.20 min then 0.8 mL per min.

Method 5. Instruments: Waters Acquity UPLC, Waters 3100 PDA Detector, SQD; Column: Acquity HSS-T3, 1.8 micron, 2.1×100 mm; Gradient [time (min)/solvent B2 in A7 (%)]: 0.00/10, 1.00/10, 2.00/15, 4.50/55, 6.00/90, 8.00/90, 9.00/10, 10.00/10; Injection volume 1 μL; Detection wavelength 214 nm; Column temperature 30° C.; Flow rate 0.3 mL per min.

Method 6. Instruments: Hewlett Packard 1100 with G1315A DAD, Micromass ZQ; Column: Phenomenex Gemini-NX C18, 3 micron, 2.0×30 mm; Gradient [time (min)/solvent B3 in A3 (%)]: 0.00/2, 0.10/2, 2.5/95, 3.5/95; Injection volume 1 μL; UV detection 230 to 400 nM; Column temperature 45° C.; Flow rate 1.5 mL/min.

Method 7. Instruments: Agilent Technologies 1290 Infinity II Series LC, 6125 Quadrupole MSD SL; Column: Zorbax eclipse plus C18, 1.8 micron, 2.1×50 mm; Gradient [time (min)/solvent B2 in A4 (%)]:0.0/05, 0.25/05, 2.5/100, 3.0/100, 3.1/05, 4.0/05; Injection volume 1 μL; UV detection 210-400 nm; Column temperature 25° C.; Flow rate 0.8 mL/min.

Method 8. Instruments: Agilent Technologies 1260 LC with Chemstation software, Diode Array Detector, Agilent 6120 Quadrupole MS with APCI and ES Source; Column: Phenomenex Gemini-NX C18, 3 micron, 2×30 mm; Gradient [time (min)/solvent B3 in A3 (%)]:0.00/5, 2.00/95, 2.50/95, 2.60/5, 3.00/5; Injection volume 0.5 μL; UV detection 190-400 nm; column temperature 40° C.; Flow rate 1.5 mL/min.

Method 9. Instruments: Agilent Technologies 1260 LC with Chemstation software, Diode Array Detector, Agilent 6120 Quadrupole MS with APCI and ES Source; Column:

Phenomenex Gemini-NX C18, 3 micron, 2×30 mm; Gradient [time (min)/solvent B3 in A3 (%)]:0.00/2, 0.10/2, 8.40/95, 10.0/95, 10.1/2, 12.0/2; Injection volume 0.5 μL; UV detection 190-400 nm; column temperature 40° C.; Flow rate 1.5 mL/min.

Method 10. Instruments: Waters Acquity H-Class UPLC MS system with MassLynx software, Photo Diode Array Detector (PDA), QDa Mass detector with Electrospray source; Column: Phenomenex Gemini-NX C18, 3 micron, 2.1×50 mm; Gradient [time (min)/solvent B2 in A8 (%)]: 0.00/0, 1.3/100, 1.55/100, 1.6/0, 3.0/0; Injection volume 1 μL; UV detection 200-500 nm; column temperature 40° C.; Flow rate 0.5 mL/min.

Method 11. Instruments: Agilent Technologies 1290 Infinity II Series LC, 6125 Quadrupole MSD SL; Column: Waters XBridgeC8 3.5 micron, 4.6×50 mm; Gradient [time (min)/solvent 1 in A1 (%)]:0.0/5, 2.5/95, 4.0/95, 4.5/5, 6.0/5; Injection volume 1 μL; UV detection 210 to 400 nM; Column temperature 25° C.; 1.5 mL/min.

Method 12. Instruments: Agilent Technologies 1290 Infinity II Series LC, 6125 Quadrupole MSD SL; Column: Atlantis dC18 5 micron, 4.6×50 mm; Gradient [time (min)/solvent B2 in A1 (%)]:0.0/5, 2.5/95, 4.0/95, 4.5/5, 6.0/5; Injection volume 1 μL; UV detection 210 to 400 nM; Column temperature 25° C.; 1.5 mL/min.

Method 13. Instruments: Agilent Technologies 1290 Infinity II Series LC, 6125 Quadrupole MSD SL; Column: Waters XBridgeC8 3.5 micron, 4.6×50 mm; Gradient [time (min)/solvent B2 in A5 (%)]:0.0/10, 4.0/95, 5.0/95, 5.5/10, 7.0/10; Injection volume 1 μL; UV detection 210 to 400 nM; Column temperature 25° C.; 1.2 mL/min.

Method 14. Instruments: Agilent Technologies 1290 Infinity II Series LC, 6125 Quadrupole MSD SL; Column: Acquity BEH C18 1.7 micron, 2.1×50 mm; Gradient [time (min)/solvent B2 in A9 (%)]:0.0/5, 0.25/5, 2.5/100, 3.0/100, 3.1/5, 4.0/5; Injection volume 1 μL; UV detection 210 to 400 nM; Column temperature 25° C.; 0.8 mL/min.

Method 15. Instruments: Agilent Technologies 1290 Infinity II Series LC, 6125 Quadrupole MSD SL; Column: Acquity BEH C8 1.7 micron, 2.1×50 mm; Gradient [time (min)/solvent B2 in A9 (%)]:0.0/5, 0.25/5, 2.5/100, 3.0/100, 3.1/5, 4.0/5; Injection volume 1 μL; UV detection 210 to 400 nM; Column temperature 25° C.; 0.8 mL/min.

GCMS Methods

GCMS data are given in the format: Mass ion, electrospray mode (positive or negative), retention time.

Method 1. Instrument: Agilent GCMS 7890B; Column: HP-5 ms UI (30m×250 μm×0.25 μm); Inlet temp: 250° C.; Split ratio: 75:1; Oven temp: 50° C., hold time 3 min; Ramp 1: 40° C./min to 300° C., hold time 2 min; Detector temperature: 310° C.; Column flow: 2 mL/min; Air flow: 300 mL/min; $H_2$ flow: 40 mL/min; Make up flow (He): 25 mL/min; Source temp: 230° C.

Method 2. Instrument: Agilent GCMS 7890B; Column: HP-5 ms UI (30m x 250 μm×0.25 μm); Inlet temp: 250° C.; Split ratio: 75:1; Oven temp: 120° C., hold time 1 min; Ramp 1: 40° C./min to 300° C., hold time 4 min; Detector temperature: 310° C.; Column flow: 2 mL/min; Air flow: 300 mL/min; $H_2$ flow: 40 mL/min; Make up flow (He): 25 mL/min; Source temp: 230° C.

MS Methods

Method 1. Data acquired on either a Waters QDA or Waters SQD instrument after a 4-6 minute run through a UPLC column using buffer.

Prep HPLC Methods

See LCMS methods section for solvent conditions.

Method 1. Instruments: Gilson Semi Preparative HPLC System—321 Pump/171 Diode Array Detector/GX-271 Liquid Handler; Column: Phenomenex Gemini-NX C18 5 micron 30×100 mm; Gradient 12.5 min, solvent B2 in A6 (%) varies on individual run basis (see exemplified procedures for details).

Method 2. Instruments: Waters 2767 Auto purification; Column: X Bridge Shield 10 micron 19×250 mm; Gradient 20 min, solvent B2 in A2 (%) varies on individual run basis (see exemplified procedures for details).

Method 3. Instruments: Agilent Technologies 1260 Infinity II Series LC/6125 Quadrupole MSD; Column: Waters XBridge C8 5 micron 19×150 mm; Gradient [time (min)/solvent B2 in A5 (%)]:0.0/10, 15/95, 18/95, 19/10, 21/10.

Abbreviations aq=aqueous

DAST=(diethylamino)sulfur trifluoride dba=dibenzylideneacetone

DCM=dichloromethane

Dess-Martin=1,1,1-tris(acetyloxy)-1,1-dihydro-1,2-benziodoxol-3-(1H)-one

DIPEA=N,N-diisopropylethylamine

DMF=N,N-dimethylformamide

DMF-DMA=N,N-dimethylformamide dimethyl acetal

DMSO=dimethylsulfoxide dppf=1,1'-ferrocenediyl-bis(diphenylphosphine)

ES=electrospray

EtOAc=ethyl acetate

EtOH=ethanol h=hour(s)

HATU=N-[(Dimethylamino)-1H-1,2,3-triazolo-[4,5-b]pyridin-1-ylmethylene]-N-methylmethanaminium hexafluorophosphate N-oxide IPA=i-propyl alcohol L=litre LC=liquid chromatography LCMS=liquid chromatography mass spectrometry MeCN=acetonitrile MeOH=methanol min=minute(s)

MS=mass spectrometry

NMP=1-methyl-2-pyrrolidinone

NMR=nuclear magnetic resonance

Pet-ether=petroleum ether pin=pinacolato

RT=room temperature

RuPhos=2-dicyclohexylphosphino-2',6'-diisopropoxybiphenyl

T3P=2,4,6-Tripropyl-1,3,5,2,4,6-trioxatriphosphorinane-2,4,6-trioxide

TFA=trifluoroacetic acid

THF=tetrahydrofuran

Prefixes n-, s-, i-, t- and tert- have their usual meanings: normal, secondary, iso, and tertiary.

Synthesis of Intermediates

Preparation of Substituted Fluoropyridine Intermediates

Intermediate Route 1, Exemplified by the Preparation of Intermediate 1, 2-fluoro-4-(3-fluoro-5-(trifluoromethyl)benzyl)pyridine

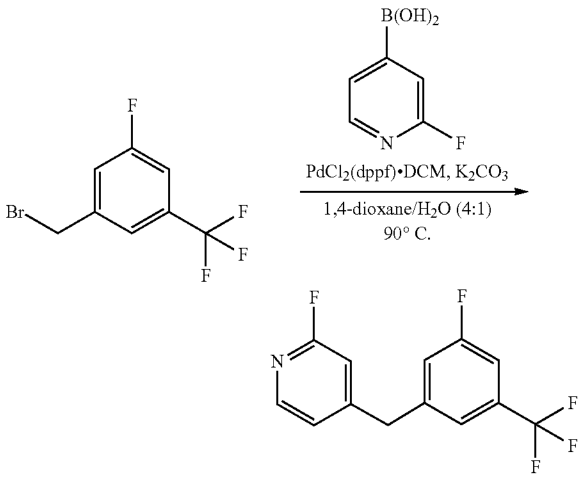

$PdCl_2$(dppf)·DCM (284 mg, 0.38 mmol) was added to a degassed solution of (2-fluoropyridin-4-yl)boronic acid (1.3 g, 7.77 mmol), potassium carbonate (3.2 g, 22.3 mmol) and 1-(bromomethyl)-3-fluoro-5-(trifluoromethyl)benzene (1.3 g, 9.30 mmol) in 1,4-dioxane (20 mL)/water (5 mL) and the resultant reaction mixture heated at 90° C. for 1 h. The reaction mixture was partitioned between water (70 mL) and EtOAc (100 mL). The organic layer was separated, washed with brine (50 mL), dried ($Na_2SO_4$) and the solvent removed in vacuo. The residue was purified by gradient flash column chromatography eluting with 0-30% EtOAc in pet-ether to afford 2-fluoro-4-(3-fluoro-5-(trifluoromethyl)benzyl)pyridine as a brown oil (1.8 g, 86%). Data in table 2.

Intermediate Route 2, Exemplified by the Preparation of Intermediate 2, 4-fluoro-2-(3-fluoro-5-(trifluoromethyl)benzyl)pyridine

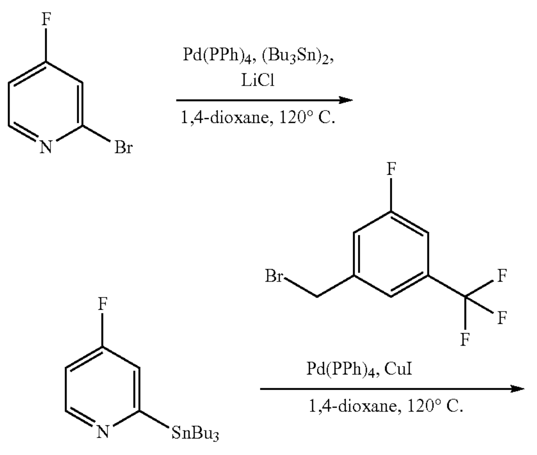

-continued

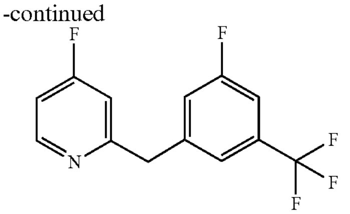

Step 1. A solution of 2-bromo-4-fluoropyridine (4.0 g, 22.7 mmol) in 1,4-dioxane (60 mL) was degassed with argon for 10 min and bis(tributyltin) (17.3 mL, 34.0 mmol), LiCl (2.88 g, 68.1 mmol) and $Pd(PPh_3)_4$ (1.31 g, 1.13 mmol) were added. The reaction mixture was heated at 120° C. for 16 h. The reaction was quenched with water (100 mL) and the aqueous layer was extracted with EtOAc (2×100 mL). The organic layers were combined, dried ($Na_2SO_4$) and the solvent removed in vacuo to afford 4-fluoro-2-(tributylstannyl)pyridine as a yellow liquid (14.3 g, crude). The crude product was used in the next step without further purification. MS (Method 1): m/z 388 (ES+)

Step 2. 1-(Bromomethyl)-3-fluoro-5-(trifluoromethyl)benzene (1.33 g, 5.18 mmol) was added to a solution of 4-fluoro-2-(tributylstannyl)pyridine (14.3 g, 5.18 mmol) in 1,4-dioxane (30 mL). The reaction mixture was degassed with argon for 10 min and CuI (98 mg, 0.51 mmol), $Pd(PPh_3)_4$ (299 mg, 0.26 mmol) were added. The reaction mixture was heated at 120° C. for 16 h. The reaction was quenched with water (30 mL) and the aqueous layer was extracted EtOAc (2×100 mL). The combined organic layers were washed with brine, dried ($Na_2SO_4$) and the solvent removed in vacuo. The residue was purified by gradient flash column chromatography eluting with 5-10% EtOAc in hexane to afford 4-fluoro-2-(3-fluoro-5-(trifluoromethyl)benzyl)pyridine as a light yellow liquid (400 mg, 6.4% over two steps).

Data in table 2.

Intermediate Route 3, Exemplified by the Preparation of Intermediate 6, 2-fluoro-6-(3-fluoro-5-(trifluoromethyl)benzyl)pyridine

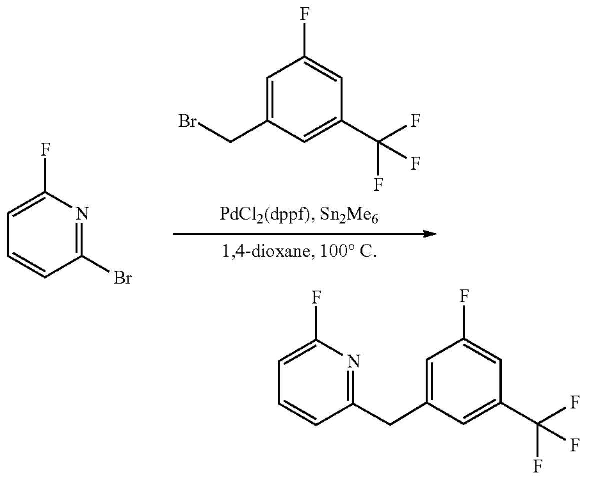

$Sn_2Me_6$ (600 mg, 1.94 mmol) was added to a stirred solution of 2-bromo-6-fluoropyridine (340 mg, 1.94 mmol) in 1,4-Dioxane (20 mL) at RT followed by the addition of $PdCl_2$(dppf) (150 mg, 0.19 mmol) and the reaction mixture was heated at 100° C. for 15 hr. 1-(Bromomethyl)-3-fluoro-5-(trifluoromethyl)benzene (500 mg, 1.94 mmol) and $PdCl_2$ (dppf) (150 mg, 0.19 mmol) were then added and the reaction mixture heated at 100° C. for 15 h. The solvent was removed in vacuo and the residue purified by gradient flash column chromatography eluting with 0-5% EtOAc in pet-ether gradient to afford 2-fluoro-6-(3-fluoro-5-(trifluoromethyl)benzyl)pyridine as a white semi solid (400 mg, 75%). Data in table 2.

Preparation of Substituted Hydrazineyl Intermediates

Intermediate Route 4, Exemplified by the Preparation of Intermediate 3, 4-(3-fluoro-5-(trifluoromethyl)benzyl)-2-hydrazineylpyridine

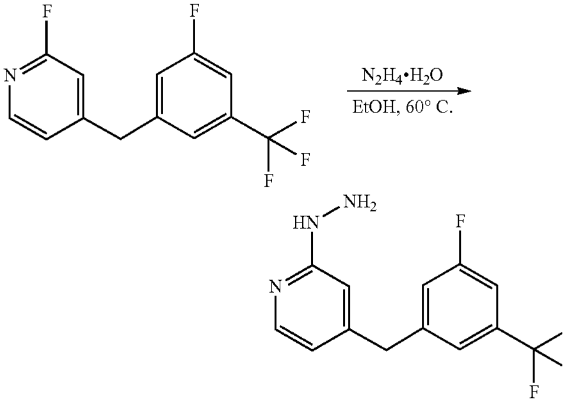

Hydrazine hydrate (0.17 mL, 3.52 mmol) was added to a stirred solution of 2-fluoro-4-(3-fluoro-5-(trifluoromethyl)benzyl)pyridine (Intermediate 1, 300 mg, 1.17 mmol) in EtOH (10 mL) and the resultant reaction mixture was heated at 60° C. for 16 h. The solvent was removed in vacuo and the residue partitioned between water (50 mL) and EtOAc (50 mL). The organic layer was separated, washed with brine (50 mL), dried ($Na_2SO_4$) and the solvent removed in vacuo to afford 4-(3-fluoro-5-(trifluoromethyl)benzyl)-2-hydrazineylpyridine as a brown oil (350 mg, 100%). Data in table 2.

Intermediate 13, 4-(3-(difluoromethyl)-5-fluorobenzyl)-2-hydrazineylpyridine

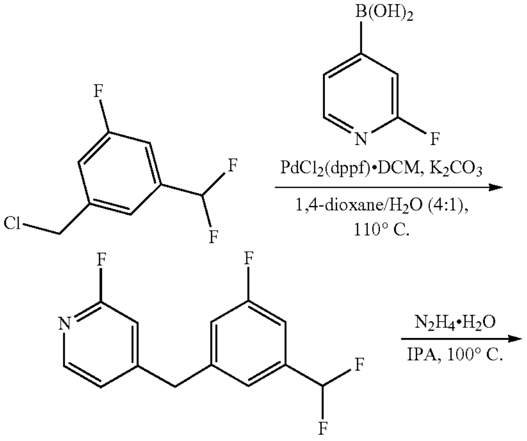

-continued

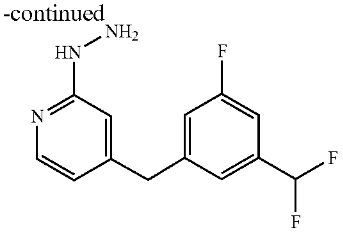

The title compound (110 mg, crude) was prepared in two steps from (2-fluoropyridin-4-yl)boronic acid (145 mg, 1.03 mmol), 1-(chloromethyl)-3-(difluoromethyl)-5-fluorobenzene (Intermediate 12, 200 mg, 1.03 mmol), $PdCl_2$(dppf)·DCM (84 mg, 0.103 mmol) and $K_2CO_3$ (426 mg, 3.09 mmol) in 1,4-dioxane (8 mL)/water (2 mL) heated at 110° C. for 16 h; and hydrazine hydrate (0.5 mL, 9.77 mmol) in IPA (10 mL) heated at 100° C. for 48 h using the methods of Intermediate 1 and Intermediate 3. After completion of step 2, the title compound was isolated as a yellow gum by partitioning between EtOAc (10 mL) and water (10 mL). The aqueous layer was extracted with EtOAc (10 mL). The combined organic layers were washed with brine solution (10 mL), dried ($Na_2SO_4$) and the solvent removed in vacuo. The crude product was used in the next step without further purification. Data in table 2.

Intermediate Route 5, Exemplified by the Preparation of Intermediate 14, 2-(3-fluoro-5-(trifluoromethyl)benzyl)-4-hydrazineylpyridine

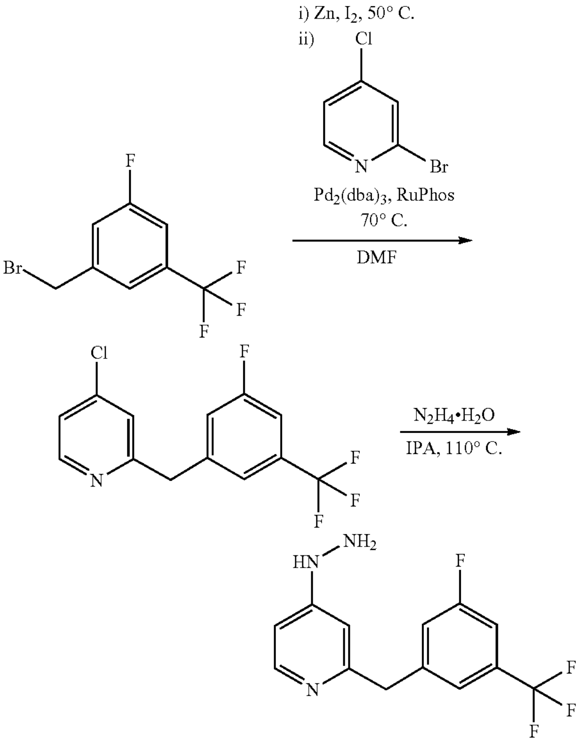

Step 1. A pinch of iodine was added to a stirred solution of activated zinc (35 g, 583 mmol) in DMF (300 mL) and the solution heated at 50° C. for 5 min followed by the addition of 1-(bromomethyl)-3-fluoro-5-(trifluoromethyl)benzene (32 g, 124 mmol) in DMF (50 mL). The reaction mixture was heated at 50° C. for 1 h and then allowed to cool to RT. The residual zinc was allowed to settle and the supernatant pale green DMF layer was transferred via cannula to a degassed suspension of 2-bromo-4-chloropyridine (16 g, 83.3 mmol) and RuPhos (2.3 g, 4.99 mmol) in DMF (50 mL) followed by the addition of tris(dibenzylideneacetone)dipalladium(0) (3.8 g, 4.16 mmol). The reaction mixture was heated at 70° C. for 16 h and then filtered through Celite and washed with EtOAc (600 mL). The filtrate was washed with brine (3×300 mL). The organic layer was separated, dried ($Na_2SO_4$) and the solvent removed in vacuo. The residue was purified by gradient flash column chromatography eluting with 0-5% EtOAc in pet-ether to afford 4-chloro-2-(3-fluoro-5-(trifluoromethyl)benzyl)pyridine as a yellow semi solid (8 g, 33%).

LCMS (Method 1): m/z 290.1 (ES+), at 2.65 min.

$^1H$ NMR: (400 MHz, DMSO-$d_6$) δ: 8.49 (d, J=5.2 Hz, 1H), 7.83-7.79 (m, 1H), 7.61-7.41 (m, 4H), 4.23 (s, 2H).

Step 2. Hydrazine hydrate (20 g, 415 mmol) was added to a stirred solution of 4-chloro-2-(3-fluoro-5-(trifluoromethyl)benzyl)pyridine (8 g, 27.68 mmol) in IPA (100 mL) in a sealed tube and the reaction mixture was heated at 110° C. for 72 h. The solvent was removed in vacuo and the residue partitioned between water (200 mL) and EtOAc (200 mL). The organic layer was separated, washed with brine (200 mL), dried ($Na_2SO_4$) and the solvent removed in vacuo to afford 2-(3-fluoro-5-(trifluoromethyl)benzyl)-4-hydrazineylpyridine as a yellow gum (5 g, 63%). Data in table 2.

Preparation of Substituted Azole Carboxylic Acid Intermediates

Intermediate Route 6, Exemplified by the Preparation of Intermediate 4, 1-(2-(3-fluoro-5-(trifluoromethyl)benzyl)pyridin-4-yl)-3-methyl-1H-pyrazole-4-carboxylic acid

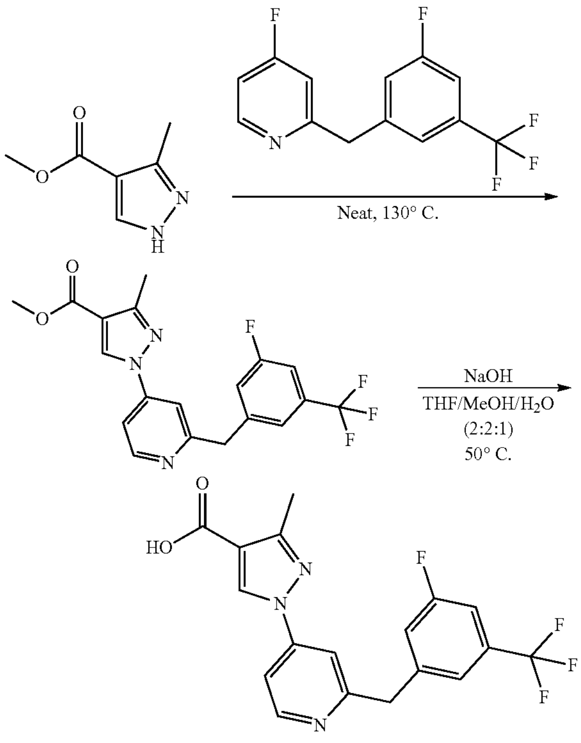

Step 1. A mixture of methyl 3-methyl-1H-pyrazole-4-carboxylate (150 mg, 1.07 mmol) and 4-fluoro-2-(3-fluoro-5-(trifluoromethyl)benzyl)pyridine (Intermediate 2, 292 mg, 1.07 mmol) was heated at 130° C. for 16 h to afford methyl 1-(2-(3-fluoro-5-(trifluoromethyl)benzyl)pyridin-4-yl)-3-methyl-1H-pyrazole-4-carboxylate as an off white solid (400 mg, 95%). LCMS (Method 4): m/z 394.3 (ES+), at 2.38 min.

Step 2. NaOH (83 mg, 2.03 mmol) in water (1 mL) was added to a solution of methyl 1-(2-(3-fluoro-5-(trifluoromethyl)benzyl)pyridin-4-yl)-3-methyl-1H-pyrazole-4-carboxylate (400 mg, 1.02 mmol) in THF (2 mL) and MeOH (1 mL). The reaction mixture was heated at 50° C. for 2 h. The solvent was removed in vacuo and the residue was treated with water (25 mL). The solid obtained was filtered and dried in vacuo to afford 1-(2-(3-fluoro-5-(trifluoromethyl)benzyl)pyridin-4-yl)-3-methyl-1H-pyrazole-4-carboxylic acid as off white solid (400 mg, 95%). Data in table 2.

Intermediate Route 7, Exemplified by the Preparation of Intermediate 5, 1-(4-(3-fluoro-5-(trifluoromethyl)benzyl)pyridin-2-yl)-1H-pyrazole-3-carboxylic acid

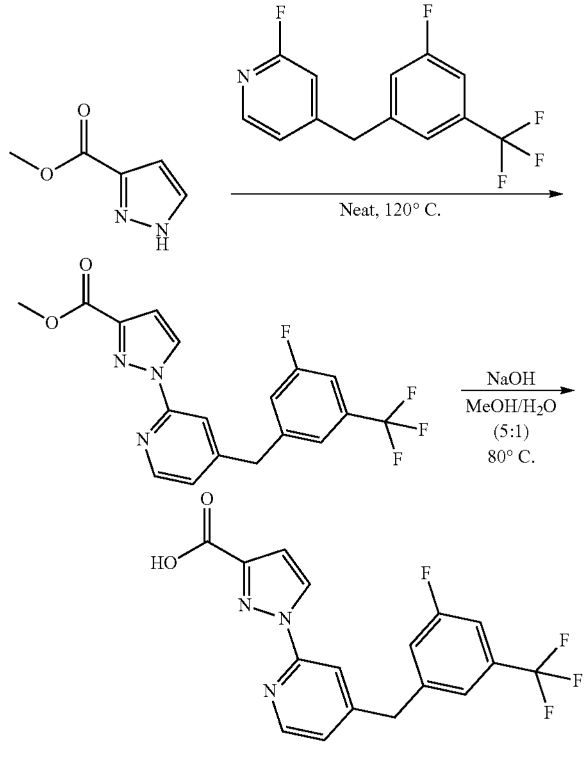

Step 1. A mixture of methyl 1H-pyrazole-3-carboxylate (100 mg, 0.79 mmol) and 2-fluoro-4-(3-fluoro-5-(trifluoromethyl)benzyl)pyridine (Intermediate 1, 217 mg, 0.79 mmol) was heated at 120° C. for 48 h. The reaction mixture was diluted with 5% MeOH in DCM and the solvent removed in vacuo to afford methyl 1-(4-(3-fluoro-5-(trifluoromethyl)benzyl)pyridin-2-yl)-1H-pyrazole-3-carboxylate as a brown semi-solid (220 mg, 73%).

LCMS (Method 4): m/z 378.3 (ES+), at 2.36 min.

Step 2. A solution of sodium hydroxide (63 mg, 1.58 mmol) in water (2 mL) was added to a solution of methyl 1-(4-(3-fluoro-5-(trifluoromethyl)benzyl)pyridin-2-yl)-1H-pyrazole-3-carboxylate (200 mg, 0.52 mmol) in MeOH (10 mL) and the reaction mixture was heated at 80° C. for 16 h. The solvent was removed in vacuo and the residue was acidified with aq $NaHSO_4$ solution (20 mL). The aqueous layer was extracted with EtOAc (3×30 mL). The combined organic layers were dried ($Na_2SO_4$) and the solvent removed in vacuo. The residue was washed with heptane (10 mL) and $Et_2O$ (10 ml) to afford 1-(4-(3-fluoro-5-(trifluoromethyl)benzyl)pyridin-2-yl)-1H-pyrazole-3-carboxylic acid as an off white solid (190 mg, 99%). Data in table 2.

Intermediate 7, 1-(4-(3-fluoro-5-(trifluoromethyl)benzyl)pyridin-2-yl)-4-methyl-1H-pyrazole-3-carboxylic acid

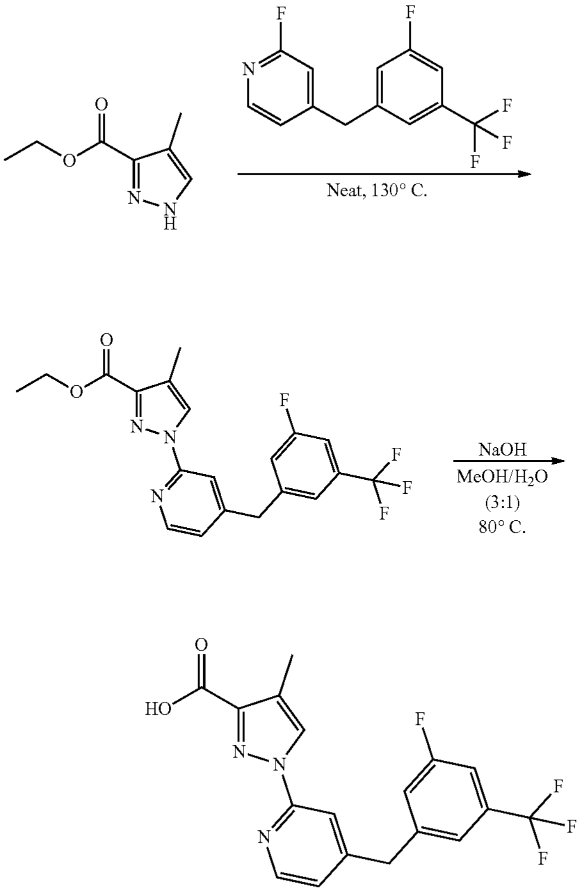

The title compound (180 mg, 68%) was prepared in two steps from ethyl 4-methyl-1H-pyrazole-3-carboxylate (100 mg, 0.64 mmol) and 2-fluoro-4-(3-fluoro-5-(trifluoromethyl)benzyl)pyridine (Intermediate 1, 177 mg, 0.64 mmol) heated at 130° C. for 16 h; and a solution of NaOH (73 mg, 1.82 mmol) in water (1.5 mL) in MeOH (5 mL) heated at 80° C. for 2 h using the methods of Intermediate 5. After completion of step 2, the title compound was isolated as a white solid by acidification with aq $NaHSO_4$ solution (20 mL) and extraction of the aqueous layer with EtOAc (3×30 mL). The combined organic layers were dried ($Na_2SO_4$) and the solvent removed in vacuo. Data in table 2.

Intermediate 8, 1-(2-(3-fluoro-5-(trifluoromethyl)benzyl)pyridin-4-yl)-1H-pyrazole-3-carboxylic acid

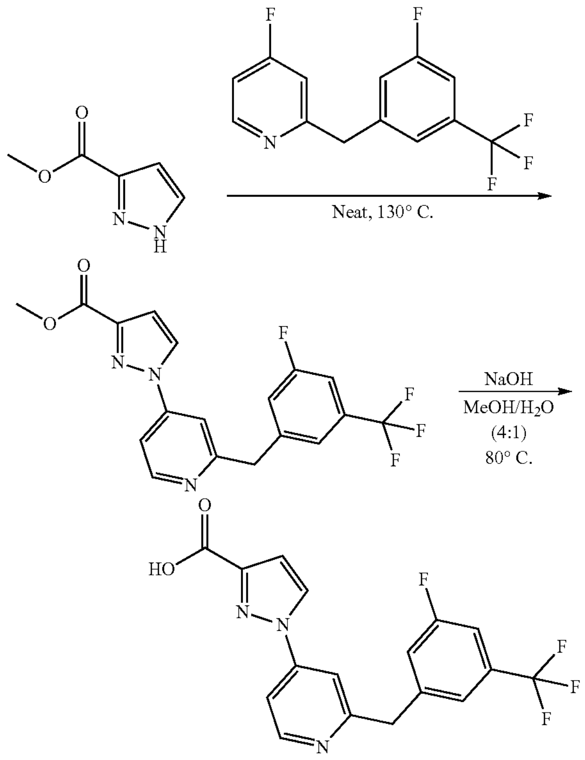

The title compound (200 mg, 69%) was prepared in two steps from methyl 1H-pyrazole-3-carboxylate (100 mg, 0.79 mmol) and 4-fluoro-2-(3-fluoro-5-(trifluoromethyl)benzyl)pyridine (Intermediate 2, 217 mg, 0.79 mmol) heated at 130° C. for 16 h; and a solution of NaOH (153 mg, 3.81 mmol) in water (1.5 mL) in MeOH (6 mL) heated at 80° C. for 4 h using the methods of Intermediate 5. After completion of step 2, the title compound was isolated as a pink solid by acidification with aq $NaHSO_4$ solution (20 mL) and extraction of the aqueous layer with EtOAc (3×30 mL). The combined organic layers were dried ($Na_2SO_4$) and the solvent removed in vacuo. Data in table 2.

Intermediate Route 8, Exemplified by the Preparation of Intermediate 9, 1-(4-(3-fluoro-5-(trifluoromethyl)benzyl)pyridin-2-yl)-5-methyl-1H-pyrazole-3-carboxylic acid

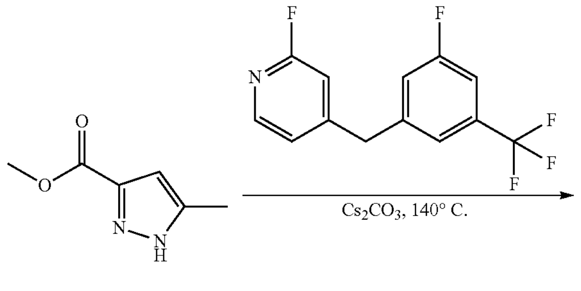

-continued

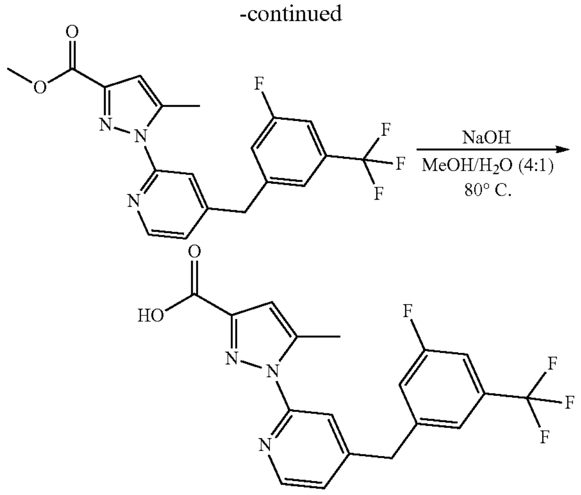

Step 1. A mixture of methyl 5-methyl-1H-pyrazole-3-carboxylate (100 mg, 0.71 mmol), 2-fluoro-4-(3-fluoro-5-(trifluoromethyl)benzyl)pyridine (Intermediate 1, 195 mg, 0.71 mmol) and cesium carbonate (232 mg, 0.71 mmol) was heated at 140° C. for 16 h. The reaction mixture was diluted with 10% MeOH in DCM, filtered and the solvent removed in vacuo to afford methyl 1-(4-(3-fluoro-5-(trifluoromethyl)benzyl)pyridin-2-yl)-5-methyl-1H-pyrazole-3-carboxylate as a yellow solid (130 mg, crude). The crude product was used in the next step without further purification.

LCMS (Method 4): m/z 394.0 (ES+), at 2.32 min.

Step 2. The title compound (100 mg, crude) was prepared from methyl 1-(4-(3-fluoro-5-(trifluoromethyl)benzyl)pyridin-2-yl)-5-methyl-1H-pyrazole-3-carboxylate (100 mg, 0.33 mmol) in MeOH (4 mL) and a solution of NaOH (53 mg, 1.32 mmol) in water (1 mL) heated at 80° C. for 16 h using the methods of Intermediate 5, step 2. The title compound was isolated as a yellow semi-solid by acidification with aq $NaHSO_4$ solution (20 mL) and extraction of the aqueous layer with EtOAc (2×30 mL). The combined organic layers were dried ($Na_2SO_4$) and the solvent removed in vacuo. Data in table 2.

Intermediate Route 9, Exemplified by the Preparation of Intermediate 15, 1-(4-(3-(difluoromethyl)-5-fluorobenzyl)pyridin-2-yl)-3-methyl-1H-pyrazole-4-carboxylic acid

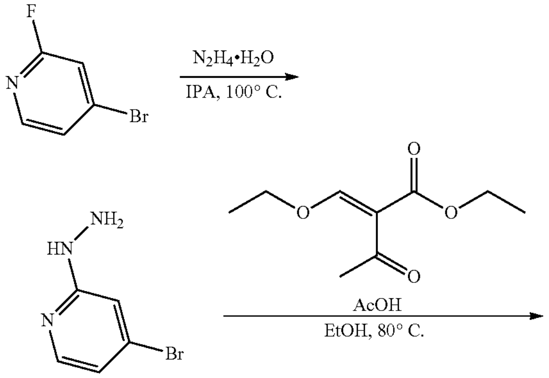

-continued

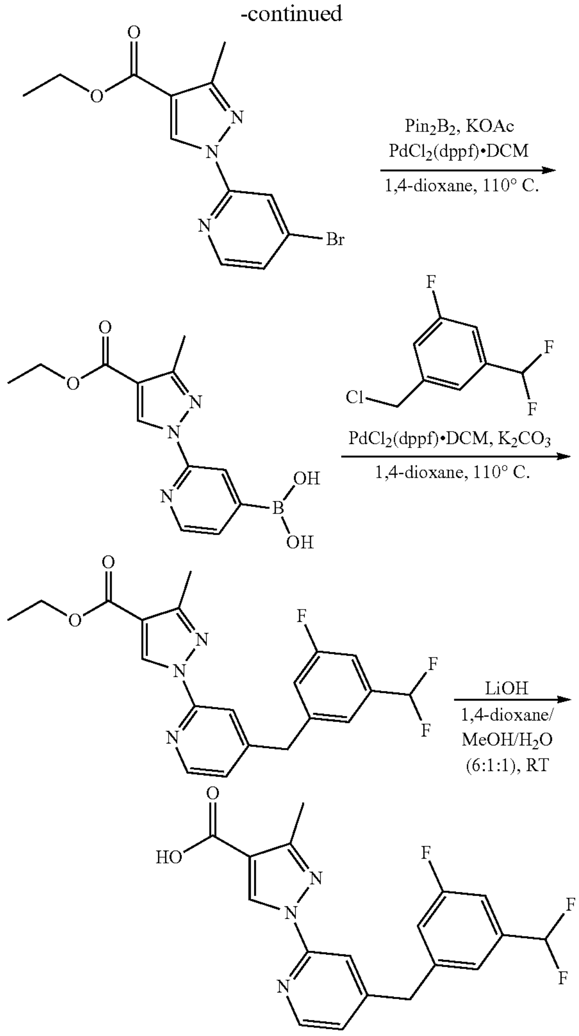

Step 1. Hydrazine hydrate (5.69 g, 114 mmol) was added to a stirred solution of 4-bromo-2-fluoropyridine (2 g, 11.4 mmol) in IPA (100 mL) at RT and the resultant reaction mixture was heated at 100° C. for 16 h. The solvent was removed in vacuo. The residue was partitioned between water (100 mL) and EtOAc (100 mL). The organic layer was separated, dried ($Na_2SO_4$) and the solvent removed in vacuo to afford 4-bromo-2-hydrazineylpyridine as a brown solid (1.5 g, 70%).

LCMS (Method 1): m/z 187.9 (ES-), at 0.41 min.

$^1H$ NMR: (400 MHz, DMSO-$d_6$) δ: 7.85 (d, J=5.2 Hz, 1H), 7.72 (s, 1H), 6.92 (d, J=1.6 Hz, 1H), 6.71 (dd, J=5.4, 2.0 Hz, 1H), 4.21 (s, 2H).

Step 2. 4-bromo-2-hydrazineylpyridine (520 mg, 2.77 mmol) and acetic acid (0.053 mL, 0.922 mmol) were added to a solution of ethyl 2-(ethoxymethylene)-3-oxobutanoate (343 mg, 1.84 mmol) in EtOH (20 mL) at RT, and the reaction was further heated at 80° C. for 15 h. The solvent was removed in vacuo. The residue was triturated with 10% aq $NaHCO_3$ solution (15 mL), filtered and dried in vacuo to afford ethyl 1-(4-bromopyridin-2-yl)-3-methyl-1H-pyrazole-4-carboxylate as an off-white solid (300 mg, 35%).

LCMS (Method 1): m/z 310.0 (ES+), at 2.64 min.

$^1H$ NMR: (400 MHz, DMSO-$d_6$) δ: 8.47 (d, J=5.2 Hz, 1H), 8.10 (s, 1H), 8.07 (d, J=1.6 Hz, 1H), 7.78 (dd, J=5.4, 1.6 Hz, 1H), 4.27 (q, J=7.2 Hz, 2H), 4.25 (s, 3H), 1.31 (t, J=6.8 Hz, 3H).

Step 3. Potassium acetate (285 mg, 2.90 mmol) and $pin_2B_2$ (246 mg, 0.97 mmol) were added to a stirred solution of ethyl 1-(4-bromopyridin-2-yl)-3-methyl-1H-pyrazole-4-carboxylate (300 mg, 0.97 mmol) in 1,4-dioxane (5 mL) followed by the addition of $PdCl_2$(dppf)·DCM (39.5 mg, 0.048 mmol) and the resultant reaction mixture was heated at 110° C. for 16 h. The solvent was removed in vacuo to afford (2-(4-(ethoxycarbonyl)-3-methyl-1H-pyrazol-1-yl)pyridin-4-yl)boronic acid as a brown semi solid (300 mg, crude). The crude product was used in the next step without further purification.

LCMS (Method 11): m/z 276.1 (ES+), at 1.75 min.

Step 4. $K_2CO_3$ (160 mg, 1.156 mmol) and $PdCl_2$(dppf)·DCM (31.5 mg, 0.039 mmol) were added to a solution of (2-(4-(ethoxycarbonyl)-3-methyl-1H-pyrazol-1-yl)pyridin-4-yl)boronic acid (254 mg, 0.925 mmol) and 1-(chloromethyl)-3-(difluoromethyl)-5-fluorobenzene (Intermediate 12, 150 mg, 0.771 mmol) in 1,4-dioxane (10 mL) at RT and the resultant reaction mixture was heated at 110° C. for 15 h. The reaction mixture was partitioned between water (10 mL) and EtOAc (10 mL). The organic layer was separated, dried ($Na_2SO_4$) and the solvent removed in vacuo. The residue was purified by gradient flash column chromatography eluting with 0-30% EtOAc in pet-ether to afford ethyl 1-(4-(3-(difluoromethyl)-5-fluorobenzyl)pyridin-2-yl)-3-methyl-1H-pyrazole-4-carboxylate as an off-white solid (60 mg, 17%).

LCMS (Method 11): m/z 390.0 (ES+), at 2.93 min.

$^1$H NMR: (400 MHz, DMSO-$d_6$) δ: 8.48 (d, J=5.1 Hz, 1H), 8.06 (d, J=5.7 Hz, 1H), 7.77 (s, 1H), 7.46-7.41 (m, 3H), 7.32 (d, J=8.4 Hz, 1H), 7.03 (t, J=55.5 Hz, 1H), 4.27-4.25 (m, 2H), 4.20 (s, 2H), 2.81 (s, 3H), 1.38-1.28 (m, 3H).

Step 5. LiOH (11.07 mg, 0.462 mmol), water (0.5 mL) and MeOH (0.5 mL) were added to a solution of ethyl 1-(4-(3-(difluoromethyl)-5-fluorobenzyl)pyridin-2-yl)-3-methyl-1H-pyrazole-4-carboxylate (60 mg, 0.15 mmol) in 1,4-dioxane (3 mL) at RT and the resultant reaction mixture was stirred at RT for 15 h. The solvent was removed in vacuo. The resdiue was acidified with 1.5 N HCl (5 mL) to pH ~6 and the aqueous layer extracted with EtOAc (15 mL). The organic layer was separated, dried ($Na_2SO_4$) and the solvent removed in vacuo to afford 1-(4-(3-(difluoromethyl)-5-fluorobenzyl)pyridin-2-yl)-3-methyl-1H-pyrazole-4-carboxylic acid as an off-white solid (40 mg, 72%). Data in table 2.

Intermediate 16, 1-(4-(3-(difluoromethyl)-5-fluorobenzyl)pyridin-2-yl)-1H-pyrazole-3-carboxylic acid

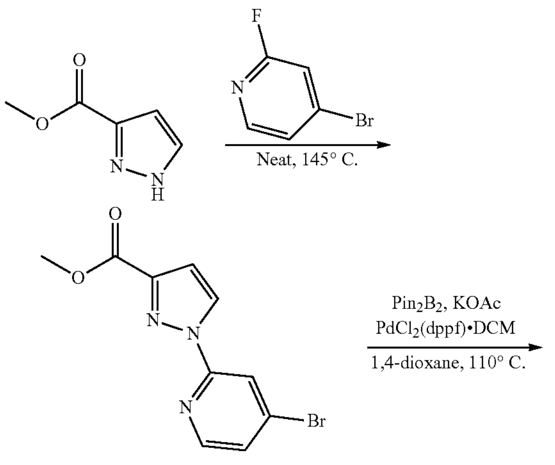

-continued

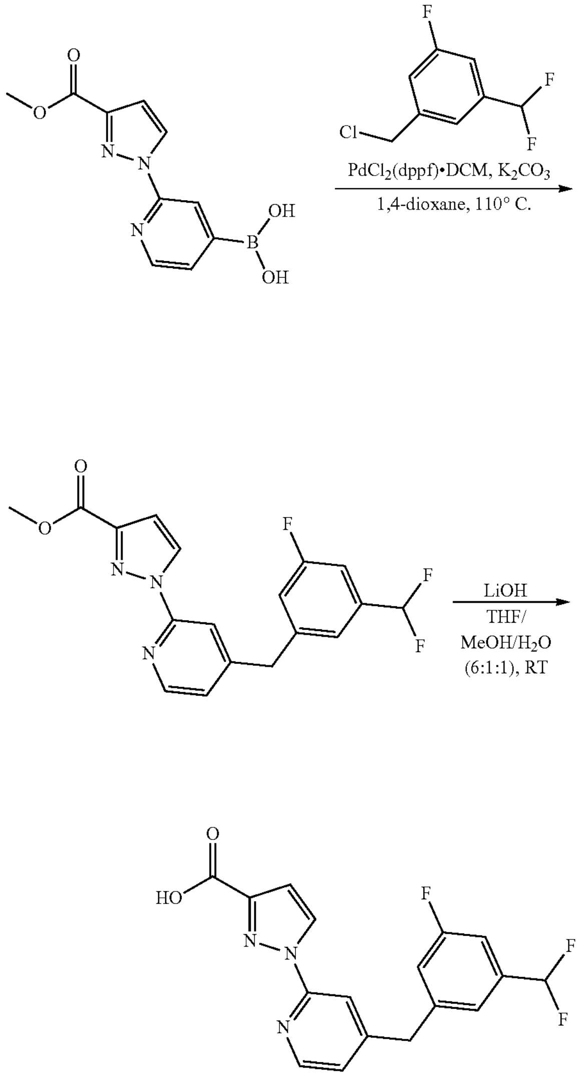

The title compound (60 mg, 6%) was prepared in four steps from 4-bromo-2-fluoropyridine (1.5 g, 8.52 mmol) and methyl 1H-pyrazole-3-carboxylate (1.6 g, 12.78 mmol) heated at 145° C. for 16 h; potassium acetate (261 mg, 2.66 mmol), $pin_2B_2$ (248 mg, 0.97 mmol) and $PdCl_2$(dppf)·DCM (36.2 mg, 0.04 mol) in 1,4-dioxane (20 mL) heated at 100° C. for 16 h; $K_2CO_3$ (213 mg, 1.54 mmol), $PdCl_2$(dppf)·DCM (21 mg, 0.026 mmol) and 1-(chloromethyl)-3-(difluoromethyl)-5-fluorobenzene (Intermediate 12, 100 mg, 0.51 mmol) in 1,4-dioxane (10 mL) heated at 110° C. for 15 h; and a solution of NaOH (26.6 mg, 0.664 mmol) in water (0.5 mL) in THF (1 mL) and MeOH (1 mL) stirred at RT for 1 h using the methods of Intermediate 4, step 1, Intermediate 15, steps 3 and 4 and Intermediate 4, step 2 After completion of step 4, the title compound was isolated as an off-white solid by acidification with 1.5 N HCl (5 mL) to pH ~6 and extraction of the aqueous layer with EtOAc (15 mL). The organic layer was separated, dried ($Na_2SO_4$) and the solvent removed in vacuo. Data in table 2.

Intermediate Route 10, Exemplified by the Preparation of Intermediate 17, 1-(4-(3-fluoro-5-(trifluoromethyl)benzyl)pyridin-2-yl)-5-(hydroxymethyl)-3-methyl-1H-pyrazole-4-carboxylic acid

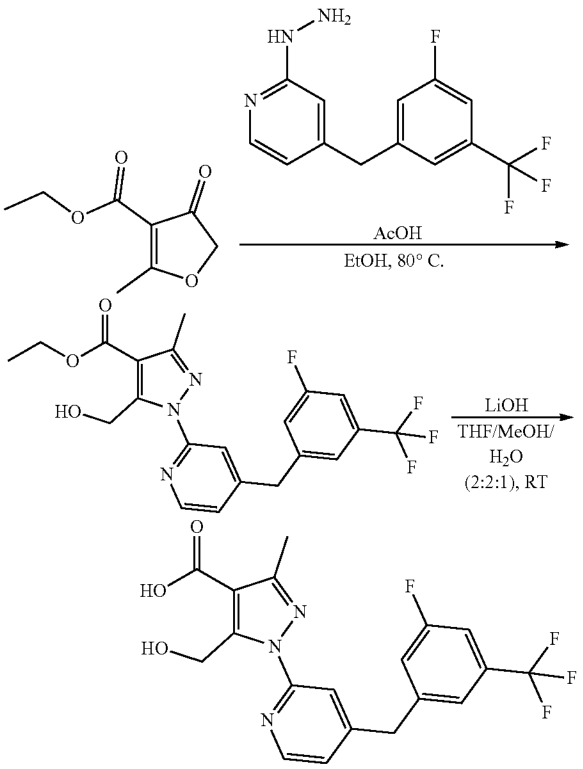

Step 1. 4-(3-Fluoro-5-(trifluoromethyl)benzyl)-2-hydrazineylpyridine (Intermediate 3, 4.69 g, 16.5 mmol) was added to a stirred solution of ethyl 2-methyl-4-oxo-4,5-dihydrofuran-3-carboxylate (Intermediate 10, 2.8 g, 16.5 mmol) in ethanol (50 mL) at RT followed by the addition of catalytic amount of acetic acid (0.094 mL, 1.65 mmol) and the resultant reaction mixture was heated at 80° C. for 16 h. On cooling, the solid which had come out of solution was filtered, rinsed with EtOH (2×10 mL) and dried in vacuo to afford ethyl 1-(4-(3-fluoro-5-(trifluoromethyl)benzyl)pyridin-2-yl)-5-(hydroxymethyl)-3-methyl-1H-pyrazole-4-carboxylate as a white solid (1.95 g, 27%).

LCMS (Method 1): m/z 438.0 (ES+), at 2.80 min.

$^1H$ NMR: (400 MHz, DMSO-$d_6$) δ: 8.48 (d, J=7.2 Hz, 1H), 7.84 (s, 1H), 7.67 (s, 1H), 7.61-7.59 (m, 2H), 7.43 (d, J=6.4 Hz, 1H), 5.27 (t, J=9.2 Hz, 1H), 5.01 (d, J=8.8 Hz, 2H), 4.29-4.27 (m, 4H), 2.42 (s, 3H), 1.32 (t, J=9.6 Hz, 3H).

Step 2. Lithium hydroxide monohydrate (1.07 g, 44.5 mmol) was added to a stirred solution of ethyl 1-(4-(3-fluoro-5-(trifluoromethyl)benzyl)pyridin-2-yl)-5-(hydroxymethyl)-3-methyl-1H-pyrazole-4-carboxylate (1.95 g, 4.45 mmol) in THF (10 mL), MeOH (10 mL) and water (5 mL) and the resultant reaction mixture was stirred at RT for 16 h. The solvent was removed in vacuo. The residue obtained was dissolved in water (30 mL) and acidified with 2 N HCl to pH ~2 and the aqueous layer extracted with EtOAc (4×50 mL). The combined organic layers were separated, washed with brine (30 mL), dried ($Na_2SO_4$) and the solvent removed in vacuo to afford 1-(4-(3-fluoro-5-(trifluoromethyl)benzyl)pyridin-2-yl)-5-(hydroxymethyl)-3-methyl-1H-pyrazole-4-carboxylic acid as a white solid (1.81 g, 99%). Data in table 2.

Intermediate 18, 1-(2-(3-fluoro-5-(trifluoromethyl)benzyl)pyridin-4-yl)-5-(hydroxymethyl)-3-methyl-1H-pyrazole-4-carboxylic acid

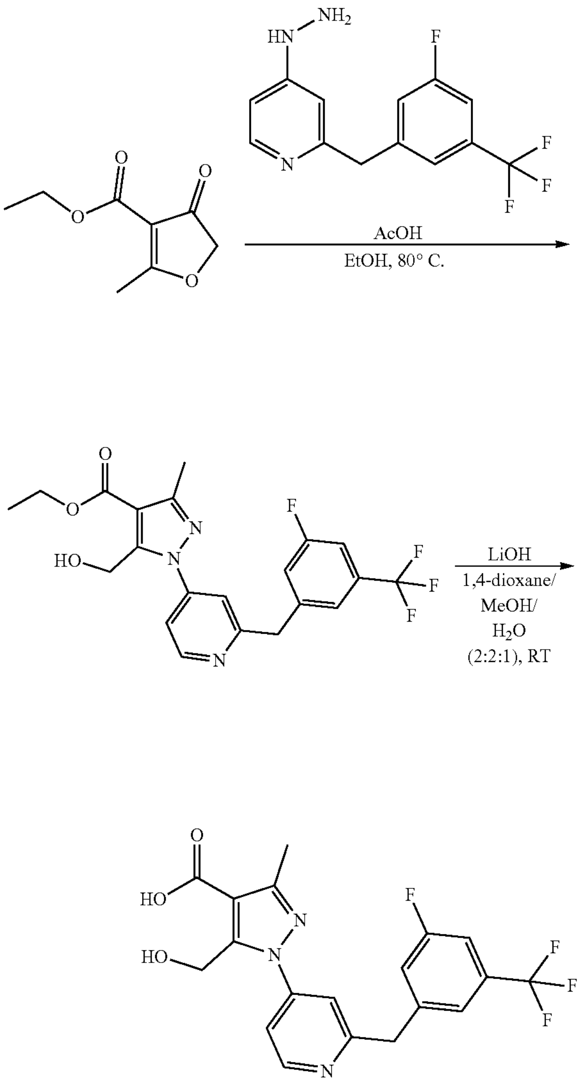

The title compound (230 mg, 26%) was prepared in two steps from 2-(3-fluoro-5-(trifluoromethyl)benzyl)-4-hydrazineylpyridine (Intermediate 14, 600 mg, 2.10 mmol), ethyl 2-methyl-4-oxo-4,5-dihydrofuran-3-carboxylate (Intermediate 10, 430 mg, 2.52 mmol) and acetic acid (0.120 mL, 2.10 mmol) in EtOH (20 mL) heated at 80° C. for 16 h; and LiOH (109 mg, 4.57 mmol), water (1 mL), MeOH (1 mL) and 1,4-dioxane (20 mL) stirred at RT for 16 h using the methods of Intermediate 17, step 1 and Intermediate 15, step 5. After completion of step 2, the title compound was isolated as a pale yellow solid by removal of the solvent in vacuo, acidification with 1.5 N HCl (5 mL) to pH ~6 and partitioning between water (10 mL) and EtOAc (15 mL). The organic layer was separated, dried ($Na_2SO_4$) and the solvent removed in vacuo. Data in table 2.

Intermediate 19, 1-(4-(3-(difluoromethyl)-5-fluorobenzyl)pyridin-2-yl)-5-(hydroxymethyl)-3-methyl-1H-pyrazole-4-carboxylic acid

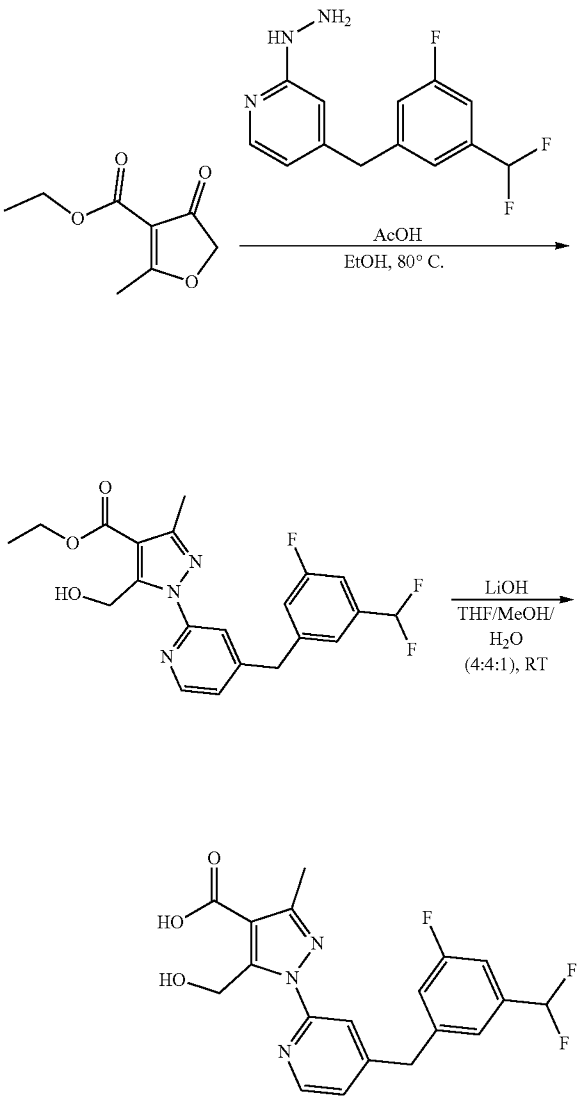

The title compound (1.1 g, 76%) was prepared in two steps from 4-(3-(difluoromethyl)-5-fluorobenzyl)-2-hydrazineylpyridine (Intermediate 13, 1.0 g, 3.74 mmol), ethyl 2-methyl-4-oxo-4,5-dihydrofuran-3-carboxylate (Intermediate 10, 0.638 g, 3.74 mmol) and acetic acid (0.021 mL, 0.374 mmol) in EtOH (30 mL) heated at 80° C. for 16 h; and LiOH (0.756 g, 31.6 mmol), water (5 mL), MeOH (20 mL) and THF (20 mL) stirred at RT for 16 h using the methods of Intermediate 17. After completion of step 2, the title compound was isolated as a white solid by removal of the solvent in vacuo, dissolution in water (50 mL) and acidification with 2 N HCl to pH ~2. The aqueous layer was extracted with EtOAc (4×50 mL). The combined organic layers were washed with brine (50 mL), dried ($Na_2SO_4$) and the solvent removed in vacuo. Data in table 2.

Intermediate Route 11, Exemplified by the Preparation of Intermediate 20, 1-(6-(3-fluoro-5-(trifluoromethyl)benzyl)pyridin-2-yl)-3-(methoxycarbonyl)-1H-pyrazole-4-carboxylic acid

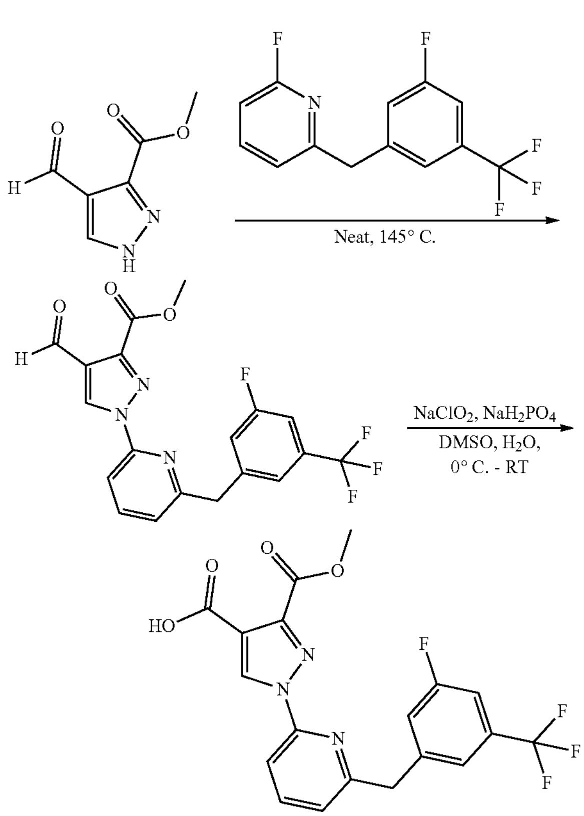

Step 1. 2-Fluoro-6-(3-fluoro-5-(trifluoromethyl)benzyl) pyridine (Intermediate 6, 0.8 g, 2.93 mmol) and methyl 4-formyl-1H-pyrazole-3-carboxylate (0.677 g, 4.39 mmol) were heated at 145° C. for 16 h. The reaction mixture was partitioned between water (50 mL) and DCM (50 mL). The organic layer was separated and the aqueous layer extracted with DCM (50 mL). The combined organic layers were washed with brine (50 mL), dried ($Na_2SO_4$) and the solvent removed in vacuo. The residue was purified by gradient flash column chromatography eluting with 0-40% EtOAc in pet-ether to afford methyl 1-(6-(3-fluoro-5-(trifluoromethyl) benzyl)pyridin-2-yl)-4-formyl-1H-pyrazole-3-carboxylate as a brown liquid (0.66 g, 50%).

LCMS (Method 14): m/z 408.0 (ES+), at 2.11 min.

$^1H$ NMR: (400 MHz, DMSO-$d_6$) δ: 10.29 (s, 1H), 9.12 (s, 1H), 8.05 (t, J=10.8 Hz, 1H), 7.88 (d, J=10.8 Hz, 1H), 7.69-7.67 (m, 2H), 7.53-7.48 (m, 2H), 4.31 (s, 2H), 3.95 (s, 3H).

Step 2. Sodium dihydrogen phosphate (0.147 g, 1.23 mmol) in water (5 mL) was added to a stirred solution of methyl 1-(6-(3-fluoro-5-(trifluoromethyl)benzyl)pyridin-2-yl)-4-formyl-1H-pyrazole-3-carboxylate (0.25 g, 0.61 mmol) in DMSO (30 mL) at RT followed by the addition of sodium chlorite (0.222 g, 2.46 mmol) in water (5 mL) at 0° C. over a period of 30 minutes. Reaction mixture was stirred at RT for 16 h. The reaction mixture was diluted with water (50 mL), acidified with 1 N HCl solution to pH ~5 and extracted with DCM (50 mL). The organic layer was removed and the aqueous layer extracted with DCM (50 mL). The combined organic layers were washed with brine (30 mL), dried ($Na_2SO_4$) and the solvent removed in vacuo. The residue was purified by gradient flash column chromatography eluting with 0-45% EtOAc in pet-ether to afford 1-(6-(3-fluoro-5-(trifluoromethyl)benzyl)pyridin-2-yl)-3-(methoxycarbonyl)-1H-pyrazole-4-carboxylic acid as a white solid (0.17 g, 65%). Data in table 2.

Intermediate Route 12, Exemplified by the Preparation of Intermediate 21, 1-(4-(3-fluoro-5-(trifluoromethyl)benzyl)pyridin-2-yl)-4-(hydroxymethyl)-1H-pyrazole-3-carboxylic acid

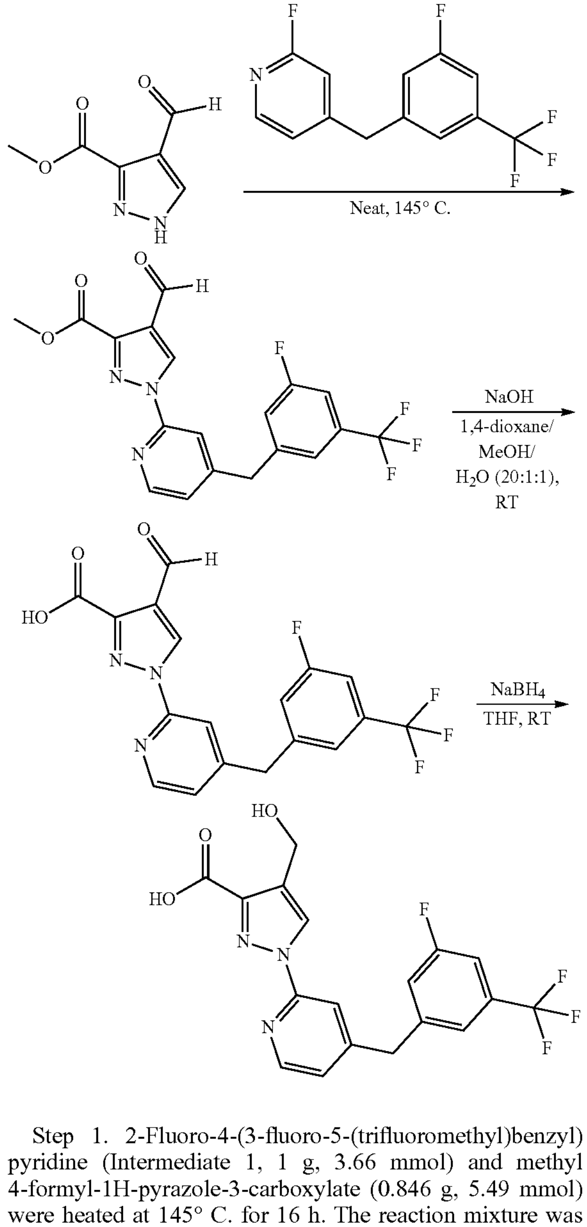

Step 1. 2-Fluoro-4-(3-fluoro-5-(trifluoromethyl)benzyl)pyridine (Intermediate 1, 1 g, 3.66 mmol) and methyl 4-formyl-1H-pyrazole-3-carboxylate (0.846 g, 5.49 mmol) were heated at 145° C. for 16 h. The reaction mixture was purified by gradient flash column chromatography eluting with 0-20% EtOAc in pet-ether to afford methyl 1-(4-(3-fluoro-5-(trifluoromethyl)benzyl)pyridin-2-yl)-4-formyl-1H-pyrazole-3-carboxylate as an off-white solid (970 mg, 65%).

LCMS (Method 12): m/z 408.0 (ES+), at 2.77 min.

$^1$H NMR: (400 MHz, DMSO-$d_6$) δ: 10.28 (s, 1H), 9.10 (s, 1H), 8.50 (d, J=4.8 Hz, 1H), 8.04 (s, 1H), 7.68 (s, 1H), 7.63-7.55 (m, 2H), 7.49 (d, J=4.8 Hz, 1H), 4.29 (s, 2H), 3.96 (s, 3H).

Step 2. NaOH (95 mg, 2.38 mmol), water (1 mL) and MeOH (1 mL) were added to a stirred solution of methyl 1-(4-(3-fluoro-5-(trifluoromethyl)benzyl)pyridin-2-yl)-4-formyl-1H-pyrazole-3-carboxylate (970 mg, 2.38 mmol) in 1,4-dioxane (20 mL) and the resultant reaction mixture was stirred at RT for 1 h. The solvent was removed in vacuo. The residue obtained was acidified with 1.5 N HCl to pH ~6 and partitioned between water (10 mL) and EtOAc (15 mL). The organic layer was separated, dried ($Na_2SO_4$) and the solvent removed in vacuo to afford 1-(4-(3-fluoro-5-(trifluoromethyl)benzyl)pyridin-2-yl)-4-formyl-1H-pyrazole-3-carboxylic acid as an off-white solid (800 mg, 85%).

$^1$H NMR: (400 MHz, DMSO-$d_6$) δ: 9.07 (s, 1H), 8.53 (s, 1H), 8.48 (d, J=7.2 Hz, 1H), 7.94 (s, 1H), 7.67-7.63 (m, 3H), 7.37 (d, J=4.8 Hz, 1H), 4.67 (s, 2H). 1 exchangeable proton not observed.

Step 3. $NaBH_4$ (231 mg, 6.10 mmol) was added to a stirred solution of 1-(4-(3-fluoro-5-(trifluoromethyl)benzyl)pyridin-2-yl)-4-formyl-1H-pyrazole-3-carboxylic acid (800 mg, 2.03 mmol) in THF (20 mL) and the resultant reaction mixture was stirred at RT for 1 h. The reaction mixture was neutralized with 1 N HCl (10 mL) and the aqueous layer extracted with 20% MeOH in DCM (20 mL). The organic layer was separated, dried ($Na_2SO_4$) and the solvent removed in vacuo. The residue was purified by prep HPLC (Method 3) to afford 1-(4-(3-fluoro-5-(trifluoromethyl)benzyl)pyridin-2-yl)-4-(hydroxymethyl)-1H-pyrazole-3-carboxylic acid as a white solid (100 mg, 12%). Data in table 2.

Intermediate 22, 1-(6-(3-fluoro-5-(trifluoromethyl)benzyl)pyridin-2-yl)-4-(hydroxymethyl)-1H-pyrazole-3-carboxylic acid

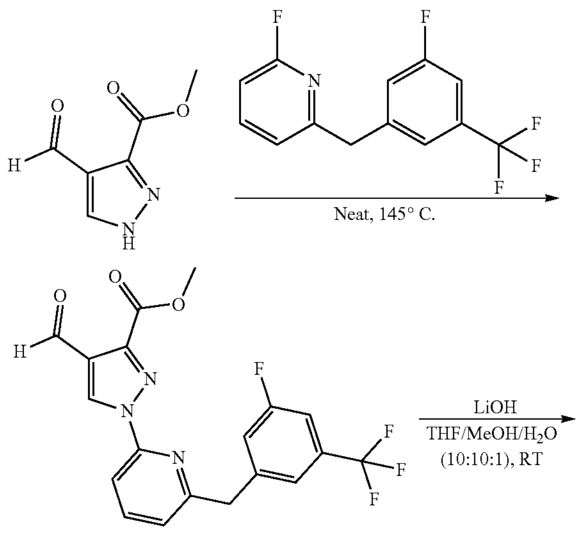

-continued

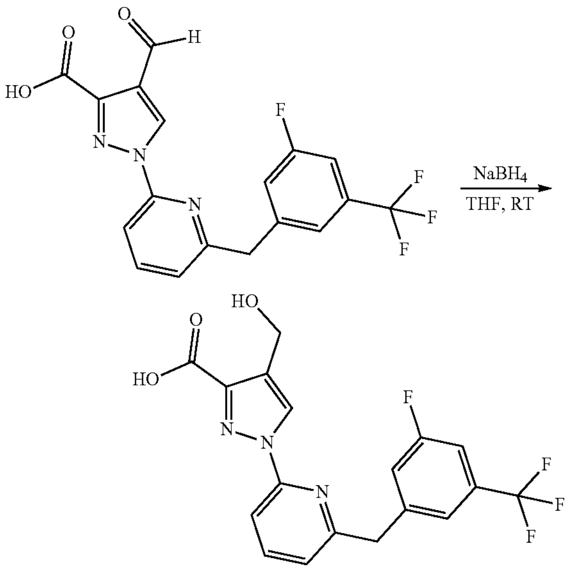

The title compound (35 mg, 15%) was prepared in three steps from 2-fluoro-6-(3-fluoro-5-(trifluoromethyl)benzyl) pyridine (Intermediate 6, 0.8 g, 2.93 mmol) and methyl 4-formyl-1H-pyrazole-3-carboxylate (0.677 g, 4.39 mmol) heated at 145° C. for 16 h; LiOH·$H_2O$ (8.8 mg, 0.37 mmol), water (0.2 mL), MeOH (2 mL) and THF (2 mL) stirred at RT for 2 h; and $NaBH_4$ (0.024 g, 0.636 mmol) in MeOH (10 mL) added at 0° C. and stirred at RT for 24 h using the methods of Intermediate 21, step 1, Intermediate 17, step 2, and Intermediate 21, step 3. After completion of step 3, the title compound was isolated as a yellow gum by removal of the solvent in vacuo and dissolution in water (30 mL). The aqueous layer was extracted with 20% MeOH in DCM (5×20 mL). The combined organic layers were washed with brine (50 mL), dried ($Na_2SO_4$) and the solvent removed in vacuo. Data in table 2.

Intermediate Route 13, Exemplified by the Preparation of Intermediate 23, 1-(2-(3-fluoro-5-(trifluoromethyl)benzyl)-5-methylpyridin-4-yl)-3-methyl-1H-pyrazole-4-carboxylic acid

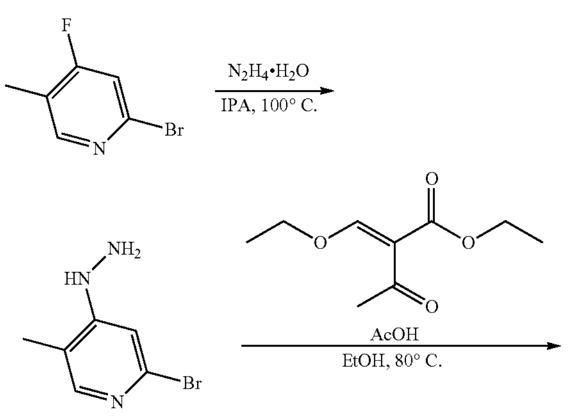

-continued

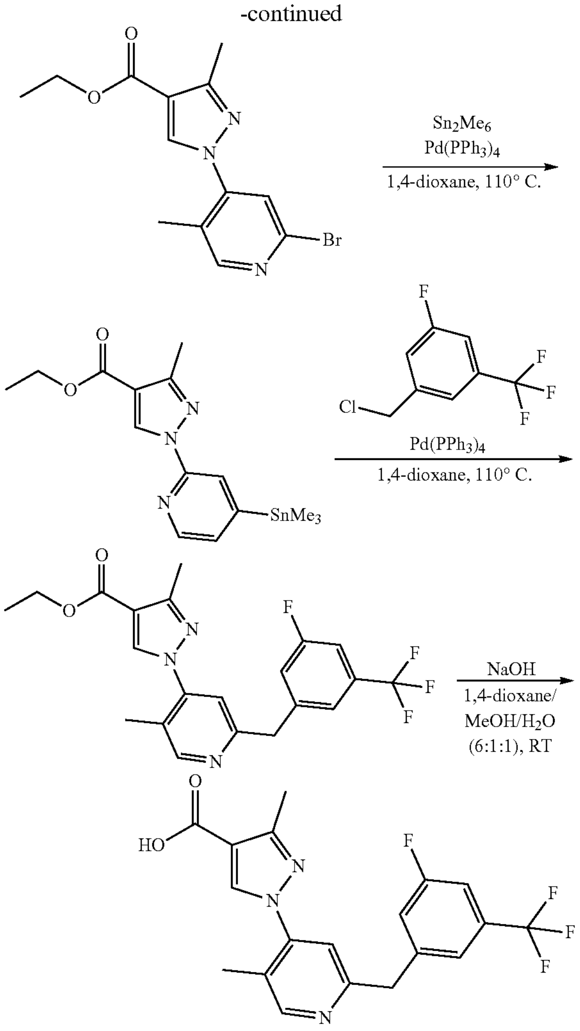

Steps 1 and 2. Ethyl 1-(2-bromo-5-methylpyridin-4-yl)-3-methyl-1H-pyrazole-4-carboxylate (300 mg, 46%) was prepared in two steps from 2-bromo-4-fluoro-5-methylpyridine (400 mg, 2.11 mmol) and hydrazine hydrate (1.06 mL, 21.1 mmol) in IPA (10 mL) heated at 100° C. for 16 h; and ethyl 2-(ethoxymethylene)-3-oxobutanoate (157 mg, 0.85 mmol) and acetic acid (25 mg, 0.42 mmol) in EtOH (5 mL) heated at 80° C. for 15 h using the methods of Intermediate 15, steps 1 and 2. After completion of step 2, the product was isolated as an off-white solid by partitioning between water (15 mL) and EtOAc (20 mL). The organic layer was separated, dried ($Na_2SO_4$) and the solvent removed in vacuo.

LCMS (Method 13): m/z 324.0 (ES+), at 2.22 min.

$^1$H NMR: (400 MHz, DMSO-$d_6$) δ: 8.55 (s, 1H), 8.10 (s, 1H), 7.88 (s, 1H), 4.30-4.24 (m, 2H), 2.39 (s, 3H), 2.03 (s, 3H), 1.30 (t, J=6.8 Hz, 3H).

Step 3. $Sn_2Me_6$ (455 mg, 1.39 mmol) and $Pd(PPh_3)_4$ (53.5 mg, 0.046 mmol) were added to a solution of ethyl 1-(2-bromo-5-methylpyridin-4-yl)-3-methyl-1H-pyrazole-4-carboxylate (300 mg, 0.93 mmol) in 1,4-dioxane (10 mL) and the resultant reaction mixture was heated at 110° C. for 15 h. The solvent was removed in vacuo. The residue was triturated with pet-ether (10 mL) and dried in vacuo to afford ethyl 3-methyl-1-(5-methyl-2-(trimethylstannyl)pyridin-4-yl)-1H-pyrazole-4-carboxylate as a brown semi-solid (300 mg, crude). The crude product was used in the next step without further purification.

LCMS (Method 1): m/z 410.0 (ES+), at 1.38 min.

Step 4. $Pd(PPh_3)_4$ (33.7 mg, 0.029 mmol) was added to a solution of ethyl 3-methyl-1-(5-methyl-2-(trimethylstannyl) pyridin-4-yl)-1H-pyrazole-4-carboxylate (286 mg, 0.70 mmol) and 1-(bromomethyl)-3-fluoro-5-(trifluoromethyl) benzene (150 mg, 0.58 mmol) in 1,4-dioxane (10 mL) and the resultant reaction mixture was heated at 110° C. for 15 h. The solvent was removed in vacuo. The residue was purified by gradient flash column chromatography eluting with 0-30% EtOAc in pet-ether to afford ethyl 1-(2-(3-fluoro-5-(trifluoromethyl)benzyl)-5-methylpyridin-4-yl)-3-methyl-1H-pyrazole-4-carboxylate as a yellow gum (20 mg, 7%).

LCMS (Method 1): m/z 422.0 (ES+), at 2.73 min.

Step 5. The title compound (30 mg, crude) was prepared from ethyl 1-(2-(3-fluoro-5-(trifluoromethyl)benzyl)-5-methylpyridin-4-yl)-3-methyl-1H-pyrazole-4-carboxylate (20 mg, 0.047 mmol) in 1,4-dioxane (3 mL) and sodium hydroxide (5.69 mg, 0.142 mmol), water (0.5 mL) and MeOH (0.5 mL) stirred at RT for 15 h using the methods of Intermediate 15, step 5.

The title compound was isolated as an off-white solid by acidification with 1.5 N HCl (5 mL) to pH ~6 and extraction of the aqueous layer with EtOAc (15 mL). The organic layer was separated, dried ($Na_2SO_4$) and the solvent removed in vacuo. Data in table 2.

Intermediate Route 14, Exemplified by the Preparation of Intermediate 24, 1-(4-(3-fluoro-5-(trifluoromethyl)benzyl)pyridin-2-yl)-5-(hydroxymethyl)-1H-pyrazole-3-carboxylic acid

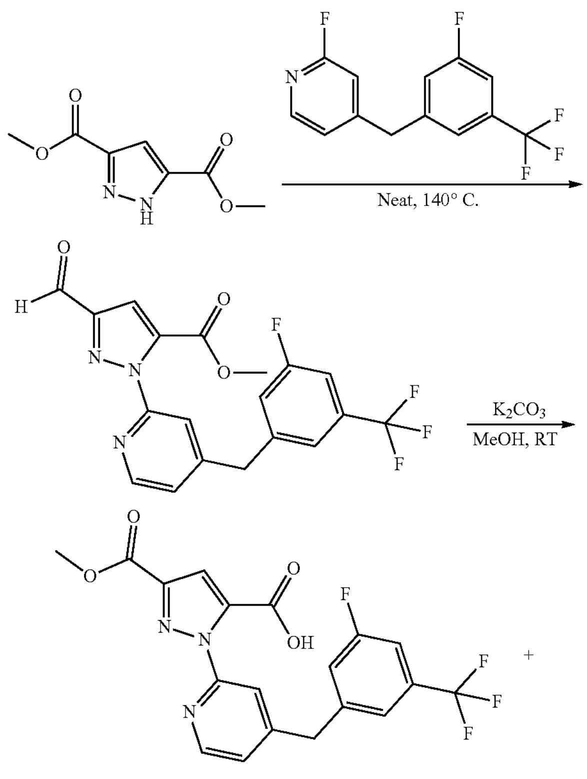

-continued

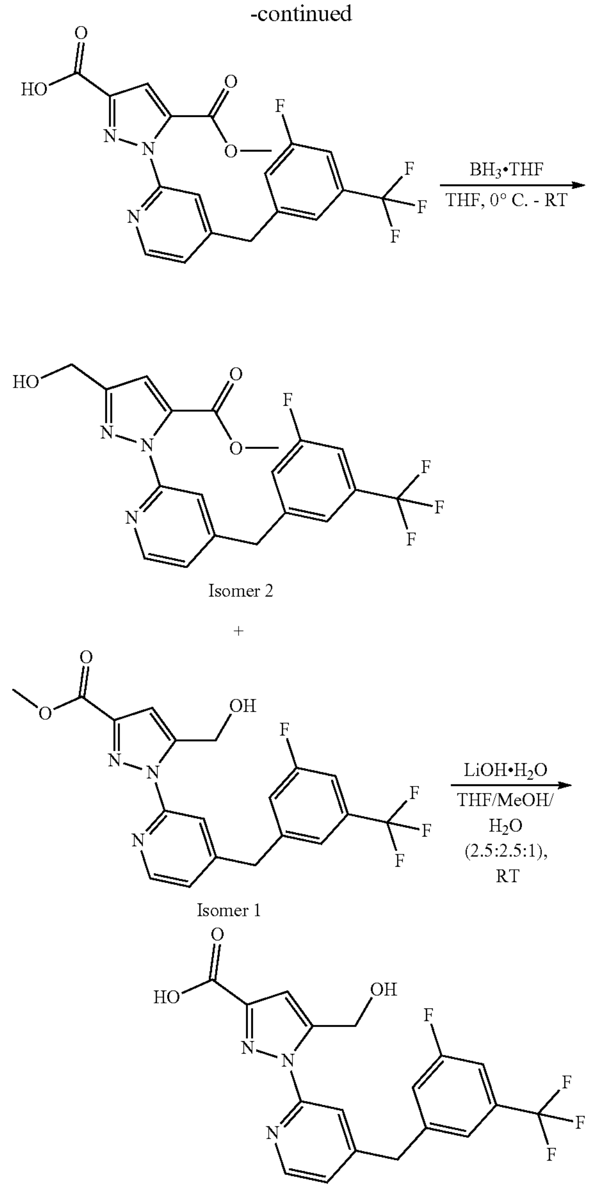

Step 1. 2-Fluoro-4-(3-fluoro-5-(trifluoromethyl)benzyl) pyridine (Intermediate 1, 300 mg, 1.10 mmol) and dimethyl 1H-pyrazole-3,5-dicarboxylate (202 mg, 1.10 mmol) were heated at 140° C. for 16 h. The reaction mixture was partitioned between water (50 mL) and EtOAc (50 mL). The organic layer was separated, washed with brine (2×30 mL), dried ($Na_2SO_4$) and the solvent removed in vacuo. The residue was purified by gradient flash column chromatography eluting with 0-50% EtOAc in pet-ether to afford dimethyl 1-(4-(3-fluoro-5-(trifluoromethyl)benzyl)pyridin-2-yl)-1H-pyrazole-3,5-dicarboxylate as a white solid (200 mg, 41%).

LCMS (Method 11): m/z 437.9 (ES+), at 2.86 min.

$^1H$ NMR: (400 MHz, DMSO-$d_6$) δ: 8.44 (d, J=6.8 Hz, 1H), 7.85 (s, 1H), 7.67-7.51 (m, 4H), 7.41 (s, 1H), 4.26 (s, 2H), 3.88 (s, 3H), 3.75 (s, 3H).

Step 2. $K_2CO_3$ (90 mg, 0.652 mmol) was added to a stirred solution of dimethyl 1-(4-(3-fluoro-5-(trifluoromethyl)benzyl)pyridin-2-yl)-1H-pyrazole-3,5-dicarboxylate (190 mg, 0.434 mmol) in MeOH (2 mL) and the resultant reaction mixture was stirred at RT for 16 h. The reaction mixture was diluted with water (30 mL) and acidified with 2 N HCl (5 mL) to pH ~2. The aqueous layer was extracted with EtOAc (3×30 mL). The combined organic layers were washed with brine (20 mL), dried ($Na_2SO_4$) and the solvent removed in vacuo to afford a mixture of regioisomers 1-(4-(3-fluoro-5-(trifluoromethyl)benzyl)pyridin-2-yl)-3-(methoxycarbonyl)-1H-pyrazole-5-carboxylic acid and 1-(4-(3-fluoro-5-(trifluoromethyl)benzyl)pyridin-2-yl)-5-(methoxycarbonyl)-1H-pyrazole-3-carboxylic acid as a white gum (140 mg, 76%).

LCMS (Method 15): m/z 423.9 (ES+), at 1.78 and 1.81 min.

Step 3. $BH_3$·THF (1 M in THF, 1.65 mL, 1.65 mmol) was added to a stirred solution of a mixture of 1-(4-(3-fluoro-5-(trifluoromethyl)benzyl)pyridin-2-yl)-3-(methoxycarbonyl)-1H-pyrazole-5-carboxylic acid and 1-(4-(3-fluoro-5-(trifluoromethyl)benzyl)pyridin-2-yl)-5-(methoxycarbonyl)-1H-pyrazole-3-carboxylic acid (0.140 g, 0.33 mmol) in THF (3 mL) at 0° C. and the resultant reaction mixture was stirred at RT for 2 h. The reaction mixture was quenched by the dropwise addition of MeOH (4 mL) at 0° C. and stirred at RT for 1 h. The solvent was removed in vacuo. The residue was purified by gradient flash column chromatography eluting with 0-50% EtOAc in pet-ether to afford methyl 1-(4-(3-fluoro-5-(trifluoromethyl)benzyl)pyridin-2-yl)-5-(hydroxymethyl)-1H-pyrazole-3-carboxylate (Isomer 1, mg, 22%) and methyl 1-(4-(3-fluoro-5-(trifluoromethyl)benzyl)pyridin-2-yl)-3-(hydroxymethyl)-1H-pyrazole-5-carboxylate (Isomer 2, 22 mg, 16%) as white solids.

Isomer 1:

LCMS (Method 11): m/z 409.9 (ES+), at 2.74 min.

$^1H$ NMR: (400 MHz, DMSO-$d_6$) δ: 8.45 (d, J=4.8 Hz, 1H), 7.93 (s, 1H), 7.67 (s, 1H), 7.62-7.56 (m, 2H), 7.40 (d, J=4.8 Hz, 1H), 6.91 (s, 1H), 5.52 (t, J=6.0 Hz, 1H), 4.90 (d, J=6.0 Hz, 2H), 4.27 (s, 2H), 3.86 (s, 3H).

Isomer 2:

LCMS (Method 1): m/z 410.0 (ES+), at 2.25 min.

$^1H$ NMR: (400 MHz, DMSO-$d_6$) δ: 8.37 (d, J=4.8 Hz, 1H), 7.71 (s, 1H), 7.66 (s, 1H), 7.62-7.57 (m, 2H), 7.40 (d, J=4.8 Hz, 1H), 6.90 (s, 1H), 5.31 (t, J=4.4 Hz, 1H), 4.86 (d, J=5.6 Hz, 2H), 4.23 (s, 2H), 3.73 (s, 3H).

Step 4. Lithium hydroxide monohydrate (13 mg, 0.305 mmol) was added to a stirred solution of methyl 1-(4-(3-fluoro-5-(trifluoromethyl)benzyl)pyridin-2-yl)-5-(hydroxymethyl)-1H-pyrazole-3-carboxylate (Isomer 1 from the previous step) (25 mg, 0.061 mmol) in THF (0.4 mL), MeOH (0.4 mL) and water (0.16 mL) and the resultant reaction mixture was stirred at RT for 16 h. The reaction mixture was diluted with water (30 mL) and acidified with 2 N HCl (5 mL) to pH ~2. The aqueous layer was extracted with EtOAc (3×30 mL). The combined organic layers were washed with brine (20 mL), dried ($Na_2SO_4$) and the solvent removed in vacuo to afford 1-(4-(3-fluoro-5-(trifluoromethyl)benzyl)pyridin-2-yl)-5-(hydroxymethyl)-1H-pyrazole-3-carboxylic acid as a white solid (20 mg, 82%). Data in table 2.

Preparation of Substituted Keto-Ester Intermediates

Intermediate Route 15, Exemplified by the Preparation of Intermediate 10, ethyl 2-methyl-4-oxo-4,5-dihydrofuran-3-carboxylate

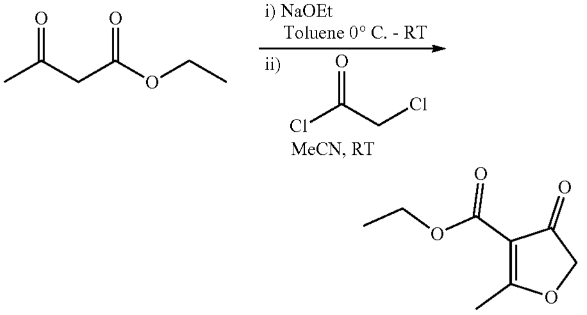

Sodium ethoxide (7.84 g, 115 mmol) was added and to a suspension of ethyl 3-oxobutanoate (10 g, 76.8 mmol) in toluene (50 mL) at 0° C. and the reaction mixture stirred at RT for 1 h. MeCN (20 mL) and 2-chloroacetyl chloride (6.15 mL, 38.4 mmol) were added and the resultant reaction mixture was stirred at RT for 2 h. The reaction mixture was acidified with 6 N aq $H_2SO_4$ (60 mL), the organic layer removed and the aqueous layer extracted with EtOAc (2×100 mL). The combined organic layers were washed with brine (100 mL), dried ($Na_2SO_4$) and the solvent removed in vacuo. The residue was purified by gradient flash column chromatography eluting with 0-10% EtOAc in pet-ether to afford ethyl 2-methyl-4-oxo-4,5-dihydrofuran-3-carboxylate as a yellow liquid (2.8 g, 21%). Data in table 2.

Intermediate Route 16, Exemplified by the Preparation of Intermediate 11, methyl 2-acetyl-4-methoxy-3-oxobutanoate

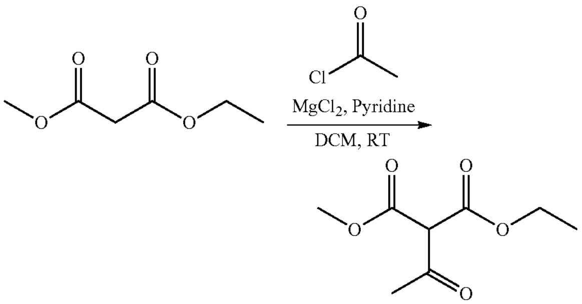

Acetyl chloride (0.533 g, 6.84 mmol) and pyridine (1.08 g, 13.69 mmol) were added to a stirred solution of methyl 4-methoxy-3-oxobutanoate (1 g, 6.84 mmol) and magnesium chloride (0.646 g, 6.84 mmol) in DCM (10 mL) at RT and the resultant reaction mixture was stirred at RT for 16 h. The reaction mixture was partitioned between water (100 mL) and DCM (2×100 mL). The combined organic layers were washed with brine (100 mL), dried ($Na_2SO_4$) and the solvent removed in vacuo. The residue was purified by gradient flash column chromatography eluting with 0-10% EtOAc in pet-ether to afford methyl 2-acetyl-4-methoxy-3-oxobutanoate as a yellow liquid (1 g, 77%). Data in table 2.

Preparation of Substituted Benzyl Chloride Intermediates

Intermediate Route 17, Exemplified by the Preparation of Intermediate 12, 1-(chloromethyl)-3-(difluoromethyl)-5-fluorobenzene

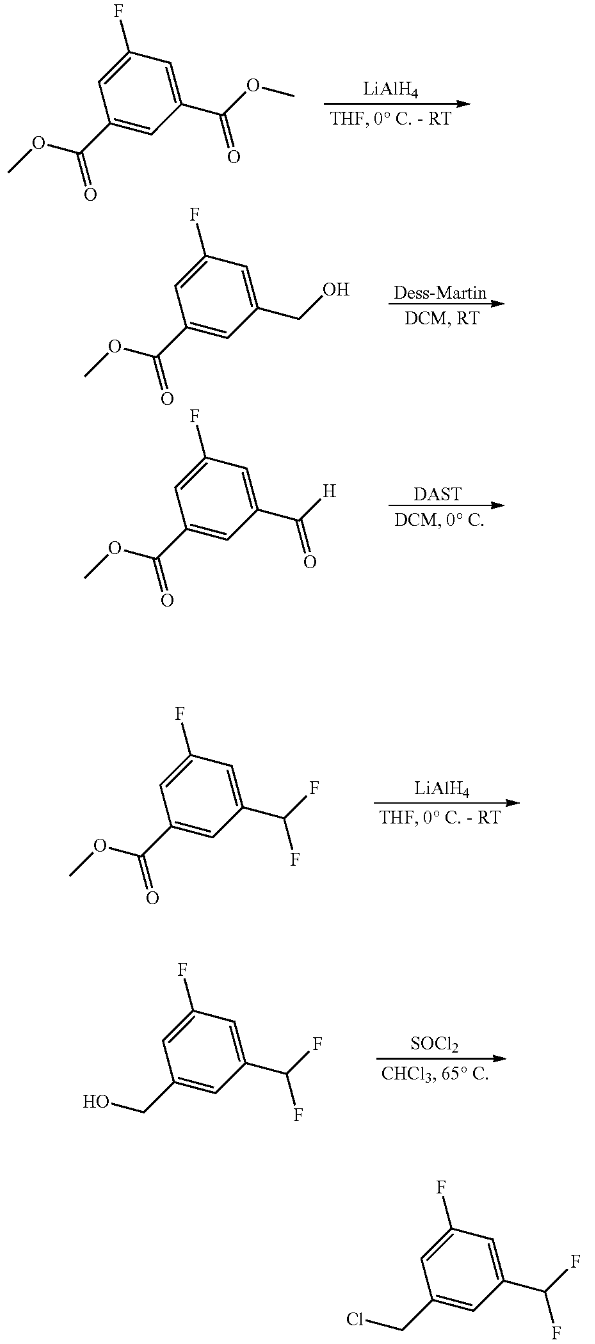

Step 1. $LiAlH_4$ (1.0 M in THF, 7.0 mL, 7.0 mmol) was added to a stirred solution of dimethyl 5-fluoroisophthalate (3 g, 14.1 mmol) in THF (10 mL), at 0° C. and the reaction mixture was stirred at RT for 3h. The reaction mixture was neutralized with 1.5 N HCl (50 mL) to pH ~7, and the reaction mixture was partitioned between water (100 mL) and EtOAc (50 mL). The organic layer was separated, dried ($Na_2SO_4$) and the solvent removed in vacuo to afford methyl 3-fluoro-5-(hydroxymethyl)benzoate as a colourless liquid (1.12 g. 43%).

GCMS (Method 1): m/z 184.0 (ES+), at 7.34 min.

$^1H$ NMR: (400 MHz, DMSO-$d_6$) δ: 7.79 (s, 1H), 7.55 (d, J=12.8 Hz, 1H), 7.43 (d, J=12.8 Hz, 1H), 5.49 (t, J=7.6 Hz, 1H), 4.58 (d, J=7.6 Hz, 2H), 3.87 (d, J=2.4 Hz, 3H).

Step 2. Dess-Martin periodinane (2.3 g, 5.54 mmol) was added to a solution of methyl 3-fluoro-5-(hydroxymethyl) benzoate (510 mg, 2.77 mmol) in DCM (10 mL) and the reaction mixture was stirred at RT for 2h. The reaction mixture was filtered and the filtrate was concentrated in vacuo. The residue was purified by gradient flash column chromatography eluting with 0-30% EtOAc in hexane to afford methyl 3-fluoro-5-formylbenzoate as a white solid (410 mg, 81%).

GCMS (Method 1): m/z 182.0 (ES+), at 6.76 min.

$^1H$ NMR: (400 MHz, DMSO-$d_6$) δ: 10.08 (d, J=2.4 Hz, 1H), 8.33 (d, J=1.6 Hz, 1H), 8.05-8.04 (m, 2H), 3.92 (s, 3H).

Step 3. DAST (0.44 mL, 3.37 mmol) was added to a solution of methyl 3-fluoro-5-formylbenzoate (410 mg, 2.25 mmol) at 0° C. and the reaction mixture was stirred at RT for 2h. The reaction mixture was neutralized with 10% $NaHCO_3$ (20 mL) to pH ~7, and reaction mixture was partitioned between water (100 mL) and DCM (50 mL). The organic layer was separated, dried ($Na_2SO_4$) and the solvent removed in vacuo. The residue was purified by gradient flash column chromatography eluting with 0-30% EtOAc in hexane to afford methyl 3-(difluoromethyl)-5-fluorobenzoate as a colourless liquid (400 mg, 87%).

GCMS (Method 2): m/z 204.0 (ES+), at 2.36 min.

$^1H$ NMR: (400 MHz, DMSO-$d_6$) δ: 7.99 (s, 1H), 7.89 (d, J=11.2 Hz, 1H), 7.80 (d, J=11.2 Hz, 1H), 7.35-6.98 (m, 1H), 3.91 (s, 3H).

Step 4. $LiAlH_4$ (2.0 M in THF, 0.45 mL, 0.90 mmol) was added to a solution of methyl 3-(difluoromethyl)-5-fluorobenzoate (390 mg, 1.81 mmol) in THF (10 mL) at 0° C. and the reaction mixture was stirred at RT for 1h. The reaction mixture was neutralized with 1.5 N HCl (50 mL) to pH ~7 and then partitioned between water (100 mL) and EtOAc (50 mL). The organic layer was separated, dried ($Na_2SO_4$) and the solvent removed in vacuo to afford (3-(difluoromethyl)-5-fluorophenyl)methanol as a colourless liquid (230 mg, 72%).

GCMS (Method 2): m/z 176.0 (ES+), at 6.36 min.

$^1H$ NMR: (400 MHz, DMSO-$d_6$) δ: 7.39 (s, 1H), 7.32-7.29 (m, 3H), 5.46 (d, J=6.4 Hz, 1H), 4.57 (t, J=6.4 Hz, 2H).

Step 5. Thionyl chloride (3 mL, 43.2 mmol) was added to a solution of (3-(difluoromethyl)-5-fluorophenyl)methanol (170 mg, 0.96 mmol) in chloroform (10 mL) at RT and the reaction mixture was heated at 65° C. for 12h. The reaction mixture was neutralized with 10% $NaHCO_3$ (20 mL) to pH ~7, then partitioned between water (50 mL) and EtOAc (50 mL). The organic layer was separated, dried ($Na_2SO_4$) and the solvent removed in vacuo to afford 1-(chloromethyl)-3-(difluoromethyl)-5-fluorobenzene as a colourless liquid (170 mg, crude). The crude product was used in the next step without further purification. Data in table 2.

TABLE 2

| Intermediates table | | | |
|---|---|---|---|
| Intermediate | Name | Structure | Data |
| 1 | 2-fluoro-4-(3-fluoro-5-(trifluoromethyl)benzyl)pyridine | 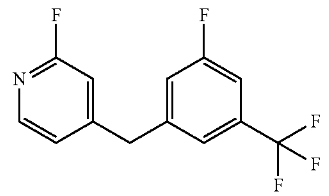 [SMILES: Fc1cc(Cc2ccnc(F)c2)cc(C(F)(F)F)c1] | LCMS (Method 1): m/z 274.0 (ES+), at 2.54 min. $^1$H NMR: (400 MHz, DMSO-d$_6$) δ: 8.17 (d, J = 4.4 Hz, 1H), 7.61 (s, 3H), 7.29 (d, J = 1.2 Hz, 1H), 7.16 (s, 1H), 4.17 (d, J = 3.6 Hz, 2H). |
| 2 | 4-fluoro-2-(3-fluoro-5-(trifluoromethyl)benzyl)pyridine | 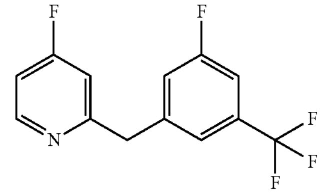 [SMILES: Fc1cc(Cc2cc(F)ccn2)cc(C(F)(F)F)c1] | LCMS (Method 2): m/z 274.1 (ES+), at 6.26 min. $^1$H NMR: (400 MHz, DMSO-d$_6$) δ: 8.54 (dd, J = 9.1, 5.7 Hz, 1H), 7.60-7.45 (m, 3H), 7.36 (dd, J = 10.2, 2.5 Hz, 1H), 7.20 (ddd, J = 8.6, 5.7, 2.5 Hz, 1H), 4.24 (s, 2H). |
| 3 | 4-(3-fluoro-5-(trifluoromethyl)benzyl)-2-hydrazineylpyridine | 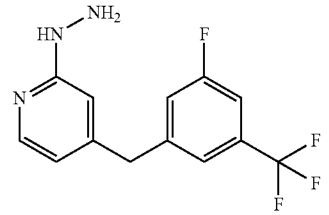 [SMILES: NNc1cc(Cc2cc(F)cc(C(F)(F)F)c2)ccn1] | LCMS (Method 1): m/z 286.2 (ES+), at 1.37 min. $^1$H NMR: (400 MHz, DMSO-d$_6$) δ: 7.88 (d, J = 5.2 Hz, 1H), 7.53-7.44 (m, 3H), 7.36 (s, 1H), 6.57 (s, 1H), 6.45-6.44 (m, 1H), 4.07 (s, 2H), 3.95 (s, 2H) |
| 4 | 1-(2-(3-fluoro-5-(trifluoromethyl)benzyl)pyridin-4-yl)-3-methyl-1H-pyrazole-4-carboxylic acid | 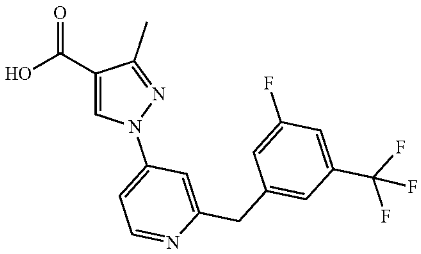 [SMILES: Cc1nn(-c2ccnc(Cc3cc(F)cc(C(F)(F)F)c3)c2)cc1C(=O)O] | LCMS (Method 4): m/z 380.3 (ES+), at 1.67 min. $^1$H NMR: Not recorded. |
| 5 | 1-(4-(3-fluoro-5-(trifluoromethyl)benzyl)pyridin-2-yl)-1H-pyrazole-3-carboxylic acid | 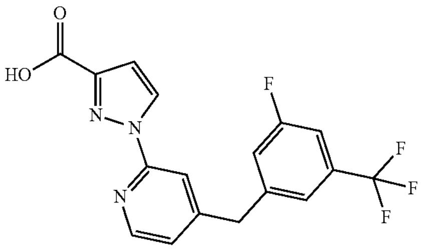 [SMILES: O=C(O)c1ccn(-c2cc(Cc3cc(F)cc(C(F)(F)F)c3)ccn2)n1] | LCMS (Method 4): m/z 366.0 (ES+), at 1.76 min. $^1$H NMR: Not recorded. |
| 6 | 2-fluoro-6-(3-fluoro-5-(trifluoromethyl)benzyl)pyridine | 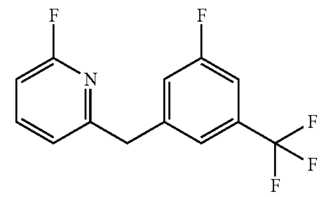 [SMILES: Fc1cc(Cc2cccc(F)n2)cc(C(F)(F)F)c1] | LCMS (Method 7): m/z 274.0 (ES+), at 2.48 min. $^1$H NMR: (400 MHz, DMSO-d$_6$) δ: 7.94 (d, J = 1.2 Hz, 1H), 7.55-7.48 (m, 3H), 7.33 (d, J = 6.4 Hz, 1H), 7.03 (t, J = 7.2 Hz, 1H), 4.19 (s, 2H). |

TABLE 2-continued

| Intermediates table | | | |
|---|---|---|---|
| Intermediate | Name | Structure | Data |
| 7 | 1-(4-(3-fluoro-5-(trifluoromethyl)benzyl)pyridin-2-yl)-4-methyl-1H-pyrazole-3-carboxylic acid | 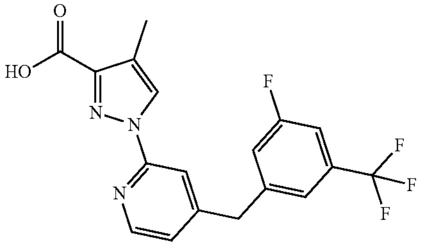 [SMILES: Cc1cn(-c2cc(Cc3cc(F)cc(C(F)(F)F)c3)ccn2)nc1C(=O)O] | LCMS (Method 4): m/z 380.2 (ES+), at 1.83 min. $^1$H NMR: Not recorded. |
| 8 | 1-(2-(3-fluoro-5-(trifluoromethyl)benzyl)pyridin-4-yl)-1H-pyrazole-3-carboxylic acid | 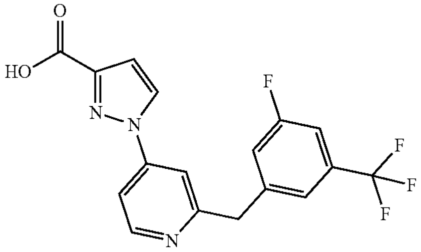 [SMILES: O=C(O)c1ccn(-c2ccnc(Cc3cc(F)cc(C(F)(F)F)c3)c2)n1] | LCMS (Method 8): m/z 366.2 (ES+), at 0.67 min. $^1$H NMR: Not recorded. |
| 9 | 1-(4-(3-fluoro-5-(trifluoromethyl)benzyl)pyridin-2-yl)-5-methyl-1H-pyrazole-3-carboxylic acid | 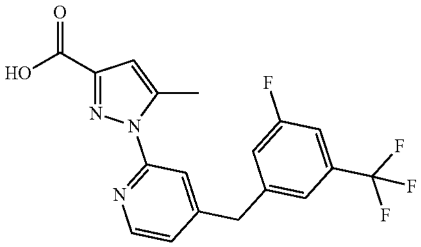 [SMILES: Cc1cc(C(=O)O)nn1-c1cc(Cc2cc(F)cc(C(F)(F)F)c2)ccn1] | LCMS (Method 4): m/z 380.4 (ES+), at 1.75 min. $^1$H NMR: Not recorded. |
| 10 | ethyl 2-methyl-4-oxo-4,5-dihydrofuran-3-carboxylate | 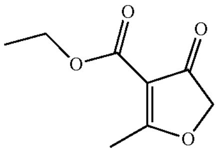 | LCMS (Method 11): m/z 171.0 (ES+), at 1.94 min. $^1$H NMR: (400 MHz, DMSO-$d_6$) δ: 4.78 (s, 2H), 4.17 (q, J = 3.6 Hz, 2H), 2.50 (s, 3H), 1.22 (t, J = 9.6 Hz, 3H). |
| 11 | methyl 2-acetyl-4-methoxy-3-oxobutanoate | 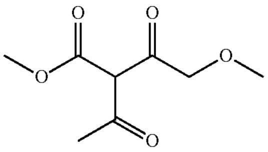 | LCMS (Method 1): m/z 187.1 (ES−), at 1.41 min. $^1$H NMR: (400 MHz, DMSO-$d_6$) δ: 4.49 (s, 2H), 3.88 (s, 3H), 3.47 (s, 3H), 2.42 (s, 3H). 1 exchangeable proton not observed. |
| 12 | 1-(chloromethyl)-3-(difluoromethyl)-5-fluorobenzene | 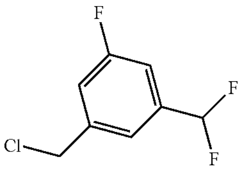 [SMILES: Fc1cc(CCl)cc(C(F)F)c1] | GCMS (Method 2): m/z 193.9 (ES+), at 2.25 min. $^1$H NMR: Not recorded. |
| 13 | 4-(3-(difluoromethyl)-5-fluorobenzyl)-2-hydrazineylpyridine | 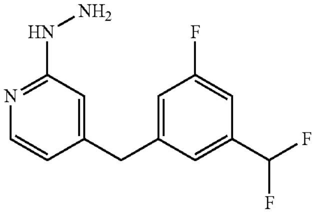 [SMILES: NNc1cc(Cc2cc(F)cc(C(F)F)c2)ccn1] | LCMS (Method 11): m/z 267.9 (ES+), at 3.00 min. $^1$H NMR: Not recorded. |

TABLE 2-continued

| Intermediates table | | | |
|---|---|---|---|
| Intermediate | Name | Structure | Data |
| 14 | 2-(3-fluoro-5-(trifluoromethyl)benzyl)-4-hydrazineylpyridine | 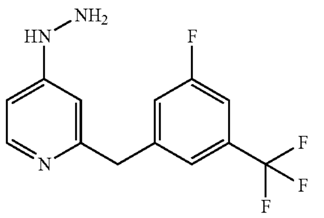 [SMILES: NNc1ccnc(Cc2cc(F)cc(C(F)(F)F)c2)c1] | LCMS (Method 1): m/z 286.1 (ES+), at 1.19 min. $^1$H NMR: (400 MHz, DMSO-d6) δ: 7.95 (d, J = 6.0 Hz, 1H), 7.56-7.21 (m, 4H), 6.59 (d, J = 1.6 Hz, 1H), 6.51-6.49 (m, 1H), 4.15 (s, 2H), 3.99 (s, 2H). |
| 15 | 1-(4-(3-(difluoromethyl)-5-fluorobenzyl)pyridin-2-yl)-3-methyl-1H-pyrazole-4-carboxylic acid | 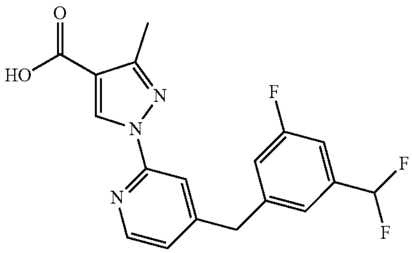 [SMILES: Cc1nn(-c2cc(Cc3cc(F)cc(C(F)F)c3)ccn2)cc1C(=O)O] | LCMS (Method 11): m/z 362.1 (ES+), at 2.23 min. $^1$H NMR: (400 MHz, DMSO-$d_6$) δ: 12.57 (s, 1H), 8.47 (d, J = 5.1 Hz, 1H), 8.01 (s, 1H), 7.76 (s, 1H), 7.46-7.40 (m, 3H), 7.32 (d, J = 9.3 Hz, 1H), 7.03 (t, J = 55.8 Hz, 1H), 4.20 (s, 2H), 2.74 (s, 3H). |
| 16 | 1-(4-(3-(difluoromethyl)-5-fluorobenzyl)pyridin-2-yl)-1H-pyrazole-3-carboxylic acid | 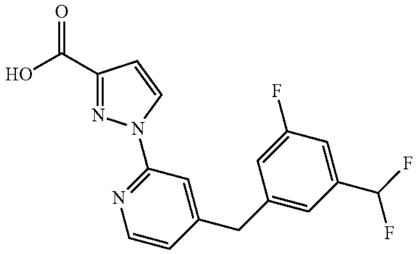 [SMILES: O=C(O)c1ccn(-c2cc(Cc3cc(F)cc(C(F)F)c3)ccn2)n1] | LCMS (Method 11): m/z 348.0 (ES+), at 2.55 min. $^1$H NMR: (300 MHz, DMSO-$d_6$) δ: 13.10 (s, 1H), 8.68 (d, J = 2.4 Hz, 1H), 8.44 (d, J = 4.8 Hz, 1H), 7.93 (s, 1H), 7.46-7.30 (m, 4H), 7.03 (t, J = 55.8 Hz, 1H), 6.95 (d, J = 2.4 Hz, 1H), 4.23 (s, 2H). |
| 17 | 1-(4-(3-fluoro-5-(trifluoromethyl)benzyl)pyridin-2-yl)-5-(hydroxymethyl)-3-methyl-1H-pyrazole-4-carboxylic acid | 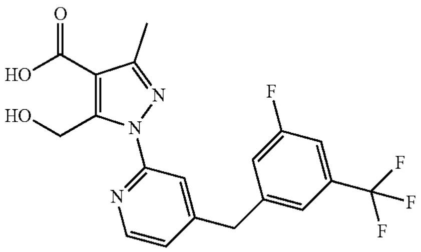 [SMILES: Cc1nn(-c2cc(Cc3cc(F)cc(C(F)(F)F)c3)ccn2)c(CO)c1C(=O)O] | LCMS (Method 12): m/z 410.0 (ES+), at 2.49 min. $^1$H NMR: (400 MHz, DMSO-$d_6$) δ: 8.46 (d, J = 6.8 Hz, 1H), 7.84 (s, 1H), 7.66-7.55 (m, 3H), 7.41 (d, J = 6.8 Hz, 1H), 5.01 (s, 2H), 4.24 (s, 2H), 2.44 (s, 3H). 2 exchangeable protons not observed. |
| 18 | 1-(2-(3-fluoro-5-(trifluoromethyl)benzyl)pyridin-4-yl)-5-(hydroxymethyl)-3-methyl-1H-pyrazole-4-carboxylic acid | 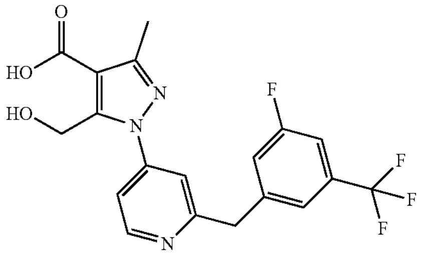 [SMILES: Cc1nn(-c2ccnc(Cc3cc(F)cc(C(F)(F)F)c3)c2)c(CO)c1C(=O)O] | LCMS (Method 1): m/z 410.0 (ES+), at 2.03 min. $^1$H NMR: (400 MHz, DMSO-$d_6$) δ: 8.65 (d, J = 7.2 Hz, 1H), 7.80 (s, 1H), 7.72 (d, J = 2.4 Hz, 1H), 7.61 (s, 1H), 7.54 (d, J = 12.4 Hz, 2H), 4.81 (s, 2H), 4.32 (s, 2H), 3.57 (s, 1H), 2.41 (s, 3H). 1 exchangeable proton not observed. |
| 19 | 1-(4-(3-(difluoromethyl)-5-fluorobenzyl)pyridin-2-yl)-5-(hydroxymethyl)-3-methyl-1H-pyrazole-4-carboxylic acid | 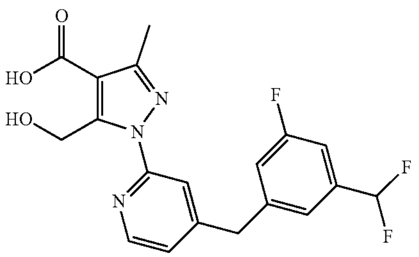 [SMILES: Cc1nn(-c2cc(Cc3cc(F)cc(C(F)F)c3)ccn2)c(CO)c1C(=O)O] | LCMS (Method 1): m/z 392.0 (ES+), at 2.48 min. $^1$H NMR: (300 MHz, DMSO-$d_6$) δ: 8.40 (d, J = 5.1 Hz, 1H), 7.74 (s, 1H), 7.45-7.41 (m, 2H), 7.32-7.30 (m, 2H), 7.03 (t, J = 55.5 Hz, 1H), 4.92 (d, J = 8.1 Hz, 2H), 4.18 (s, 2H), 2.38 (s, 3H). 2 exchangeable protons not observed. |

TABLE 2-continued

Intermediates table

| Intermediate | Name | Structure | Data |
| --- | --- | --- | --- |
| 20 | 1-(6-(3-fluoro-5-(trifluoromethyl)benzyl)pyridin-2-yl)-3-(methoxycarbonyl)-1H-pyrazole-4-carboxylic acid | 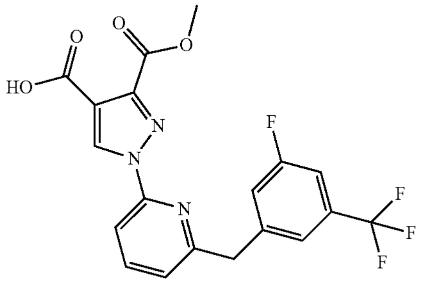 [SMILES: COC(=O)c1nn(-c2cccc(Cc3cc(F)cc(C(F)(F)F)c3)n2)cc1C(=O)O] | LCMS (Method 1): m/z 424.0 (ES+), at 2.50 min. $^1$H NMR: (400 MHz, DMSO-$d_6$) δ: 13.08 (s, 1H), 8.96 (s, 1H), 8.02 (t, J = 7.6 Hz, 1H), 7.82 (d, J = 7.6 Hz, 1H), 7.69-7.65 (m, 2H), 7.55 (d, J = 8.4 Hz, 1H), 7.47 (d, J = 7.2 Hz, 1H), 4.31 (s, 2H), 3.88 (s, 3H). |
| 21 | 1-(4-(3-fluoro-5-(trifluoromethyl)benzyl)pyridin-2-yl)-4-(hydroxymethyl)-1H-pyrazole-3-carboxylic acid | 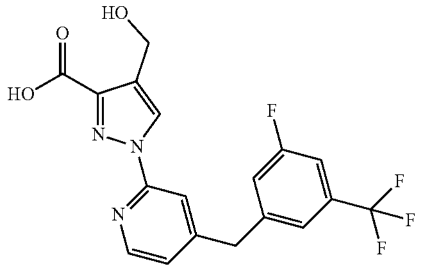 [SMILES: O=C(O)c1nn(-c2cc(Cc3cc(F)cc(C(F)(F)F)c3)ccn2)cc1CO] | LCMS (Method 1): m/z 396.0 (ES+), at 2.01 min. $^1$H NMR: (300 MHz, DMSO-$d_6$) δ: 8.53 (s, 1H), 8.43 (d, J = 4.8 Hz, 1H), 7.94 (s, 1H), 7.66-7.59 (m, 3H), 7.37 (d, J = 4.8 Hz, 1H), 4.66 (s, 2H), 4.26 (s, 2H). 2 exchangeable protons not observed. |
| 22 | 1-(6-(3-fluoro-5-(trifluoromethyl)benzyl)pyridin-2-yl)-4-(hydroxymethyl)-1H-pyrazole-3-carboxylic acid | 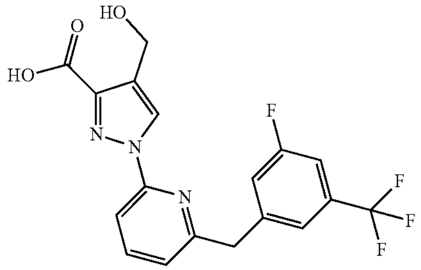 [SMILES: O=C(O)c1nn(-c2cccc(Cc3cc(F)cc(C(F)(F)F)c3)n2)cc1CO] | LCMS (Method 11): m/z 395.9 (ES+), at 2.52 min. $^1$H NMR: Not recorded. |
| 23 | 1-(2-(3-fluoro-5-(trifluoromethyl)benzyl)-5-methylpyridin-4-yl)-3-methyl-1H-pyrazole-4-carboxylic acid | 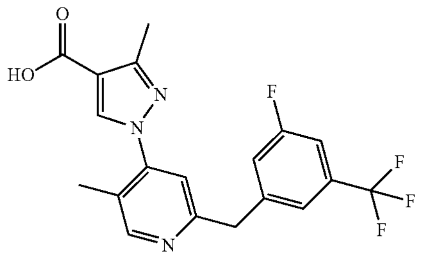 [SMILES: Cc1cnc(Cc2cc(F)cc(C(F)(F)F)c2)cc1-n1cc(C(=O)O)c(C)n1] | LCMS (Method 1): m/z 394.0 (ES+), at 2.24 min. $^1$H NMR: (400 MHz, DMSO-$d_6$) δ: 8.65 (s, 1H), 8.04 (s, 1H), 7.59 (s, 1H), 7.55-7.51 (m, 2H), 7.53 (s, 1H), 4.28 (s, 2H), 2.34 (s, 3H), 2.05 (s, 3H). 1 exchangeable proton not observed. |
| 24 | 1-(4-(3-fluoro-5-(trifluoromethyl)benzyl)pyridin-2-yl)-5-(hydroxymethyl)-1H-pyrazole-3-carboxylic acid | 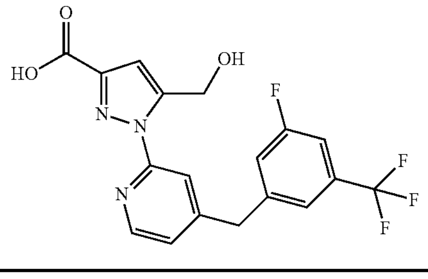 | LCMS (Method 12): m/z 396.0 (ES+), at 2.22 min. $^1$H NMR: (400 MHz, DMSO-$d_6$) δ: 13.03 (s, 1H), 8.44 (d, J = 5.2 Hz, 1H), 7.91 (d, J = 0.4 Hz, 1H), 7.66 (s, 1H), 7.61-7.55 (m, 2H), 7.39-7.38 (m, 1H), 6.86 (s, 1H), 5.48 (t, J = 6.4 Hz, 1H), 4.89 (d, J = 5.6 Hz, 2H), 4.26 (s, 2H). |

Synthesis of Examples

Typical procedures for the preparation of examples, as exemplified by the preparation of the below examples in Procedures 1-15.

Procedure 1

Example 1, 1-(4-(3-fluoro-5-(trifluoromethyl)benzyl)pyridin-2-yl)-1H-pyrazole-4-carboxamide

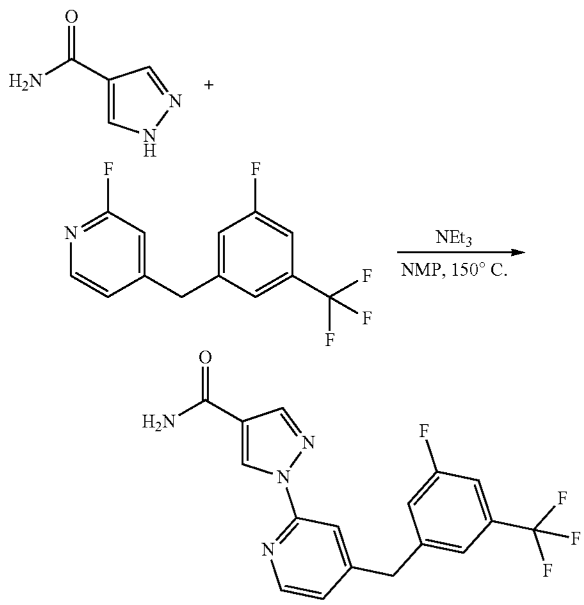

1H-pyrazole-4-carboxamide (49 mg, 0.44 mmol) was added to a solution of 2-fluoro-4-(3-fluoro-5-(trifluoromethyl)benzyl)pyridine (Intermediate 1, 30 mg, 0.11 mmol) and triethylamine (0.12 mL, 0.88 mmol) in NMP (2 mL) and the resultant reaction mixture was heated at 150° C. for 4 days. The reaction mixture was partitioned between EtOAc (2 mL) and water (4 mL) and the organic layer separated. The aqueous layer was extracted with EtOAc (2x3 mL), the combined organic layers dried (phase separator) and the solvent removed in vacuo. The residue was purified by gradient flash chromatography eluting with 12-100% EtOAc in i-hexane to afford 1-(4-(3-fluoro-5-(trifluoromethyl)benzyl)pyridin-2-yl)-1H-pyrazole-4-carboxamide as a white solid (7 mg, 17%). Data in table 3.

Procedure 2

Example 3, 1-(4-(3-fluoro-5-(trifluoromethyl)benzyl)pyridin-2-yl)-N-methyl-1H-pyrazole-4-carboxamide

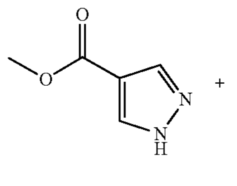

-continued

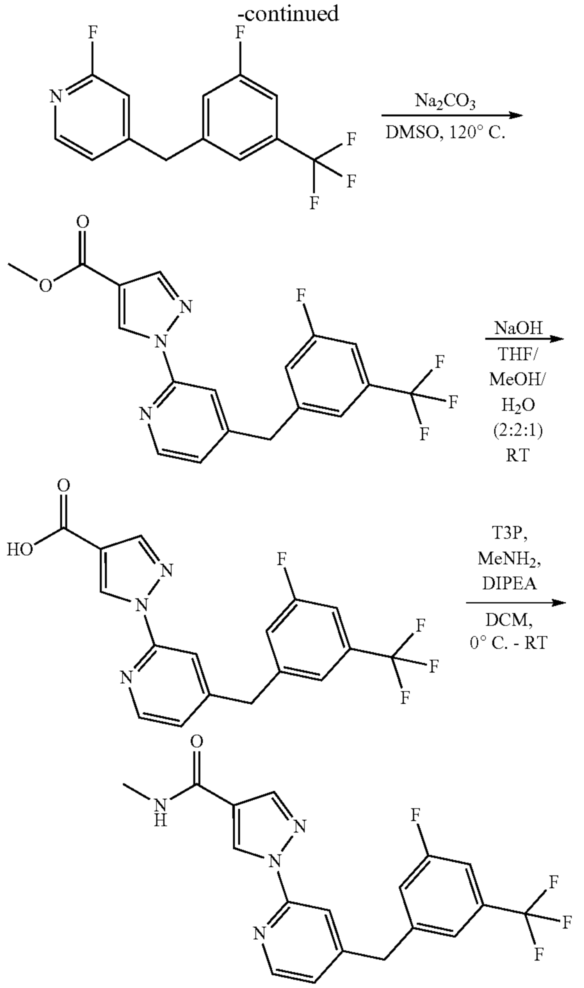

Step 1. A solution of methyl 1H-pyrazole-4-carboxylate (92 mg, 0.73 mmol), 2-fluoro-4-(3-fluoro-5-(trifluoromethyl)benzyl)pyridine (Intermediate 1, 200 mg, 0.73 mmol) and $Na_2CO_3$ (155 mg, 1.46 mmol) in DMSO (3 ml-) was heated at 120° C. for 12 h. The reaction mixture was poured into water (20 mL) and the aqueous layer was extracted with EtOAc (3x30 mL). The organic layers were combined and the solvent removed in vacuo to afford methyl 1-(4-(3-fluoro-5-(trifluoromethyl)benzyl)pyridin-2-yl)-1H-pyrazole-4-carboxylate as a brown semi-solid (210 mg, 76%).

LCMS (Method 4): m/z 380.1 (ES+), at 2.38 min.

Step 2. A solution of sodium hydroxide (68 mg, 1.66 mmol) in water (1 mL) was added to a solution of methyl 1-(4-(3-fluoro-5-(trifluoromethyl)benzyl)pyridin-2-yl)-1H-pyrazole-4-carboxylate (210 mg, 0.55 mmol) in THF (2 mL) and MeOH (2 mL) and the reaction mixture was stirred at RT for 16 h. The solvent was removed in vacuo and the residue was acidified with aq $NaHSO_4$ solution (20 mL). The aqueous layer was extracted with EtOAc (3x30 mL). The combined organic layers were dried ($Na_2SO_4$) and the solvent removed in vacuo to afford 1-(4-(3-fluoro-5-(trifluoromethyl)benzyl)pyridin-2-yl)-1H-pyrazole-4-carboxylic acid as an off white semi-solid (180 mg, 90%).

LCMS (Method 4): m/z 366.0 (ES+), at 1.71 min.

Step 3. 1-(4-(3-fluoro-5-(trifluoromethyl)benzyl)pyridin-2-yl)-1H-pyrazole-4-carboxylic acid (180 mg, 0.49 mmol), DIPEA (0.26 mL, 1.47 mmol) and methylamine (10 mL, 2M in THF) were stirred in DCM (2.00 mL) at 0° C. for 10 min and T3P (0.9 mL, 1.47 mmol, 50% solution in EtOAc) was added at 0° C. The reaction mixture was stirred at RT for 16 h. Aq $NaHCO_3$ solution (10 mL) was added to the reaction mixture and the aqueous layer was extracted with ethyl acetate (3×30 mL). The combined organic layers were dried ($Na_2SO_4$) and the solvent removed in vacuo to give 1-(4-(3-fluoro-5-(trifluoromethyl)benzyl)pyridin-2-yl)-N-methyl-1H-pyrazole-4-carboxamide as an off white solid (6 mg, 3%). Data in table 3.

Procedure 3

Example 6, 1-(4-(3-fluoro-5-(trifluoromethyl)benzyl)pyridin-2-yl)-3,5-dimethyl-1H-pyrazole-4-carboxamide

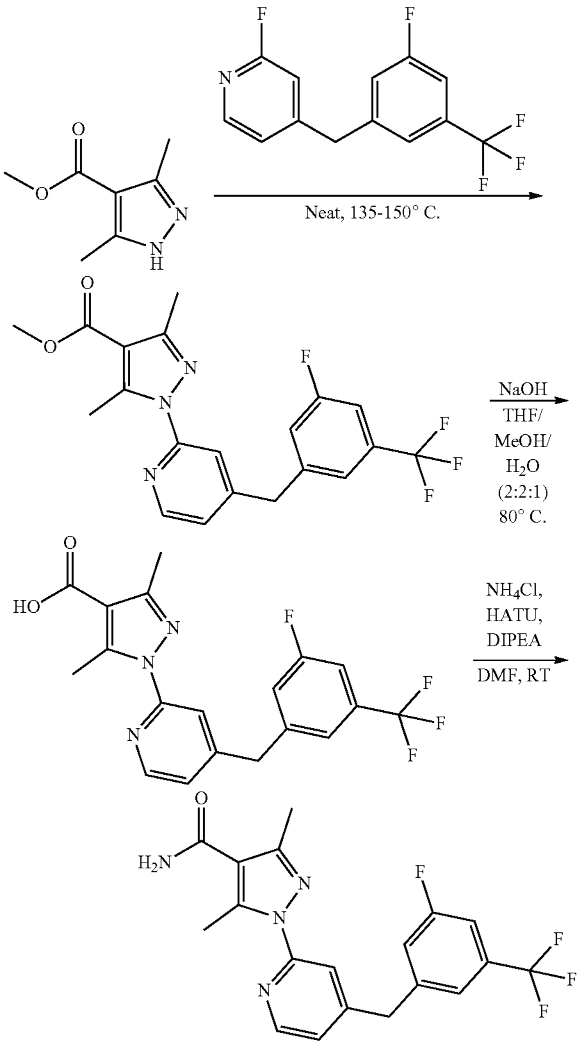

Step 1. A mixture of methyl 3,5-dimethyl-1H-pyrazole-4-carboxylate (100 mg, 0.64 mmol) and 2-fluoro-4-(3-fluoro-5-(trifluoromethyl)benzyl)pyridine (Intermediate 1, 177 mg, 0.65 mmol) was heated in reaction vessel at 135° C. for 16 h and then at 150° C. for 24 h. The reaction mixture was dissolved in 5% MeOH in DCM (10 mL) and the solvent removed in vacuo. The residue was purified by gradient flash column chromatography eluting with 14-20% EtOAc in hexane to afford methyl 1-(4-(3-fluoro-5-(trifluoromethyl)benzyl)pyridin-2-yl)-3,5-dimethyl-1H-pyrazole-4-carboxylate as a white solid (90 mg, 34%).

LCMS (Method 4): m/z 408.4 (ES+), at 2.45 min.

$^1H$ NMR: (400 MHz, DMSO-$d_6$) δ: 8.41 (d, J=5.0 Hz, 1H), 7.66 (s, 1H), 7.28 (s, 1H), 7.23-7.01 (m, 3H), 4.04 (s, 2H), 3.86 (s, 3H), 2.86 (s, 3H), 2.49 (s, 3H).

Step 2. NaOH (36 mg, 0.88 mmol) was added to a stirred solution of methyl 1-(4-(3-fluoro-5-(trifluoromethyl)benzyl)pyridin-2-yl)-3,5-dimethyl-1H-pyrazole-4-carboxylate (0.12 g, 0.295 mmol) in THF (4 mL), MeOH (4 mL) and water (2 mL). The reaction mixture was heated at 80° C. for 16 h. The solvent was removed in vacuo and the residue acidified with aq $NaHSO_4$ (10 mL) and extracted with EtOAc (3×20 mL). The combined organic layers were dried ($Na_2SO_4$) and the solvent removed in vacuo. The residue was triturated with $Et_2O$ (10 mL) to afford 1-(4-(3-fluoro-5-(trifluoromethyl)benzyl)pyridin-2-yl)-3,5-dimethyl-1H-pyrazole-4-carboxylic acid (100 mg) as a white solid.

LCMS (Method 4): m/z 394.3 (ES+), at 1.88 min.

$^1H$ NMR: (400 MHz, DMSO-$d_6$) δ: 12.47 (s, 1H), 8.43 (d, J=5.0 Hz, 1H), 7.76 (s, 1H), 7.68 (s, 1H), 7.62-7.55 (m, 2H), 7.38 (d, J=6.0 Hz, 1H), 4.21 (s, 2H), 2.74 (s, 3H), 2.37 (s, 3H).

Step 3. DIPEA (0.14 ml, 0.76 mmol) and HATU (116 mg, 30 mmol) were sequentially added to a mixture of 1-(4-(3-fluoro-5-(trifluoromethyl)benzyl)pyridin-2-yl)-3,5-dimethyl-1H-pyrazole-4-carboxylic acid (100 mg, 0.25 mmol) in DMF (2 mL). After 10 min stirring at RT, $NH_4Cl$ (68 mg, 1.27 mmol) was added and the resulting mixture was stirred at RT for 20 min. The reaction mixture was diluted with water and the resultant solid was filtered and washed with water (50 mL). The solid material was dried in vacuo and then triturated with $Et_2O$ (20 mL) to afford 1-(4-(3-fluoro-5-(trifluoromethyl)benzyl)pyridin-2-yl)-3,5-dimethyl-1H-pyrazole-4-carboxamide (11 mg, 11%) as a white solid. Data in table 3.

Procedure 4

Example 7, 1-(4-(3-fluoro-5-(trifluoromethyl)benzyl)pyridin-2-yl)-5-methyl-1H-pyrazole-4-carboxamide

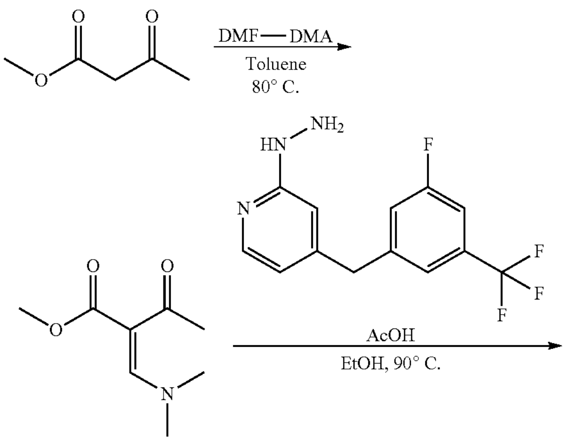

-continued

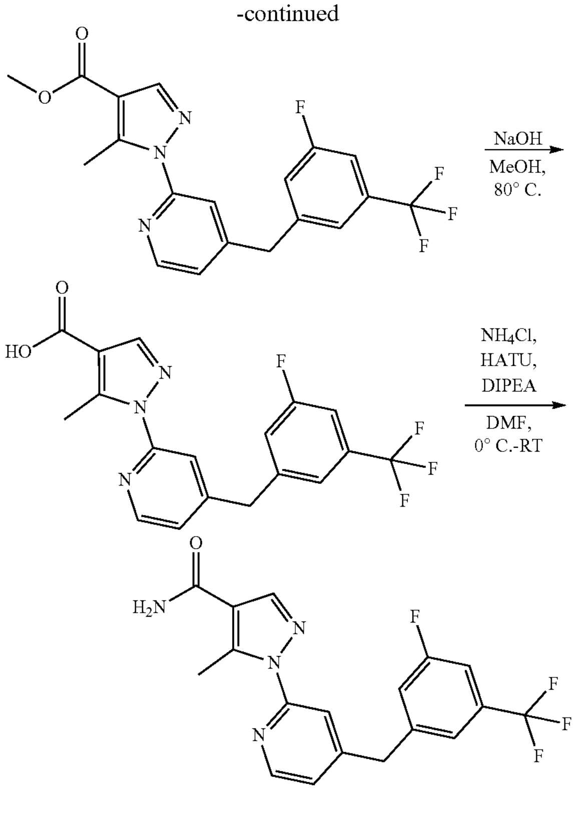

Step 1. A solution of methyl 3-oxobutanoate (2.00 g, 17.2 mmol) and DMF-DMA (3.08 g, 25.8 mmol) in toluene was heated at 80° C. for 2.5 h. The solvent was removed in vacuo to afford methyl (2E)-2-[(dimethylamino)methylidene]-3-oxobutanoate as a brown semi-solid (2.90 g, crude). The crude product was used in the next step without further purification.

Step 2. Methyl (2E)-2-[(dimethylamino)methylidene]-3-oxobutanoate (2, 180 mg, 1.05 mmol) and AcOH (2 mL) were added to a stirred solution of 4-(3-fluoro-5-(trifluoromethyl)benzyl)-2-hydrazineylpyridine (Intermediate 3, 150 mg, 0.526 mmol) in EtOH. The reaction mixture was heated at 90° C. for 2 h. The solvent was removed in vacuo and the residue was purified by gradient flash chromatography eluting with 20-30% EtOAc in hexane to afford methyl 1-(4-(3-fluoro-5-(trifluoromethyl)benzyl)pyridin-2-yl)-5-methyl-1H-pyrazole-4-carboxylate as an off white solid (200 mg, crude). The crude product was used in the next step without further purification.

LCMS (Method 4): m/z 394.0 (ES+), at 2.51 min.

Step 3. Sodium hydroxide (62.5 mg, 1.53 mmol) was added to a solution of methyl 1-(4-(3-fluoro-5-(trifluoromethyl)benzyl)pyridin-2-yl)-5-methyl-1H-pyrazole-4-carboxylate (200 mg, 0.508 mmol) in MeOH (4 mL) and the reaction mixture was heated at 80° C. for 5 h. The solvent was removed in vacuo and the residue was acidified with aq $NaHSO_4$ solution (20 mL). The aqueous layer was extracted with EtOAc (3×50 mL). The combined organic layers were dried ($Na_2SO_4$) and the solvent removed in vacuo. The residue was triturated with $Et_2O$ (10 mL) to afford 1-(4-(3-fluoro-5-(trifluoromethyl)benzyl)pyridin-2-yl)-5-methyl-1H-pyrazole-4-carboxylic acid as brown solid (150 mg, crude). The crude product was used in the next step without further purification.

LCMS (Method 4): m/z 380.3 (ES+), at 1.76 min.

Step 4. HATU (301 mg, 0.791 mmol) and DIPEA (0.37 mL, 1.98 mmol) were added to a solution of 1-(4-(3-fluoro-5-(trifluoromethyl)benzyl)pyridin-2-yl)-5-methyl-1H-pyrazole-4-carboxylic acid (150 mg, 0.395 mmol) in DMF (5 mL) at 0° C. The reaction mixture was stirred for 15 min at same temperature and ammonium chloride (106 mg, 1.98 mmol) was added. The reaction mixture was stirred at RT for 16 h. The reaction mixture was diluted with EtOAc (20 mL) and washed with ice cold water (20 mL). The organic layer was separated and the aqueous layer was extracted with EtOAc (2×20 mL). The organic layers were combined, washed with brine, dried ($Na_2SO_4$) and the solvent removed in vacuo. The residue was purified by gradient flash column chromatography eluting with 0-10% MeOH in DCM to afford 1-(4-(3-fluoro-5-(trifluoromethyl)benzyl)pyridin-2-yl)-5-methyl-1H-pyrazole-4-carboxamide as an off white solid (30 mg, 20%). Data in table 3.

Procedure 5

Example 11, 1-(2-(3-fluoro-5-(trifluoromethyl)benzyl)pyridin-4-yl)-3-methoxy-1H-pyrazole-4-carboxamide

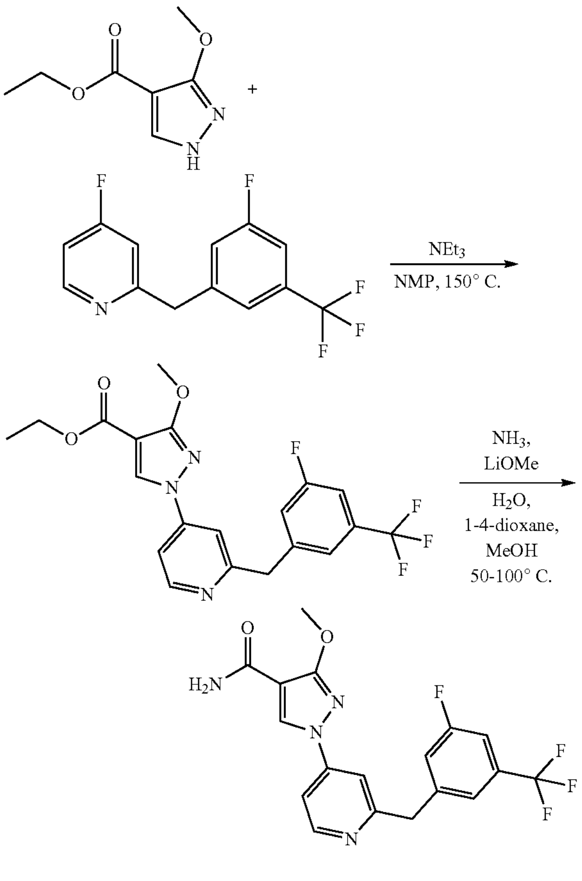

Step 1. Ethyl 1-(2-(3-fluoro-5-(trifluoromethyl)benzyl)pyridin-4-yl)-3-methoxy-1H-pyrazole-4-carboxylate (36 mg, 46%) was prepared from 4-fluoro-2-(3-fluoro-5-(trifluoromethyl)benzyl)pyridine (50 mg, 0.18 mmol), ethyl-3-methoxy-1H-pyazole-4-carboxylate (62 mg, 0.37 mmol) and triethylamine (0.15 mL, 1.10 mmol) in NMP (1.8 mL) heated at 160° C. for 26 h using the methods of Procedure 1. The residue was purified by gradient flash column chromatography eluting with 0-100% EtOAc in i-hexane to yield the product.

LCMS (Method 6): m/z 424.2 (ES+), at 2.45 min.

$^1$H NMR: (400 MHz, DMSO-d) 5: 9.12 (s, 1H), 8.56 (dd, J=5.6, 0.6 Hz, 1H), 7.96 (dd, J=2.2, 0.6 Hz, 1H), 7.76 (dd, J=5.6, 2.3 Hz, 1H), 7.59 (td, J=1.5, 0.8 Hz, 1H), 7.57-7.50 (m, 2H), 4.30-4.20 (m, 4H), 4.00 (s, 3H), 1.29 (t, J=7.1 Hz, 3H).

Step 2. Ammonium hydroxide solution (28% in $H_2O$, 3 mL) was added to a suspension of ethyl 1-(2-(3-fluoro-5-(trifluoromethyl)benzyl)pyridin-4-yl)-3-methoxy-1H-pyrazole-4-carboxylate (15 mg, 0.04 mmol) in MeOH (1.5 mL). The reaction mixture was heated at 50° C. for 16 h. Further ammonium hydroxide solution (28% in $H_2O$, 1 mL) was added and the reaction mixture was heated at 80° C. for 3 h. The solvent was removed in vacuo, the residue dissolved in $NH_3$ in 1,4-dioxane solution (0.5 M, 3 mL) and the reaction mixture heated at 90° C. for 16 h. Ammonium hydroxide solution (28% in $H_2O$, 1 mL) was added and the reaction mixture heated at 100° C. for 4 h. The solvent was removed in vacuo and the residue dissolved in $NH_3$ in MeOH solution (7 N, 2.5 mL) and 1,4-dioxane (1 mL). The reaction mixture was heated at 100° C. for 18 h. Lithium methoxide (18 mg, 0.47 mmol) and further $NH_3$ in MeOH solution (7 N, 2.5 mL) were added and reaction mixture was heated at 100° C. for 68 h. The solvent was removed in vacuo and the residue purified by prep HPLC (Method 1-5-95% gradient) to afford 1-(2-(3-fluoro-5-(trifluoromethyl)benzyl)pyridin-4-yl)-3-methoxy-1H-pyrazole-4-carboxamide (3 mg, 18%). Data in table 3.

Procedure 6

Example 12, 2-(2-(3-fluoro-5-(trifluoromethyl)benzyl)pyridin-4-yl)-5-methyl-2H-1,2,3-triazole-4-carboxamide

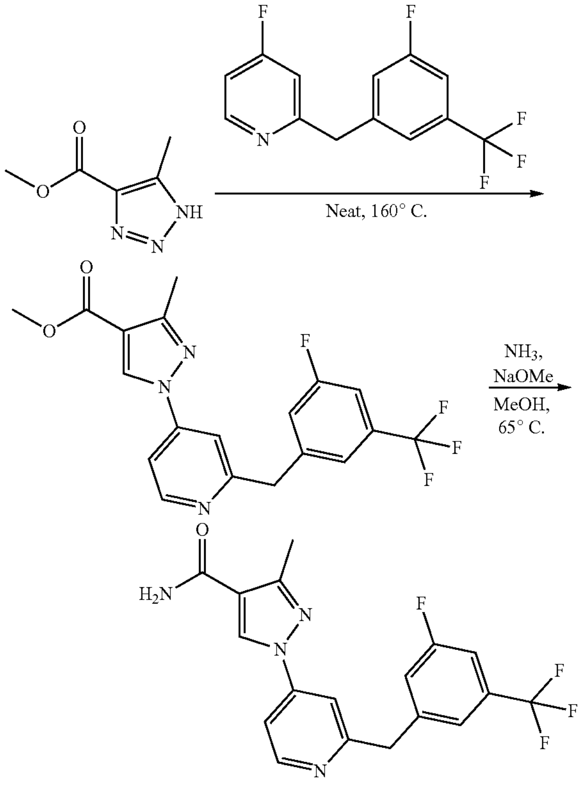

Step 1. Methyl 2-(2-(3-fluoro-5-(trifluoromethyl)benzyl)pyridin-4-yl)-5-methyl-2H-1,2,3-triazole-4-carboxylate (30 mg, 42%) was prepared from 4-fluoro-2-(3-fluoro-5-(trifluoromethyl)benzyl)pyridine (Intermediate 2, 50 mg, 0.18 mmol) and methyl 5-methyl-1H-1,2,3-triazole-4-carboxylate (31 mg, 0.22 mmol) heated at 160° C. for 72 h using the methods of Procedure 3, step 1. The residue was purified by gradient flash column chromatography eluting with 0-50% EtOAc in i-hexane to yield the product.

LCMS (Method 6): m/z 395.1 (ES+), at 2.47 min.

$^1$H NMR: (400 MHz, $CDCl_3$) δ: 8.61 (dd, J=5.5, 0.7 Hz, 1H), 7.94-7.75 (m, 2H), 7.30 (td, J=1.6, 0.8 Hz, 1H), 7.13 (tt, J=8.7, 2.1 Hz, 2H), 4.19 (s, 2H), 3.93 (s, 3H), 2.55 (s, 3H).

Step 2. Methyl 2-(2-(3-fluoro-5-(trifluoromethyl)benzyl)pyridin-4-yl)-5-methyl-2H-1,2,3-triazole-4-carboxylate (23 mg, 0.06 mmol) was added to $NH_3$ in MeOH solution (7 N, 1.6 mL) and sodium methoxide in MeOH solution (0.4 M, 0.16 mL, 0.06 mmol). The reaction mixture was heated at 65° C. for 18 h. The solvent was removed in vacuo and the residue was purified by gradient flash chromatography eluting with 0-100% DCM/MeOH/2M $NH_3$ in MeOH (89:10:1) in DCM to afford 2-(2-(3-fluoro-5-(trifluoromethyl)benzyl)pyridin-4-yl)-5-methyl-2H-1,2,3-triazole-4-carboxamide as a white solid (17 mg, 77%). Data in table 3.

Procedure 7

Example 14, 1-(4-(3-fluoro-5-(trifluoromethyl)benzyl)pyridin-2-yl)-3-methoxy-1H-pyrazole-4-carboxamide

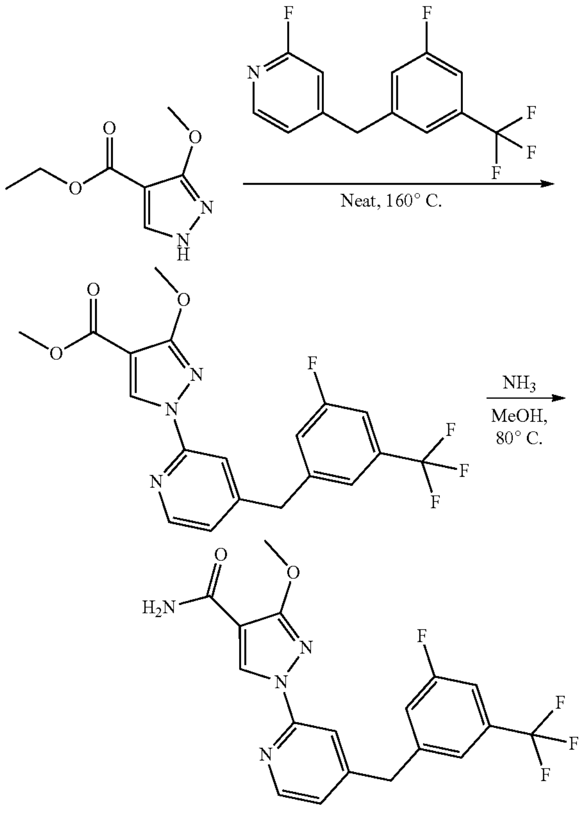

Step 1. Ethyl 1-(4-(3-fluoro-5-(trifluoromethyl)benzyl)pyridin-2-yl)-3-methoxy-1H-pyrazole-4-carboxylate (44 mg, 28%) was prepared from 2-fluoro-4-(3-fluoro-5-(trifluoromethyl)benzyl)pyridine (Intermediate 1, 100 mg, 0.37 mmol) and ethyl 3-methoxy-1H-pyrazole-4-carboxylate (62 mg, 0.37 mmol) heated at 160° C. for 29 h using the methods of Procedure 3, step 1. The residue was purified by gradient flash column chromatography eluting with 0-10% MeOH in DCM to yield the product.

LCMS (Method 6): m/z 424.1 (ES+), at 2.63 min.

$^1$H NMR: (400 MHz, $CDCl_3$) δ: 8.87 (s, 1H), 8.32 (dd, J=5.0, 0.7 Hz, 1H), 7.71 (dt, J=1.6, 0.7 Hz, 1H), 7.30 (dd, J=1.9, 1.1 Hz, 1H), 7.24 (d, J=8.3 Hz, 1H), 7.09 (d, J=8.8 Hz, 1H), 6.96 (ddd, J=5.1, 1.5, 0.7 Hz, 1H), 4.32 (q, J=7.1 Hz, 2H), 4.10 (s, 2H), 4.09 (s, 3H), 1.35 (t, J=7.1 Hz, 3H).

Step 2. $NH_3$ in MeOH solution (7 N, 2.9 mL) was added to ethyl 1-(4-(3-fluoro-5-(trifluoromethyl)benzyl)pyridin-2-yl)-3-methoxy-1H-pyrazole-4-carboxylate (44 mg, 0.10 mmol) and the reaction mixture was heated at 80° C. for 72 h. The solvent was removed in vacuo and the residue was purified by gradient flash chromatography eluting with 0-10% MeOH in DCM to afford 1-(4-(3-fluoro-5-(trifluoromethyl)benzyl)pyridin-2-yl)-3-methoxy-1H-pyrazole-4-carboxamide as a white solid (7 mg, 17%). Data in table 3.

Procedure 8

Example 16, (1-(2-(3-fluoro-5-(trifluoromethyl)benzyl)pyridin-4-yl)-3-methyl-1H-pyrazol-4-yl)(pyrrolidin-1-yl)methanone

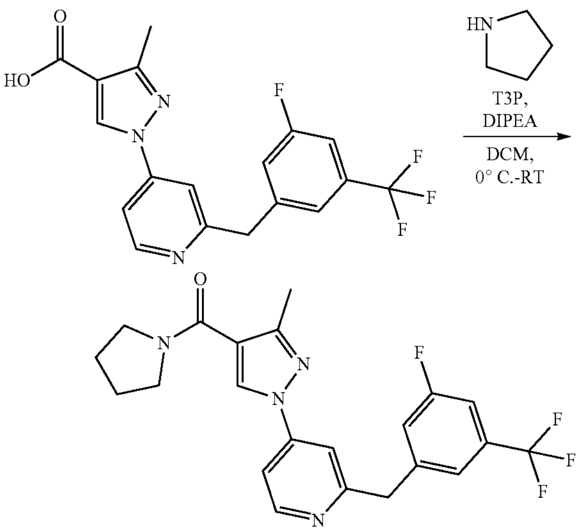

DIPEA (0.09 mL, 0.52 mmol) was added to a solution of 1-(2-(3-fluoro-5-(trifluoromethyl)benzyl)pyridin-4-yl)-3-methyl-1H-pyrazole-4-carboxylic acid (Intermediate 4, 50 mg, 0.13 mmol) and pyrrolidine (28 mg, 0.39 mmol) in DCM (1.3 mL) at 0° C. The reaction mixture was stirred at 0° C. for 10 min and T3P (0.16 mL, 0.26 mmol, 50% solution in EtOAc) was added to it. The reaction mixture was stirred at RT for 16 h. Water (5 mL) was added to the reaction mixture and the aqueous layer was extracted with DCM (2×10 mL). The combined organic layers were dried ($Na_2SO_4$) and the solvent removed in vacuo. The residue was purified by prep HPLC (Method 2-10-80% gradient) to afford (1-(2-(3-fluoro-5-(trifluoromethyl)benzyl)pyridin-4-yl)-3-methyl-1H-pyrazol-4-yl)(pyrrolidin-1-yl)methanone as a white solid (15 mg, 27%). Data in table 3.

Procedure 9

Example 20, 1-(2-(3-fluoro-5-(trifluoromethyl)benzyl)pyridin-4-yl)-N-(2-hydroxyethyl)-3-methyl-1H-pyrazole-4-carboxamide

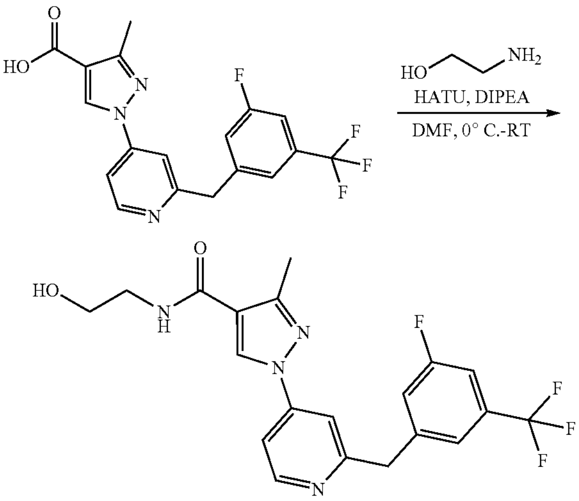

DIPEA (0.09 mL, 0.52 mmol) and HATU (62 mg, 0.26 mmol) were sequentially added to a stirred solution of 1-(2-(3-fluoro-5-(trifluoromethyl)benzyl)pyridin-4-yl)-3-methyl-1H-pyrazole-4-carboxylic acid (Intermediate 4, 50 mg, 0.13 mmol) in DMF (2 mL) at 0° C. After 10 min 2-aminoethan-1-ol (16 mg, 0.26 mmol) was added at 0° C. The reaction mixture was stirred at RT for 16 h. The reaction mixture was diluted with ethyl acetate (20 mL) and washed with ice cold water (20 mL). The organic layer was separated and the aqueous layer was extracted with ethyl acetate (2×20 mL). The organic layers were combined, washed with brine (50 mL), dried ($Na_2SO_4$) and the solvent removed in vacuo. The residue was purified by prep HPLC (Method 2-20-80% gradient) to afford 1-(2-(3-fluoro-5-(trifluoromethyl)benzyl)pyridin-4-yl)-N-(2-hydroxyethyl)-3-methyl-1H-pyrazole-4-carboxamide as a white solid (5 mg, 9%). Data in table 3.

Procedure 10

Example 22, 3-chloro-1-(2-(3-fluoro-5-(trifluoromethyl)benzyl)pyridin-4-yl)-1H-pyrazole-4-carboxamide

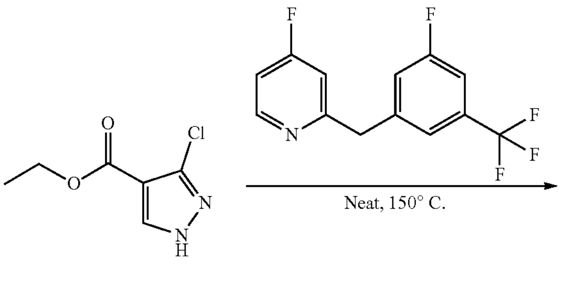

-continued

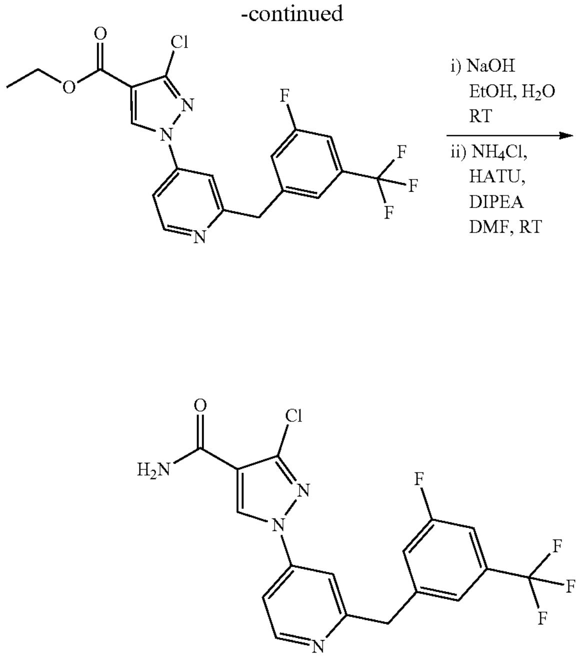

Step 1. 4-fluoro-2-(3-fluoro-5-(trifluoromethyl)benzyl) pyridine (Intermediate 2, 150 mg, 0.55 mmol) and ethyl 3-chloro-1H-pyrazole-4-carboxylate (125 mg, 0.71 mmol) were added together and then heated at 150° C. for 30 min. The reaction mixture was allowed to cool to RT and was purified by gradient flash chromatography eluting with 0-80% EtOAc in i-hexane to afford ethyl 3-chloro-1-(2-(3-fluoro-5-(trifluoromethyl)benzyl)pyridin-4-yl)-1H-pyrazole-4-carboxylate (180 mg, 77%).

LCMS (Method 8): m/z 428.2 (ES+), at 1.85 min.

$^1$H NMR: (400 MHz, $CDCl_3$) δ: 8.69 (dd, J=5.6, 0.6 Hz, 1H), 8.10 (s, 1H), 7.61 (dd, J=2.2, 0.7 Hz, 1H), 7.51 (dd, J=5.6, 2.2 Hz, 1H), 7.37 (tt, J=1.4, 0.7 Hz, 1H), 7.26-7.16 (m, 2H), 4.37 (q, J=7.1 Hz, 2H), 4.28 (s, 2H), 1.40 (t, J=7.1 Hz, 3H).

Step 2. Ethyl 3-chloro-1-(2-(3-fluoro-5-(trifluoromethyl) benzyl)pyridin-4-yl)-1H-pyrazole-4-carboxylate (180 mg, 0.42 mmol) was dissolved in EtOH (5 mL). Sodium hydroxide (1 N in water, 2 mL, 2.0 mmol) was added and the reaction mixture stirred at RT overnight. The reaction mixture was partitioned between EtOAc (30 mL) and 1N HCl (20 mL). The organic layer was separated, dried ($MgSO_4$) and the solvent removed in vacuo. The residue was dissolved in DMF (5 mL). HATU (481 mg, 1.26 mmol), ammonium chloride (68 mg, 1.26 mmol) and DIPEA (0.22 mL, 1.26 mmol) were added and the reaction mixture stirred at RT overnight. The reaction mixture was partitioned between EtOAc (50 mL) and water (50 mL). The organic layer was separated, washed with water (30 mL), brine (20 mL), dried ($MgSO_4$) and the solvent removed in vacuo. The residue was purified by was purified by gradient flash chromatography eluting with 0-8% MeOH in DCM. The residue was further purified by prep HPLC (Method 1-35-65% gradient) to afford 3-chloro-1-(2-(3-fluoro-5-(trifluoromethyl)benzyl)pyridin-4-yl)-1H-pyrazole-4-carboxamide as a white solid (74 mg, 44%). Data in table 3.

Procedure 11

Example 39, 1-(4-(3-fluoro-5-(trifluoromethyl)benzyl)pyridin-2-yl)-5-(hydroxymethyl)-3-methyl-1H-pyrazole-4-carboxamide

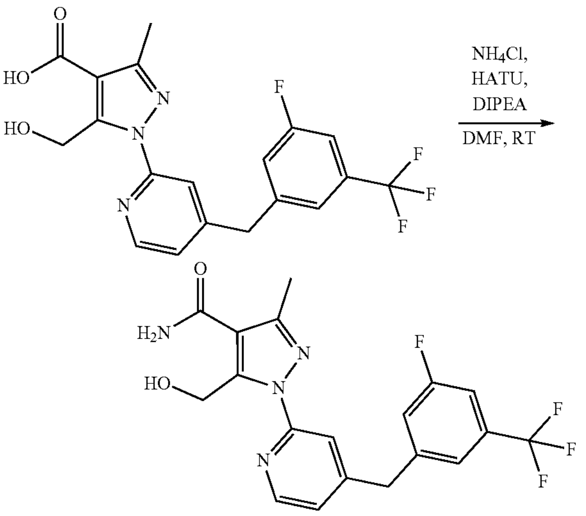

DIPEA (3.06 mL, 17.68 mmol) was added to a stirred solution of 1-(4-(3-fluoro-5-(trifluoromethyl)benzyl)pyridin-2-yl)-5-(hydroxymethyl)-3-methyl-1H-pyrazole-4-carboxylic acid (Intermediate 17, 1.81 g, 4.42 mmol) and ammonium chloride (0.354 g, 6.63 mmol) in DMF (50 mL) followed by the addition of HATU (3.36 g, 8.84 mmol) and the resultant reaction mixture was stirred at RT for 16 h. The reaction mixture was partitioned between EtOAc (100 mL) and water (100 mL). The organic layer was separated and the aqueous layer extracted with EtOAc (100 mL). The combined organic layers were washed with brine (50 mL), dried ($Na_2SO_4$) and the solvent removed in vacuo. The residue was purified by gradient flash column chromatography eluting with 0-85% EtOAc in pet-ether. The compound was dissolved in MeOH (35 mL) and heated to reflux. The resultant clear solution was allowed to cool to RT and kept undisturbed for 48 h. The recrystalised solid was filtered, rinsed with MeOH (2×10 mL) and dried in vacuo to afford 1-(4-(3-fluoro-5-(trifluoromethyl)benzyl)pyridin-2-yl)-5-(hydroxymethyl)-3-methyl-1H-pyrazole-4-carboxamide as a white crystalline solid (0.52 g). From the remaining mother liquor, the recrystallisation process was repeated to obtain a further 0.208 g of material. Combined yield 0.728 g, 40%.

Data in table 3.

Procedure 12

Example 40, 1-(4-(3-fluoro-5-(trifluoromethyl)benzyl)pyridin-2-yl)-N-(2-hydroxyethyl)-5-(hydroxymethyl)-3-methyl-1H-pyrazole-4-carboxamide

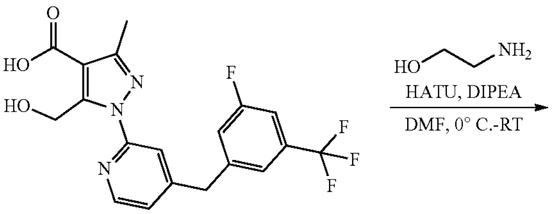

-continued

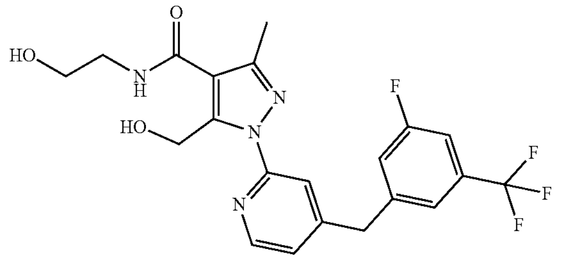

HATU (0.11 g, 0.293 mmol) was added to a stirred solution of 1-(4-(3-fluoro-5-(trifluoromethyl)benzyl)pyridin-2-yl)-5-(hydroxymethyl)-3-methyl-1H-pyrazole-4-carboxylic acid (Intermediate 17, 0.06 g, 0.15 mmol) and 2-aminoethan-1-ol (0.012 g, 0.22 mmol) in DMF (3 mL) at 0° C. followed by the addition of DIPEA (0.038 mg, 0.29 mmol) and the resultant reaction mixture was stirred at RT for 16 h. The reaction mixture was partitioned between EtOAc (30 mL) and water (30 mL). The organic layer was separated and washed with brine (50 mL), dried ($Na_2SO_4$) and the solvent removed in vacuo. The residue was purified by gradient flash column chromatography eluting with 0-50% EtOAc in pet-ether to afford 1-(4-(3-fluoro-5-(trifluoromethyl)benzyl)pyridin-2-yl)-N-(2-hydroxyethyl)-5-(hydroxymethyl)-3-methyl-1H-pyrazole-4-carboxamide as a white solid (18 mg, 27%). Data in table 3.

Procedure 13

Example 47, 1-(6-(3-fluoro-5-(trifluoromethyl)benzyl)pyridin-2-yl)-3-(hydroxymethyl)-11H-pyrazole-4-carboxamide

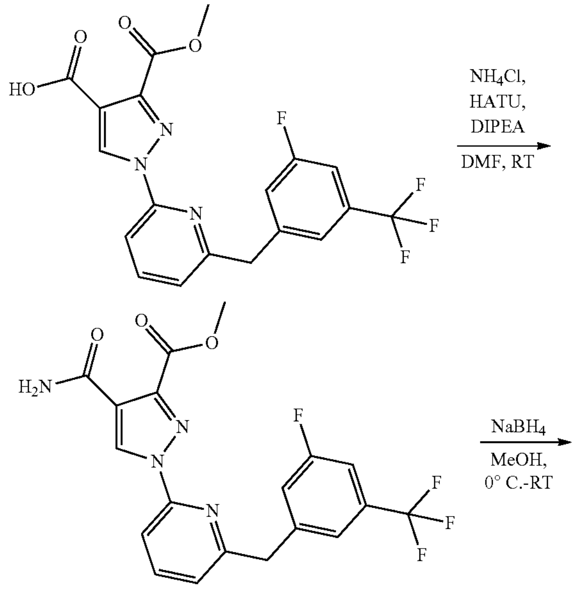

-continued

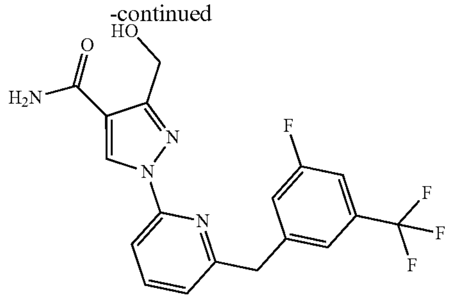

Step 1. DIPEA (0.279 mL, 1.61 mmol) was added to a stirred solution of 1-(6-(3-fluoro-5-(trifluoromethyl)benzyl)pyridin-2-yl)-3-(methoxycarbonyl)-1H-pyrazole-4-carboxylic acid (Intermediate 20, 0.17 g, 0.40 mmol)) and ammonium chloride (0.021 g, 0.40 mmol) in DMF (30 mL) followed by the addition of HATU (0.305 g, 0.80 mmol). The reaction mixture was stirred at RT for 16 h. The reaction mixture was quenched with ice cold water (30 mL). The solid which precipitated out was filtered, washed with water (2×20 mL) and dried in vacuo to afford methyl 4-carbamoyl-1-(6-(3-fluoro-5-(trifluoromethyl)benzyl)pyridin-2-yl)-1H-pyrazole-3-carboxylate as a white solid (0.165 g, 97%).

LCMS (Method 1): m/z 423.0 (ES+), at 2.26 min.

$^1$H NMR: (400 MHz, DMSO-$d_6$) δ: 9.02 (s, 1H), 9.00 (s, 1H), 8.03 (t, J=8.0 Hz, 1H), 7.84 (d, J=7.6 Hz, 1H), 7.66 (s, 1H), 7.61 (d, J=8.8 Hz, 1H), 7.56-7.54 (m, 2H), 7.46 (d, J=7.2 Hz, 1H), 4.32 (s, 2H), 3.90 (s, 3H).

Step 2. Sodium borohydride (0.076 g, 2.01 mmol) was added to a stirred solution of methyl 4-carbamoyl-1-(6-(3-fluoro-5-(trifluoromethyl)benzyl)pyridin-2-yl)-1H-pyrazole-3-carboxylate (0.17 g, 0.40 mmol) in MeOH (30 mL) at 0° C. The reaction mixture was stirred at RT for 16 h. The solvent was removed in vacuo. The residue was dissolved in water (40 mL) and extracted with DCM (40 mL). The organic layer was removed and the aqueous layer extracted with DCM (40 mL). The combined organic layers were separated and washed with brine (50 mL), dried ($Na_2SO_4$) and the solvent removed in vacuo. The residue was purified by gradient flash column chromatography eluting with 0-58% EtOAc in pet-ether to afford 1-(6-(3-fluoro-5-(trifluoromethyl)benzyl)pyridin-2-yl)-3-(hydroxymethyl)-1H-pyrazole-4-carboxamide as a white solid (0.112 g, 70%). Data in table 3.

Procedure 14

Example 53, 1-(4-(3-fluoro-5-(trifluoromethyl)benzyl)pyridin-2-yl)-3-(hydroxymethyl)-5-methyl-1H-pyrazole-4-carboxamide; Example 39, 1-(4-(3-fluoro-5-(trifluoromethyl)benzyl)pyridin-2-yl)-5-(hydroxymethyl)-3-methyl-1H-pyrazole-4-carboxamide

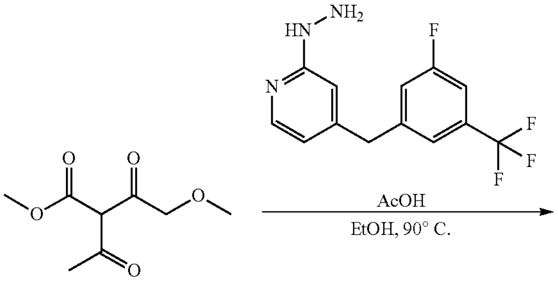

-continued

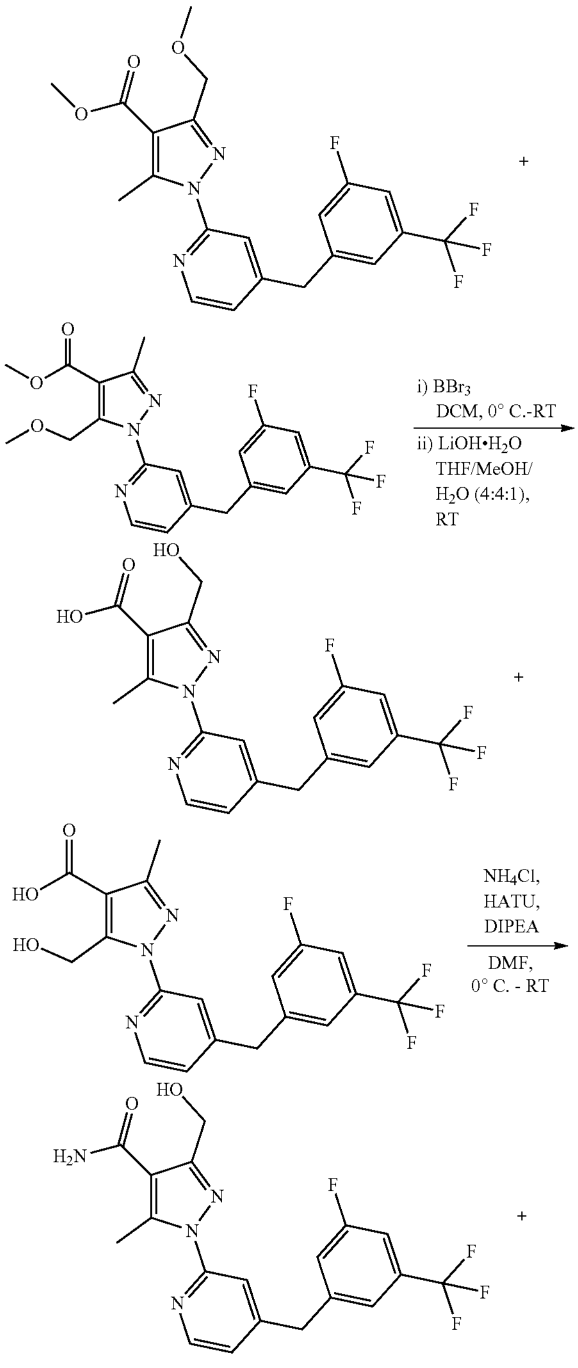

Example 53

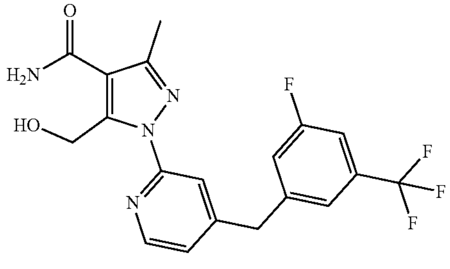

Example 39

Step 1. 4-(3-Fluoro-5-(trifluoromethyl)benzyl)-2-hydrazineylpyridine (Intermediate 3, 1.5 g, 5.26 mmol) and acetic acid (0.03 mL, 0.526 mmol) were added to a stirred solution of methyl 2-acetyl-4-methoxy-3-oxobutanoate (Intermediate 11, 0.99 g, 5.26 mmol) in EtOH (15 mL) and the resultant reaction mixture was heated at 90° C. for 16 h. The solvent was removed in vacuo. The residue was partitioned between water (50 mL) and EtOAc (50 mL). The organic layer was removed and the aqueous layer was extracted with EtOAc (50 mL). The combined organic layers were washed with brine (50 mL), dried ($Na_2SO_4$) and the solvent removed in vacuo. The residue was purified by gradient flash column chromatography eluting with 0-30% EtOAc in pet-ether to afford mixture of regioisomers methyl 1-(4-(3-fluoro-5-(trifluoromethyl)benzyl)pyridin-2-yl)-3-(methoxymethyl)-5-methyl-1H-pyrazole-4-carboxylate and methyl 1-(4-(3-fluoro-5-(trifluoromethyl)benzyl)pyridin-2-yl)-5-(methoxymethyl)-3-methyl-1H-pyrazole-4-carboxylate as a red gum (0.25 g, 10%).

LCMS (Method 1): m/z 438.0 (ES+), at 2.64 min.

Step 2. $BBr_3$ (1 M in DCM, 5.72 mL, 5.72 mmol) was added to a stirred solution of a mixture of methyl 1-(4-(3-fluoro-5-(trifluoromethyl)benzyl)pyridin-2-yl)-3-(methoxymethyl)-5-methyl-1H-pyrazole-4-carboxylate and methyl 1-(4-(3-fluoro-5-(trifluoromethyl)benzyl)pyridin-2-yl)-5-(methoxymethyl)-3-methyl-1H-pyrazole-4-carboxylate (0.25 g, 0.572 mmol) in DCM (5 mL) at 0° C. and the resultant reaction mixture was stirred at RT for 16 h. The solvent was removed in vacuo. The residue was partitioned between water (30 mL) and EtOAc (30 mL). The organic layer was removed and the aqueous layer was extracted with EtOAc (30 mL). The combined organic layers were washed with brine (20 mL), dried ($Na_2SO_4$) and the solvent removed in vacuo. The residue was dissolved in THF (2 mL), MeOH (2 mL) and water (0.5 mL), lithium hydroxide monohydrate (41 mg, 0.99 mmol) was added and the resultant reaction mixture was stirred at RT for 3 h. The solvent was removed in vacuo. The residue was dissolved in water (30 mL) and acidified with 2 N HCl to pH ~2. The aqueous layer was extracted with EtOAc (4×50 mL). The combined organic layers were washed with brine (50 mL), dried ($Na_2SO_4$) and the solvent removed in vacuo to afford a mixture of regioisomers 1-(4-(3-fluoro-5-(trifluoromethyl)benzyl)pyridin-2-yl)-3-(hydroxymethyl)-5-methyl-1H-pyrazole-4-carboxylic acid and 1-(4-(3-fluoro-5-(trifluoromethyl)benzyl)pyridin-2-yl)-5-(hydroxymethyl)-3-methyl-1H-pyrazole-4-carboxylic acid as an off-white solid (0.2 g, crude). The crude product was used in the next step without further purification.

LCMS (Method 11): m/z 409.9 (ES+), at 2.36 and 2.40 min.

Step 3. HATU (0.279 g, 0.735 mmol) was added to a stirred solution of a mixture of 1-(4-(3-fluoro-5-(trifluoromethyl)benzyl)pyridin-2-yl)-3-(hydroxymethyl)-5-methyl-1H-pyrazole-4-carboxylic acid and 1-(4-(3-fluoro-5-(trifluoromethyl)benzyl)pyridin-2-yl)-5-(hydroxymethyl)-3-methyl-1H-pyrazole-4-carboxylic acid (0.2 g, 0.49 mmol) and $NH_4Cl$ (0.033 g, 0.62 mmol) in DMF (5 mL) followed by the addition of DIPEA (0.21 mL, 0.12 mmol) at 0° C. and the resultant reaction mixture was stirred at RT for 16 h. The reaction mixture was partitioned between EtOAc (30 mL) and water (30 mL). The organic layer was separated, washed with brine (30 mL), dried ($Na_2SO_4$) and the solvent removed in vacuo. The residue was purified by prep HPLC (Method 3) to afford 1-(4-(3-fluoro-5-(trifluoromethyl)benzyl)pyridin-2-yl)-3-(hydroxymethyl)-5-methyl-1H-pyrazole-4-carboxamide (Example 53, 11 mg, 5%) and 1-(4-(3-fluoro-5-

(trifluoromethyl)benzyl)pyridin-2-yl)-5-(hydroxymethyl)-3-methyl-1H-pyrazole-4-carboxamide (Example 39, 22 mg, 11%) as a white solids. Data in table 3.

Procedure 15

Example 59, 1-(2-((3-fluoro-5-(trifluoromethyl)phenyl)(hydroxy)methyl)pyridin-4-yl)-3-methyl-1H-pyrazole-4-carboxamide

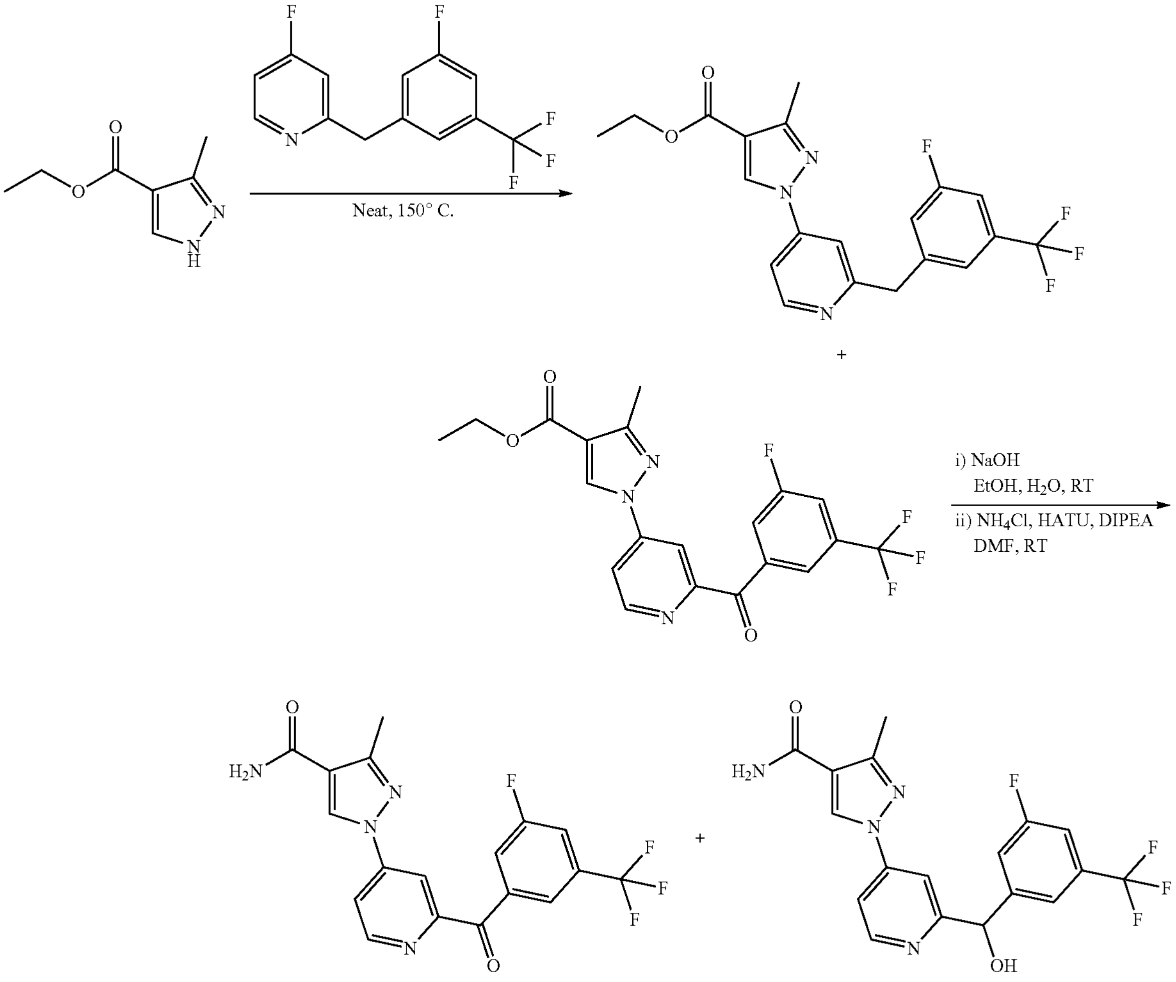

Example 59

Step 1. 4-Fluoro-2-(3-fluoro-5-(trifluoromethyl)benzyl)pyridine (Intermediate 2, 300 mg, 1.10 mmol) and ethyl 3-methyl-1H-pyrazole-4-carboxylate (169 mg, 1.10 mmol) were heated at 150° C. for 5 days. The residue was purified by gradient flash column chromatography eluting with 0-80% EtOAc in i-hexane to afford ethyl 1-(2-(3-fluoro-5-(trifluoromethyl)benzyl)pyridin-4-yl)-3-methyl-1H-pyrazole-4-carboxylate (Product 1, 150 mg, 34%) and ethyl 1-(2-(3-fluoro-5-(trifluoromethyl)benzoyl)pyridin-4-yl)-3-methyl-1H-pyrazole-4-carboxylate (Product 2, 300 mg, 65%).

Product 2:

LCMS (Method 8): m/z 422.2 (ES+), at 1.92 min.

Step 2. Sodium hydroxide (1 N in water, 2 mL, 2.0 mmol) was added to a solution of ethyl 1-(2-(3-fluoro-5-(trifluoromethyl)benzoyl)pyridin-4-yl)-3-methyl-1H-pyrazole-4-carboxylate (300 mg, 0.71 mmol) in EtOH (5 mL) and the reaction mixture stirred at RT for 16 h. The solvent was removed in vacuo and the residue was partitioned between EtOAc (30 mL) and 1 N HCl (20 ml). The organic layer was separated, dried ($MgSO_4$) and the solvent removed in vacuo. The residue was dissolved in DMF (5 mL). HATU (814 mg, 2.14 mmol), ammonium chloride (114 mg, 2.14 mmol) and DIPEA (0.37 mL, 2.14 mmol) were added and the reaction mixture stirred at RT for 3 h. The reaction mixture was partitioned between EtOAc (50 mL) and water (50 mL). The organic layer was separated, washed with water (30 mL), brine (20 mL), dried ($MgSO_4$) and the solvent removed in vacuo. The residue was purified by flash column chromatography eluting with 0-8% MeOH in DCM to afford 1-(2-(3-fluoro-5-(trifluoromethyl)benzoyl)pyridin-4-yl)-3-methyl-1H-pyrazole-4-carboxamide and 1-(2-((3-fluoro-5-(trifluoromethyl)phenyl)(hydroxy)methyl)pyridin-4-yl)-3-methyl-1H-pyrazole-4-carboxamide (Example 59). The 1-(2-((3-fluoro-5-(trifluoromethyl)phenyl)(hydroxy)methyl)pyridin-4-yl)-3-methyl-1H-pyrazole-4-carboxamide obtained was further purified by prep HPLC (Method 1-25-50% gradient) to afford a white solid (33 mg, 12%). Data in table 3.

Further examples prepared by the above procedures are detailed in Table 3.

TABLE 3

Examples table

| Ex. No. | Name | Intermediate/ procedure | $^1$H NMR | LCMS |
|---|---|---|---|---|
| 1 | 1-(4-(3-fluoro-5-(trifluoromethyl)benzyl) pyridin-2-yl)-1H-pyrazole-4-carboxamide | Intermediate 1 and CAS: 437701-80-9 Procedure 1 | (400 MHz, DMSO-$d_6$) δ: 9.11 (d, J = 0.8 Hz, 1H), 8.43 (dd, J = 5.1, 0.7 Hz, 1H), 8.12 (d, J = 0.7 Hz, 1H), 7.91 (dd, J = 1.6, 0.8 Hz, 1H), 7.82 (s, 1H), 7.66 (s, 1H), 7.63-7.52 (m, 2H), 7.36 (dd, J = 5.1, 1.5 Hz, 1H), 7.23 (s, 1H), 4.24 (s, 2H). | m/z 365.6 (M + H)+ (ES+), at 4.15 min, 96% (Method 3) |
| 2 | 1-(2-(3-fluoro-5-(trifluoromethyl)benzyl) pyridin-4-yl)-1H-pyrazole-4-carboxamide | Intermediate 2 and CAS: 437701-80-9 Procedure 1 | (400 MHz, Methanol-$d_4$) δ: 8.88 (s, 1H), 8.59 (d, J = 5.6 Hz, 1H), 8.17 (s, 1H), 7.88 (d, J = 2.0 Hz, 1H), 7.76 (dd, J = 5.6, 2.2 Hz, 1H), 7.49 (s, 1H), 7.37 (dd, J = 9.4, 2.1 Hz, 1H), 7.31 (dd, J = 8.7, 2.1 Hz, 1H), 4.31 (s, 2H). 2 exchangeable protons not observed. | m/z 363.3 (M − H)− (ES-), 365.2 (M + H)+ (ES+), at 3.75 min, 100% (Method 3) |
| 3 | 1-(4-(3-fluoro-5-(trifluoromethyl)benzyl) pyridin-2-yl)-N-methyl-1H-pyrazole-4-carboxamide | Intermediate 1 and CAS: 51105-90-9 Procedure 2 | (400 MHz, DMSO-$d_6$) δ: 9.06 (s, 1H), 8.43 (d, J = 5.1 Hz, 1H), 8.31 (d, J = 4.8 Hz, 1H), 8.12 (s, 1H), 7.90 (s, 1H), 7.65 (s, 1H), 7.63-7.53 (m, 2H), 7.36 (dd, J = 5.1, 1.4 Hz, 1H), 4.23 (s, 2H), 2.74 (d, J = 4.5 Hz, 3H). | m/z 379.2 (M + H)+ (ES+), at 5.84 min, 94% (Method 2) |
| 4 | 2-(4-(3-fluoro-5-(trifluoromethyl)benzyl) pyridin-2-yl)-2H-1,2,3-triazole-4-carboxamide | Intermediate 1 and CAS: 4967-77-5 Procedure 3 | (400 MHz, DMSO-$d_6$) δ: 8.52 (d, J = 5.0 Hz, 1H), 8.46 (s, 1H), 8.11 (s, 1H), 8.05 (d, J = 1.3 Hz, 1H), 7.74 (s, 1H), 7.66 (s, 1H), 7.64-7.54 (m, 2H), 7.50 (dd, J = 5.0, 1.5 Hz, 1H), 4.27 (s, 2H). | m/z 366.1 (M + H)+ (ES+), at 5.50 min, 97% (Method 2) |
| 5 | 1-(4-(3-fluoro-5-(trifluoromethyl)benzyl) pyridin-2-yl)-3-methyl-1H-pyrazole-4-carboxamide | Intermediate 1 and CAS: 23170-45-8 Procedure 3 | (400 MHz, DMSO-$d_6$) δ: 9.15 (s, 1H), 8.39 (d, J = 5.1 Hz, 1H), 7.88 (s, 1H), 7.79-7.47 (m, 4H), 7.31 (d, J = 5.2 Hz, 1H), 7.08 (s, 1H), 4.22 (s, 2H), 2.44 (s, 3H). | m/z 379.2 (M + H)+ (ES+), at 5.91 min, 99% (Method 2) |
| 6 | 1-(4-(3-fluoro-5-(trifluoromethyl)benzyl) pyridin-2-yl)-3,5-dimethyl-1H-pyrazole-4-carboxamide | Intermediate 1 and CAS: 25016-18-6 Procedure 3 | (400 MHz, DMSO-$d_6$) δ: 8.41 (d, J = 5.0 Hz, 1H), 7.75 (s, 1H), 7.64 (s, 1H), 7.60-7.52 (m, 2H), 7.32 (d, J = 6.0 Hz, 1H), 7.24 (s, 2H), 4.20 (s, 2H), 2.63 (s, 3H), 2.32 (s, 3H). | m/z 393.2 (M + H)+ (ES+), at 5.69 min, 99% (Method 2) |
| 7 | 1-(4-(3-fluoro-5-(trifluoromethyl)benzyl) pyridin-2-yl)-5-methyl-1H-pyrazole-4-carboxamide | Intermediate 3 and CAS: 105-45-3 Procedure 4 | (400 MHz, DMSO-$d_6$) δ: 8.45 (d, J = 5.0 Hz, 1H), 8.12 (s, 1H), 7.76 (s, 1H), 7.70-7.52 (m, 4H), 7.39 (dd, J = 5.2, 1.4 Hz, 1H), 7.10 (s, 1H), 4.22 (s, 2H), 2.77 (s, 3H). | m/z 379.1 (M + H)+ (ES+), at 5.67 min, 99% (Method 2) |
| 8 | 1-(2-(3-fluoro-5-(trifluoromethyl)benzyl) pyridin-4-yl)-3-methyl-1H-pyrazole-4-carboxamide | Intermediate 4 and CAS: 12125-02-9 Procedure 9 | (400 MHz, DMSO-$d_6$) δ: 9.00 (s, 1H), 8.58 (d, J = 5.6 Hz, 1H), 7.81 (d, J = 1.9 Hz, 1H), 7.59-7.56 (m, 2H), 7.53 (d, J = 9.1 Hz, 2H), 7.47 (s, 1H), 7.18 (s, 1H), 4.28 (s, 2H), 2.42 (s, 3H). | m/z 379.2 (M + H)+ (ES+), at 4.98 min, 99% (Method 5) |
| 9 | 1-(4-(3-fluoro-5-(trifluoromethyl)benzyl) pyridin-2-yl)-1H-pyrazole-3-carboxamide | Intermediate 5 and CAS: 12125-02-9 Procedure 9 | (400 MHz, DMSO-$d_6$) δ: 8.63 (d, J = 2.6 Hz, 1H), 8.42 (d, J = 5.1 Hz, 1H), 8.03 (s, 1H), 7.77 (s, 1H), 7.65-7.46 (m, 4H), 7.40-7.24 (m, 1H), 6.89 (d, J = 2.6 Hz, 1H), 4.23 (s, 2H). | m/z 365.2 (M + H)+ (ES+), at 5.77 min, 97% (Method 2) |
| 10 | 1-(4-(3-fluoro-5-(trifluoromethyl)benzyl) pyridin-2-yl)-4-methyl-1H-pyrazole-3-carboxamide | Intermediate 7 and CAS: 12125-02-9 Procedure 9 | (400 MHz, DMSO-$d_6$) δ: 8.44 (d, J = 1.1 Hz, 1H), 8.39 (d, J = 5.1 Hz, 1H), 8.02 (d, J = 1.4 Hz, 1H), 7.69-7.49 (m, 4H), 7.38 (s, 1H), 7.28 (dd, J = 5.1, 1.5 Hz, 1H), 4.21 (s, 2H), 2.26 (s, 3H). | m/z 379.1 (M + H)+ (ES+), at 6.24 min, 99% (Method 2) |
| 11 | 1-(2-(3-fluoro-5-(trifluoromethyl)benzyl) ypridin-4-yl)-3-methoxy-1H-pyrazole-4-carboxamide | Intermediate 2 and CAS: 478968-48-8 Procedure 5 | (400 MHz, Methanol-$d_4$) δ: 8.66 (s, 1H), 8.44 (dd, J = 5.8, 0.6 Hz, 1H), 7.75 (dd, J = 2.2, 0.6 Hz, 1H), 7.62 (dd, J = 5.7, 2.2 Hz, 1H), 7.41 (td, J = 1.6, 0.8 Hz, 1H), 7.35-7.26 (m, 1H), 7.26-7.16 (m, 1H), 4.20 (s, 2H), 4.05 (s, 3H). 2 exchangeable protons not observed. | m/z 395.2 (M + H)+ (ES+), at 3.92 min, 100% (Method 3) |
| 12 | 2-(2-(3-fluoro-5-(trifluoromethyl)benzyl) pyridin-4-yl)-5-methyl-2H-1,2,3-triazole-4-carboxamide | Intermediate 2 and CAS: 60419-70-7 Procedure 6 | (400 MHz, Methanol-$d_4$) δ: 8.53 (dd, J = 5.6, 0.7 Hz, 1H), 7.97 (dq, J = 2.2, 0.7 Hz, 1H), 7.86 (dd, J = 5.6, 2.1 Hz, 1H), 7.39 (qt, J = 1.3, 0.6 Hz, 1H), 7.31-7.25 (m, 1H), 7.24-7.16 (m, 1H), 4.22 (d, J = 8.1 Hz, 2H), 2.48 (s, 3H). 2 exchangeable protons not observed. | m/z 380.1 (M + H)+ (ES+), at 4.25 min, 100% (Method 3) |
| 13 | 2-(4-(3-fluoro-5-(trifluoromethyl)benzyl) pyridin-2-yl)-5-methyl-2H-1,2,3-triazole-4-carboxamide | Intermediate 1 and CAS: 60419-70-7 Procedure 6 | (400 MHz, Methanol-$d_4$) δ: 8.37 (dd, J = 5.1, 0.7 Hz, 1H), 7.96 (dq, J = 1.3, 0.7 Hz, 1H), 7.40 (s, 1H), 7.33-7.19 (m, 3H), 4.16 (d, J = 8.4 Hz, 2H), 2.50 (s, 3H). 2 exchangeable protons not observed. | m/z 380.1 (M + H)+ (ES+), at 4.13 min, 98% (Method 3) |
| 14 | 1-(4-(3-fluoro-5-(trifluoromethyl)benzyl) pyridin-2-yl)-3-methoxy-1H-pyrazole-4-carboxamide | Intermediate 1 and CAS: 478968-48-8 Procedure 7 | (400 MHz, Methanol-$d_4$) δ: 8.77 (s, 1H), 8.24 (dd, J = 5.1, 0.7 Hz, 1H), 7.67 (dq, J = 1.5, 0.7 Hz, 1H), 7.37 (dd, J = 1.8, 1.0 Hz, 1H), 7.31-7.18 (m, 2H), 7.06 (ddd, J = 5.1, 1.4, 0.7 Hz, 1H), 4.11 (s, 2H), 4.02 (s, 3H). 2 exchangeable protons not observed. | m/z 395.2 (M + H)+ (ES+), at 4.52 min, 100% (Method 3) |
| 15 | 1-(6-(3-fluoro-5-(trifluoromethyl)benzyl) pyridin-2-yl)-4-methyl-1H-pyrazole-3-carboxamide | Intermediate 6 and CAS: 6076-12-6 Procedure 6 | (400 MHz, Methanol-$d_4$) δ: 8.27 (q, J = 0.9 Hz, 1H), 7.88-7.69 (m, 2H), 7.44 (dq, J = 1.6, 0.8 Hz, 1H), 7.37-7.26 (m, 1H), 7.21 (dd, J = 8.7, 2.2 Hz, 1H), 7.19-7.12 (m, 1H), 4.16 (s, 2H), 2.24 (d, J = 0.9 Hz, 3H). 2 exchangeable protons not observed. | m/z 379.1 (M + H)+ (ES+), at 4.94 min, 100% (Method 3) |

TABLE 3-continued

Examples table

| Ex. No. | Name | Intermediate/ procedure | $^1$H NMR | LCMS |
|---|---|---|---|---|
| 16 | (1-(2-(3-fluoro-5-(trifluoromethyl)benzyl) pyridin-4-yl)-3-methyl-1H-pyrazol-4-yl)(pyrrolidin-1-yl)methanone | Intermediate 4 and CAS: 123-75-1 Procedure 8 | (400 MHz, DMSO-$d_6$) δ: 8.88 (s, 1H), 8.55 (d, J = 5.6 Hz, 1H), 7.93 (d, J = 2.0 Hz, 1H), 7.74 (dd, J = 2.0 Hz, 5.6 Hz, 1H), 7.57 (s, 1H), 7.52 (d, J = 9.2 Hz, 2H), 4.27 (s, 2H), 3.63 (t, J = 6.0 Hz, 2H), 3.45 (t, J = 6.0 Hz, 2H), 2.37 (s, 3H), 1.83-1.88 (m, 4H). | m/z 433.2 (M + H)+ (ES+), at 5.27 min, 97% (Method 5) |
| 17 | 1-(2-(3-fluoro-5-(trifluoromethyl)benzyl) pyridin-4-yl)-N,3-dimethyl-1H-pyrazole-4-carboxamide | Intermediate 4 and CAS: 593-51-1 Procedure 8 | (400 MHz, DMSO-$d_6$) δ: 8.94 (s, 1H), 8.58 (d, J = 5.6 Hz, 1H), 8.01 (q, J = 4.5 Hz, 1H), 7.83 (d, J = 2.1 Hz, 1H), 7.59 (q, J = 2.5 Hz, 2H), 7.53 (d, J = 9.2 Hz, 2H), 4.28 (s, 2H), 2.74 (d, J = 4.5 Hz, 3H), 2.43 (s, 3H). | m/z 393.2 (M + H)+ (ES+), at 5.01 min, 100% (Method 5) |
| 18 | 1-(2-(3-fluoro-5-(trifluoromethyl)benzyl) pyridin-4-yl)-N,N,3-trimethyl-1H-pyrazole-4-carboxamide | Intermediate 4 and CAS: 124-40-3 Procedure 8 | (400 MHz, DMSO-$d_6$) δ: 8.83 (s, 1H), 8.56 (d, J = 5.6 Hz, 1H), 7.91 (d, J = 2.1 Hz, 1H), 7.71 (dd, J = 5.6, 2.2 Hz, 1H), 7.58 (s, 1H), 7.53 (d, J = 9.3 Hz, 2H), 4.27 (s, 2H), 3.06 (br s, 3H), 3.00 (br s, 3H), 2.30 (s, 3H). | m/z 407.1 (M + H)+ (ES+), at 5.06 min, 98% (Method 5) |
| 19 | 1-(2-(3-fluoro-5-(trifluoromethyl)benzyl) pyridin-4-yl)-3-methyl-N-(oxetan-3-yl)-1H-pyrazole-4-carboxamide | Intermediate 4 and CAS: 21635-88-1 Procedure 8 | (400 MHz, DMSO-$d_6$) δ: 9.05 (s, 1H), 8.77 (d, J = 6.7 Hz, 1H), 8.60 (d, J = 5.6 Hz, 1H), 7.86 (d, J = 2.1 Hz, 1H), 7.69-7.57 (m, 2H), 7.54 (d, J = 9.2 Hz, 2H), 5.08-4.88 (m, 1H), 4.79 (t, J = 6.9 Hz, 2H), 4.53 (t, J = 6.3 Hz, 2H), 4.29 (s, 2H), 2.42 (s, 3H). | m/z 435.2 (M + H)+ (ES+), at 5.02 min, 98% (Method 5) |
| 20 | 1-(2-(3-fluoro-5-(trifluoromethyl)benzyl) pyridin-4-yl)-N-(2-hydroxyethyl)-3-methyl-1H-pyrazole-4-carboxamide | Intermediate 4 and CAS: 141-43-5 Procedure 9 | (400 MHz, DMSO-$d_6$) δ: 9.04 (s, 1H), 8.59 (d, J = 5.6 Hz, 1H), 8.02 (t, J = 5.6 Hz, 1H), 7.84 (d, J = 2.1 Hz, 1H), 7.58 (q, J = 2.4 Hz, 2H), 7.53 (d, J = 9.2 Hz, 2H), 4.75 (t, J = 5.5 Hz, 1H), 4.28 (s, 2H), 3.49 (q, J = 6.0 Hz, 2H), 3.29 (q, J = 6.0 Hz, 2H), 2.43 (s, 3H). | m/z 423.2 (M + H)+ (ES+), at 5.29 min, 99% (Method 2) |
| 21 | 1-(2-(3-fluoro-5-(trifluoromethyl)benzyl) pyridin-4-yl)-N-(2-methoxyethyl)-3-methyl-1H-pyrazole-4-carboxamide | Intermediate 4 and CAS: 109-85-3 Procedure 8 | (400 MHz, DMSO-$d_6$) δ: 9.03 (s, 1H), 8.59 (d, J = 5.6 Hz, 1H), 8.10 (t, J = 5.4 Hz, 1H), 7.84 (d, J = 2.2 Hz, 1H), 7.59 (q, J = 2.5 Hz, 2H), 7.53 (d, J = 9.2 Hz, 2H), 4.29 (s, 2H), 3.44 (dd, J = 6.1, 4.0 Hz, 2H), 3.39 (q, J = 5.2 Hz, 2H), 3.28 (s, 3H), 2.43 (s, 3H). | m/z 437.2 (M + H)+ (ES+), at 5.19 min, 96% (Method 5) |
| 22 | 3-chloro-1-(2-(3-fluoro-5-(trifluoromethyl)benzyl) pyridin-4-yl)-1H-pyrazole-4-carboxamide | Intermediate 2 and CAS: 1393667-83-8 and 12125-02-9 Procedure 10 | (400 MHz, DMSO-$d_6$) δ: 9.16 (s, 1H), 8.63 (dd, J = 5.6, 0.6 Hz, 1H), 7.90 (dd, J = 2.3, 0.6 Hz, 1H), 7.66 (dd, J = 5.6, 2.2 Hz, 1H), 7.59 (tt, J = 1.5, 0.7 Hz, 1H), 7.58-7.43 (m, 4H), 4.30 (s, 2H). | m/z 399.2 (M + H)+ (ES+), at 1.41 min, 98% (Method 8) |
| 23 | 3-(difluoromethyl)-1-(2-(3-fluoro-5-(trifluoromethyl)benzyl) pyridin-4-yl)-1H-pyrazole-4-carboxamide | Intermediate 2 and CAS: 151733-96-9 and 12125-02-9 Procedure 10 | (400 MHz, DMSO-$d_6$) δ: 9.18 (t, J = 1.4 Hz, 1H), 8.68 (dd, J = 5.5, 0.6 Hz, 1H), 7.90 (dd, J = 2.2, 0.7 Hz, 1H), 7.80 (s, 1H), 7.65 (dd, J = 5.6, 2.2 Hz, 1H), 7.60 (tt, J = 1.6, 0.7 Hz, 1H), 7.56-7.49 (m, 2H), 7.43 (t, J = 53.7 Hz, 1H), 4.34 (s, 2H). 1 exchangeable proton not observed. | m/z 415.2 (M + H)+ (ES+), at 1.43 min, 100% (Method 8) |
| 24 | 1-(2-(3-fluoro-5-(trifluoromethyl)benzyl) pyridin-4-yl)-3-(trifluoromethyl)-1H-pyrazole-4-carboxamide | Intermediate 2 and CAS: 155377-19-8 and 12125-02-9 Procedure 10 | (400 MHz, DMSO-$d_6$) δ: 9.24 (q, J = 1.1 Hz, 1H), 8.69 (dd, J = 5.6, 0.6 Hz, 1H), 7.93 (dd, J = 2.2, 0.6 Hz, 1H), 7.80 (s, 1H), 7.70 (dd, J = 5.5, 2.2 Hz, 1H), 7.60 (tt, J = 1.6, 0.8 Hz, 1H), 7.57-7.41 (m, 3H), 4.34 (s, 2H). | m/z 433.2 (M + H)+ (ES+), at 1.50 min, 100% (Method 8) |
| 25 | 3-ethyl-1-(2-(3-fluoro-5-(trifluoromethyl)benzyl) pyridin-4-yl)-1H-pyrazole-4-carboxamide | Intermediate 2 and CAS: 73981-23-4 and 12125-02-9 Procedure 10 | (400 MHz, $CDCl_3$) δ: 8.62 (dd, J = 5.6, 0.6 Hz, 1H), 8.35 (d, J = 0.4 Hz, 1H), 7.55 (dd, J = 2.2, 0.7 Hz, 1H), 7.47 (dd, J = 5.6, 2.1 Hz, 1H), 7.36 (tq, J = 1.5, 0.7 Hz, 1H), 7.24-7.14 (m, 2H), 5.68 (s, 2H), 4.24 (s, 2H), 2.96 (d, J = 7.5 Hz, 2H), 1.36 (t, J = 7.5 Hz, 3H). | m/z 393.2 (M + H)+ (ES+), at 3.95 min, 91% (Method 9) |
| 26 | 3-cyano-1-(2-(3-fluoro-5-(trifluoromethyl)benzyl) pyridin-4-yl)-1H-pyrazole-4-carboxamide | Intermediate 2 and CAS: 119741-57-0 and 12125-02-9 Procedure 10 | (400 MHz, DMSO-$d_6$) δ: 9.29 (s, 1H), 8.72 (dd, J = 5.6, 0.6 Hz, 1H), 7.95 (dd, J = 2.2, 0.7 Hz, 1H), 7.90 (s, 1H), 7.68 (dt, J = 5.4, 2.7 Hz, 2H), 7.60 (dq, J = 1.7, 0.8 Hz, 1H), 7.58-7.49 (m, 2H), 4.34 (s, 2H). | m/z 390.2 (M + H)+ (ES+), at 3.83 min, 100% (Method 9) |
| 27 | 3-cyclopropyl-1-(2-(3-fluoro-5-(trifluoromethyl)benzyl) pyridin-4-yl)-1H-pyrazole-4-carboxamide | Intermediate 2 and CAS: 119741-57-0 and 12125-02-9 Procedure 10 | (400 MHz, DMSO-$d_6$) δ: 8.96 (s, 1H), 8.57 (dd, J = 5.6, 0.6 Hz, 1H), 7.74 (dd, J = 2.2, 0.6 Hz, 1H), 7.57 (td, J = 1.5, 0.8 Hz, 1H), 7.56-7.42 (m, 3H), 7.22 (s, 1H), 4.28 (s, 2H), 2.65 (tt, J = 8.2, 5.2 Hz, 1H), 1.00-0.86 (m, 4H). 1 exchangeable proton not observed. | m/z 405.2 (M + H)+ (ES+), at 4.10 min, 100% (Method 9) |
| 28 | 1-(4-(3-fluoro-5-(trifluoromethyl)benzyl) pyridin-2-yl)-/,5-dimethyl-1H-pyrazole-3-carboxamide | Intermediate 1 and CAS: 4027-57-0 and 74-89-5 Procedure 10 | (400 MHz, $CDCl_3$) δ: 8.40 (dd, J = 5.1, 0.8 Hz, 1H), 7.70 (dt, J = 1.4, 0.7 Hz, 1H), 7.31 (d, J = 2.4 Hz, 2H), 7.10 (d, J = 9.2 Hz, 1H), 7.06-7.02 (m, 1H), 6.71 (q, J = 0.8 Hz, 1H), 4.11 (s, 2H), 2.99 (s, 3H), 2.67 (d, J = 0.8 Hz, 3H). 1 exchangeable proton not observed. | m/z 393.3 (M + H)+ (ES+), at 1.74 min, 96% (Method 10) |

TABLE 3-continued

| Ex. No. | Name | Intermediate/ procedure | $^1$H NMR | LCMS |
|---|---|---|---|---|
| Examples table | | | | |
| 29 | 1-(2-(3-fluoro-5-(trifluoromethyl)benzyl) pyridin-4-yl)-1H-pyrazole-3-carboxamide | Intermediate 8 and CAS: 12125-02-9 Procedure 9 | (400 MHz, DMSO-$d_6$) δ: 8.72 (d, J = 2.6 Hz, 1H), 8.61 (d, J = 5.6 Hz, 1H), 8.03 (d, J = 1.7 Hz, 1H), 7.85-7.81 (m, 2H), 7.57 (s, 1H), 7.54-7.50 (m, 3H), 6.95 (d, J = 2.6 Hz, 1H), 4.28 (s, 2H). | m/z 365.2 (M + H)+ (ES+), at 5.41 min, 99% (Method 2) |
| 30 | 1-(4-(3-fluoro-5-(trifluoromethyl)benzyl) pyridin-2-yl)-5-methyl-1H-pyrazole-3-carboxamide | Intermediate 9 and CAS: 12125-02-9 Procedure 9 | (400 MHz, DMSO-$d_6$) δ: 8.43 (d, J = 5.2 Hz, 1H), 7.94 (s, 1H), 7.56 (d, J = 8.8 Hz, 2H), 7.66 (s, 2H), 7.38-7.32 (m, 2H), 6.64 (s, 1H), 4.21 (s, 2H), 2.58 (s, 3H). | m/z 379.2 (M + H)+ (ES+), at 1.72 min, 99% (Method 10) |
| 31 | 1-(4-(3-fluoro-5-(trifluoromethyl)benzyl) pyridin-2-yl)-N-methyl-1H-pyrazole-3-carboxamide | Intermediate 5 and CAS: 593-51-1 Procedure 8 | (400 MHz, DMSO-$d_6$) δ: 8.64 (d, J = 2.6 Hz, 1H), 8.43 (d, J = 5.1 Hz, 1H), 8.34 (d, J = 5.1 Hz, 1H), 8.00 (s, 1H), 7.67-7.50 (m, 3H), 7.33 (d, J = 5.1 Hz, 1H), 6.88 (d, J = 2.6 Hz, 1H), 4.24 (s, 2H), 2.80 (d, J = 4.7 Hz, 3H). | m/z 379.1 (M + H)+ (ES+), at 6.33 min, 100% (Method 5) |
| 32 | 1-(4-(3-fluoro-5-(trifluoromethyl)benzyl) pyridin-2-yl)-N,N-dimethyl-1H-pyrazole-3-carboxamide | Intermediate 5 and CAS: 124-40-3 Procedure 8 | (400 MHz, DMSO-$d_6$) δ: 8.62 (d, J = 2.6 Hz, 1H), 8.42 (d, J = 5.1 Hz, 1H), 7.87 (s, 1H), 7.66 (s, 1H), 7.58 (t, J = 9.9 Hz, 2H), 7.33 (dd, J = 5.1, 1.5 Hz, 1H), 6.79 (d, J = 2.6 Hz, 1H), 4.24 (s, 2H), 3.25 (s, 3H), 3.02 (s, 3H). | m/z 393.2 (M + H)+ (ES+), at 6.19 min, 99% (Method 2) |
| 33 | (1-(4-(3-fluoro-5-(trifluoromethyl)benzyl) pyridin-2-yl)-1H-pyrazol-3-yl)(pyrrolidin-1-yl)methanone | Intermediate 5 and CAS: 123-75-1 Procedure 8 | (400 MHz, DMSO-$d_6$) δ: 8.61 (d, J = 2.7 Hz, 1H), 8.42 (d, J = 5.1 Hz, 1H), 7.83 (s, 1H), 7.67 (s, 1H), 7.59 (d, J = 9.3 Hz, 2H), 7.34 (dd, J = 5.1, 1.5 Hz, 1H), 6.86 (d, J = 2.5 Hz, 1H), 4.26 (s, 2H), 3.85 (t, J = 6.7 Hz, 2H), 3.51 (t, J = 6.8 Hz, 2H), 1.89 (dq, J = 23.0, 6.8 Hz, 4H). | m/z 419.2 (M + H)+ (ES+), at 6.49 min, 100% (Method 2) |
| 34 | 1-(4-(3-fluoro-5-(trifluoromethyl)benzyl) pyridin-2-yl)-N-(oxetan-3-yl)-1H-pyrazole-3-carboxamide | Intermediate 5 and CAS: 21635-88-1 Procedure 8 | (400 MHz, DMSO-$d_6$) δ: 9.07 (d, J = 6.8 Hz, 1H), 8.66 (d, J = 2.6 Hz, 1H), 8.44 (d, J = 5.0 Hz, 1H), 8.05 (s, 1H), 7.62 (s, 1H), 7.57 (t, J = 10.6 Hz, 2H), 7.32 (dd, J = 5.2, 1.5 Hz, 1H), 6.93 (d, J = 2.6 Hz, 1H), 5.04 (h, J = 7.1 Hz, 1H), 4.77 (t, J = 6.9 Hz, 2H), 4.65 (t, J = 6.4 Hz, 2H), 4.26 (s, 2H). | m/z 421.2 (M + H)+ (ES+), at 5.99 min, 100% (Method 2) |
| 35 | 1-(4-(3-fluoro-5-(trifluoromethyl)benzyl) pyridin-2-yl)-N-(2-hydroxyethyl)-1H-pyrazole-3-carboxamide | Intermediate 5 and CAS: 141-43-5 Procedure 9 | (400 MHz, DMSO-$d_6$) δ: 8.65 (d, J = 2.7 Hz, 1H), 8.43 (d, J = 5.1 Hz, 1H), 8.24 (t, J = 5.8 Hz, 1H), 8.02 (s, 1H), 7.61 (s, 1H), 7.60-7.49 (m, 2H), 7.32 (dd, J = 5.1, 1.5 Hz, 1H), 6.91 (d, J = 2.6 Hz, 1H), 4.78 (t, J = 5.5 Hz, 1H), 4.25 (s, 2H), 3.52 (q, J = 6.0 Hz, 2H), 3.36 (t, J = 6.1 Hz, 2H). | m/z 409.2 (M + H)+ (ES+), at 5.66 min, 98% (Method 2) |
| 36 | 1-(4-(3-fluoro-5-(trifluoromethyl)benzyl) pyridin-2-yl)-N-(2-methoxyethyl)-1H-pyrazole-3-carboxamide | Intermediate 5 and CAS: 109-85-3 Procedure 8 | (400 MHz, DMSO-$d_6$) δ: 8.65 (d, J = 2.7 Hz, 1H), 8.43 (d, J = 5.0 Hz, 1H), 8.30 (t, J = 5.4 Hz, 1H), 8.01 (s, 1H), 7.61 (s, 1H), 7.60-7.49 (m, 2H), 7.32 (dd, J = 5.1, 1.5 Hz, 1H), 6.91 (d, J = 2.6 Hz, 1H), 4.25 (s, 2H), 3.52-3.40 (m, 4H), 3.28 (s, 3H). | m/z 423.2 (M + H)+ (ES+), at 6.20 min, 99% (Method 2) |
| 37 | 1-(4-(3-(difluoromethyl)-5-fluorobenzyl) pyridin-2-yl)-3-methyl-1H-pyrazole-4-carboxamide | Intermediate 15 and CAS: 12125-02-9 Procedure 11 | (400 MHz, DMSO-$d_6$) δ: 8.45 (d, J = 4.8 Hz, 1H), 8.12 (s, 1H), 7.74 (s, 1H), 7.62 (s, 1H), 7.45-7.42 (m, 4H), 7.32 (d, J = 8.8 Hz, 1H), 7.03 (t, J = 55.6 Hz, 1H), 4.19 (s, 2H), 2.78 (s, 3H). | m/z 360.9 (M + H)+ (ES+), at 2.38 min, 99% (Method 11) |
| 38 | 1-(4-(3-(difluoromethyl)-5-fluorobenzyl)pyridin-2-yl)-1H-pyrazole-3-carboxamide | Intermediate 16 and CAS: 12125-02-9 Procedure 11 | (400 MHz, DMSO-$d_6$) δ: 8.64 (d, J = 1.8 Hz, 1H), 8.43 (d, J = 3.9 Hz, 1H), 8.02 (d, J = 0.6 Hz, 1H), 7.80 (s, 1H), 7.50 (s, 1H), 7.43-7.32 (m, 4H), 7.03 (t, J = 55.8 Hz, 1H), 6.95 (d, J = 2.4 Hz, 1H), 4.20 (s, 2H). | m/z 347.0 (M + H)+ (ES+), at 2.47 min, 99% (Method 11) |
| 39 | 1-(4-(3-fluoro-5-(trifluoromethyl)benzyl) pyridin-2-yl)-5-(hydroxymethyl)-3-methyl-1H-pyrazole-4-carboxamide | Intermediate 17 and CAS: 12125-02-9 Procedure 11; or: Intermediates 3 and 11 and CAS: 12125-02-9 Procedure 14 | (400 MHz, DMSO-$d_6$) δ: 8.44 (d, J = 6.8 Hz, 1H), 7.80 (s, 1H), 7.66-7.55 (m, 4H), 7.42-7.37 (m, 2H), 5.63 (t, J = 8.4 Hz, 1H), 4.91 (d, J = 8.4 Hz, 2H), 4.23 (s, 2H), 2.36 (s, 3H). | m/z 409.0 (M + H)+ (ES+), at 2.08 min, 97% (Method 1) |
| 40 | 1-(4-(3-fluoro-5-(trifluoromethyl)benzyl) pyridin-2-yl)-N-(2-hydroxyethyl)-5-(hydroxymethyl)-3-methyl-1H-pyrazole-4-carboxamide | Intermediate 17 and CAS: 141-43-5 Procedure 12 | (400 MHz, DMSO-$d_6$) δ: 8.44 (d, J = 5.2 Hz, 1H), 8.08 (t, J = 5.6 Hz, 1H), 7.81 (s, 1H), 7.67 (s, 1H), 7.62-7.58 (m, 2H), 7.39 (d, J = 1.2 Hz, 1H), 5.62 (t, J = 6.4 Hz, 1H), 4.89 (d, J = 6.4 Hz, 2H), 4.74 (t, J = 5.6 Hz, 1H), 4.24 (s, 2H), 3.53-3.52 (m, 2H), 3.34-3.30 (m, 2H), 2.34 (s, 3H). | m/z 453.0 (M + H)+ (ES+), at 2.08 min, 95% (Method 13) |
| 41 | 1-(2-(3-fluoro-5-(trifluoromethyl)benzyl) pyridin-4-yl)-5-(hydroxymethyl)-3-methyl-1H-pyrazole-4-carboxamide | Intermediate 18 and CAS: 12125-02-9 Procedure 11 | (400 MHz, DMSO-$d_6$) δ: 8.64 (dd, J = 5.4, 1.6 Hz, 1H), 7.74 (s, 1H), 7.63-7.61 (m, 2H), 7.55-7.53 (m, 2H), 7.45 (s, 1H), 7.39 (s, 1H), 5.89 (t, J = 3.6 Hz, 1H), 4.65 (d, J = 5.2 Hz, 2H), 4.31 (s, 2H), 2.37 (s, 3H). | m/z 409.0 (M + H)+ (ES+), at 1.77 min, 96% (Method 11) |
| 42 | 1-(2-(3-fluoro-5-(trifluoromethyl)benzyl) yridin-4-yl)-N-(2-phydroxyethyl)-5- | Intermediate 18 and CAS: 141-43-5 Procedure 11 | (400 MHz, DMSO-$d_6$) δ: 8.63 (d, J = 5.6 Hz, 1H), 7.94 (t, J = 5.2 Hz, 1H), 7.74 (s, 1H), 7.64-7.63 (m, 2H), 7.55-7.53 (m, 2H), 5.87 (t, J = 4.4 Hz, 1H), 4.75 (t, J = 4.4 Hz, 1H), 4.63 (d, J = 5.2 Hz, | m/z 453.0 (M + H)+ (ES+), at 1.99 min, 99% (Method 11) |

TABLE 3-continued

| Ex. No. | Name | Intermediate/ procedure | $^1$H NMR | LCMS |
|---|---|---|---|---|
| Examples table | | | | |
| | (hydroxymethyl)-3-methyl-1H-pyrazole-4-carboxamide | | 2H), 4.31 (s, 2H), 3.52 (q, J = 5.6 Hz, 2H), 3.37-3.33 (m, 2H), 2.35 (s, 3H). | |
| 43 | 1-(4-(3-fluoro-5-(trifluoromethyl)benzyl)pyridin-2-yl)-5-(hydroxymethyl)-N,3-dimethyl-1H-pyrazole-4-carboxamide | Intermediate 17 and CAS: 74-89-5 Procedure 11 | (400 MHz, DMSO-$d_6$) δ: 8.44 (d, J = 4.8 Hz, 1H), 7.97 (d, J = 4.8 Hz, 1H), 7.81 (s, 1H), 7.67-7.56 (m, 3H), 7.38 (d, J = 5.2 Hz, 1H), 5.58 (t, J = 6.4 Hz, 1H), 4.87 (d, J = 6.4 Hz, 2H), 4.24 (s, 2H), 2.78 (d, J = 4.8 Hz, 3H), 2.34 (s, 3H). | m/z 422.9 (M + H)+ (ES+), at 2.29 min, 99% (Method 11) |
| 44 | 1-(4-(3-(difluoromethyl)-5-fluorobenzyl)pyridin-2-yl)-5-(hydroxymethyl)-3-methyl-1H-pyrazole-4-carboxamide | Intermediate 19 and CAS: 12125-02-9 Procedure 11 | (400 MHz, DMSO-$d_6$) δ: 8.44 (d, J = 5.2 Hz, 1H), 7.78 (s, 1H), 7.53-7.50 (m, 1H), 7.46-7.43 (m, 3H), 7.37-7.31 (m, 2H), 7.03 (t, J = 55.2 Hz, 1H), 5.64 (t, J = 6.4 Hz, 1H), 4.91 (d, J = 6.4 Hz, 2H), 4.20 (s, 2H), 2.37 (s, 3H). | m/z 391.0 (M + H)+ (ES+), at 1.88 min, 97% (Method 1) |
| 45 | 1-(4-(3-(difluoromethyl)-5-fluorobenzyl)pyridin-2-yl)-N,3-dimethyl-1H-pyrazole-4-carboxamide | Intermediate 15 and CAS: 74-89-5 Procedure 11 | (400 MHz, DMSO-$d_6$) δ: 8.45 (d, J = 5.2 Hz, 1H), 8.09 (s, 2H), 7.74 (s, 1H), 7.45-7.31 (m, 4H), 7.03 (t, J = 55.6 Hz, 1H), 4.19 (s, 2H), 2.78 (s, 3H), 2.74 (d, J = 4.6 Hz, 3H). | m/z 374.9 (M + H)+ (ES+), at 2.45 min, 99% (Method 11) |
| 46 | 1-(4-(3-(difluoromethyl)-5-fluorobenzyl)pyridin-2-yl)-N-methyl-1H-pyrazole-3-carboxamide | Intermediate 16 and CAS: 74-89-5 Procedure 11 | (400 MHz, DMSO-$d_6$) δ: 8.66 (d, J = 2.8 Hz, 1H), 8.44 (d, J = 4.8 Hz, 1H), 8.35-8.34 (m, 1H), 7.99 (s, 1H), 7.44-7.37 (m, 2H), 7.33-7.32 (m, 2H), 7.17 (t, J = 58.0 Hz, 1H), 6.89 (s, 1H), 4.23 (s, 2H), 2.80 (d, J = 4.0 Hz, 3H). | m/z 361.0 (M + H)+ (ES+), at 2.56 min, 93% (Method 11) |
| 47 | 1-(6-(3-fluoro-5-(trifluoromethyl)benzyl) pyridin-2-yl)-3-(hydroxymethyl)-1H-pyrazole-4-carboxamide | Intermediate 20 and CAS: 12125-02-9 Procedure 13 | (400 MHz, DMSO-$d_6$) δ: 9.15 (s, 1H), 8.12 (s, 1H), 7.97 (t, J = 8.0 Hz, 1H), 7.78 (d, J = 8.0 Hz, 1H), 7.63-7.55 (m, 3H), 7.49 (s, 1H), 7.33 (d, J = 7.2 Hz, 1H), 5.77 (m, 1H), 4.66 (d, J = 4.4 Hz, 2H), 4.29 (s, 2H). | m/z 394.9 (M + H)+ (ES+), at 2.18 min, 98% (Method 1) |
| 48 | 1-(6-(3-fluoro-5-(trifluoromethyl)benzyl) pyridin-2-yl)-3-(hydroxymethyl)-N-methyl-1H-pyrazole-4-carboxamide | Intermediate 20 and CAS: 74-89-5 Procedure 13 | (400 MHz, DMSO-$d_6$) δ: 9.11 (s, 1H), 8.59 (s, 1H), 7.97 (t, J = 8.4 Hz, 1H), 7.79 (d, J = 8.4 Hz, 1H), 7.63-7.56 (m, 3H), 7.33 (d, J = 7.6 Hz, 1H), 5.75 (t, J = 6.0 Hz, 1H), 4.67 (d, J = 6.0 Hz, 2H), 4.30 (s, 2H), 2.79 (d, J = 3.2 Hz, 3H). | m/z 409.0 (M + H)+ (ES+), at 2.27 min, 98% (Method 1) |
| 49 | 1-(4-(3-fluoro-5-(trifluoromethyl)benzyl) pyridin-2-yl)-4-(hydroxymethyl)-1H-pyrazole-3-carboxamide | Intermediate 21 and CAS: 12125-02-9 Procedure 11 | (400 MHz, DMSO-d6) δ: 8.51 (s, 1H), 8.42 (d, J = 5.2 Hz, 1H), 8.04 (s, 1H), 7.83 (s, 1H), 7.61-7.55 (m, 4H), 7.32 (d, J = 4.8 Hz, 1H), 5.27 (t, J = 6.0 Hz, 1H), 4.64 (d, J = 6.0 Hz, 2H), 4.23 (s, 2H). | m/z 395.0 (M + H)+ (ES+), at 2.06 min, 99% (Method 1) |
| 50 | 1-(4-(3-fluoro-5-(trifluoromethyl)benzyl) pyridin-2-yl)-4-(hydroxymethyl)-N-methyl-1H-pyrazole-3-carboxamide | Intermediate 21 and CAS: 74-89-5 Procedure 11 | (400 MHz, DMSO-$d_6$) δ: 8.52 (s, 1H), 8.44-8.39 (m, 2H), 8.01 (s, 1H), 7.60-7.53 (m, 3H), 7.31 (d, J = 5.2 Hz, 1H), 5.26 (t, J = 5.6 Hz, 1H), 4.65 (d, J = 6.0 Hz, 2H), 4.24 (s, 2H), 2.81 (s, 3H). | m/z 409.1 (M + H)+ (ES+), at 2.34 min, 100% (Method 11) |
| 51 | 1-(6-(3-fluoro-5-(trifluoromethyl)benzyl) pyridin-2-yl)-4-(hydroxymethyl)-1H-pyrazole-3-carboxamide | Intermediate 22 and CAS: 12125-02-9 Procedure 11 | (400 MHz, DMSO-$d_6$) δ: 8.49 (s, 1H), 8.00 (t, J = 8.0 Hz, 1H), 7.91 (d, J = 8.0 Hz, 1H), 7.85 (s, 1H), 7.64 (s, 1H), 7.60-7.54 (m, 3H), 7.37 (d, J = 7.2 Hz, 1H), 5.26 (t, J = 6.0 Hz, 1H), 4.65 (d, J = 5.2 Hz, 2H), 4.29 (s, 2H). | m/z 394.9 (M + H)+ (ES+), at 2.57 min, 98% (Method 11) |
| 52 | 1-(2-(3-fluoro-5-(trifluoromethyl)benzyl)-5-methylpyridin-4-yl)-3-methyl-1H-pyrazole-4-carboxamide | Intermediate 23 and CAS: 12125-02-9 Procedure 11 | (400 MHz, DMSO-$d_6$) δ: 8.60 (s, 1H), 8.15 (s, 1H), 7.63 (s, 1H), 7.58-7.52 (m, 3H), 7.47 (s, 1H), 7.11 (s, 1H), 4.26 (s, 2H), 2.33 (s, 3H), 2.02 (s, 3H). | m/z 393.0 (M + H)+ (ES+), at 2.22 min, 95% (Method 11) |
| 53 | 1-(4-(3-fluoro-5-(trifluoromethyl)benzyl) pyridin-2-yl)-3-(hydroxymethyl)-5-methyl-1H-pyrazole-4-carboxamide | Intermediates 3 and 11 and CAS: 12125-02-9 Procedure 14 | (400 MHz, DMSO-$d_6$) δ: 8.44 (d, J = 6.4 Hz, 1H), 7.88 (s, 1H), 7.74 (s, 1H), 7.65-7.56 (m, 3H), 7.39-7.36 (m, 2H), 5.99 (t, J = 7.2 Hz, 1H), 4.58 (d, J = 7.2 Hz, 2H), 4.23 (s, 2H), 2.72 (s, 3H). | m/z 409.0 (M + H)+ (ES+), at 2.00 min, 99% (Method 1) |
| 54 | 1-(4-(3-fluoro-5-(trifluoromethyl)benzyl) pyridin-2-yl)-5-(hydroxymethyl)-1H-pyrazole-3-carboxamide | Intermediate 24 and CAS: 12125-02-9 Procedure 11 | (400 MHz, DMSO-$d_6$) δ: 8.43 (d, J = 4.8 Hz, 1H), 8.02 (s, 1H), 7.74 (s, 1H), 7.64 (s, 1H), 7.58 (d, J = 9.2 Hz, 2H), 7.45 (s, 1H), 7.34 (d, J = 5.2 Hz, 1H), 6.83 (s, 1H), 5.49 (t, J = 6.0 Hz, 1H), 4.89 (d, J = 6.0 Hz, 2H), 4.23 (s, 2H). | m/z 395.0 (M + H)+ (ES+), at 2.20 min, 100% (Method 11) |
| 55 | 1-(2-(3-fluoro-5-(trifluoromethyl)benzyl) pyridin-4-yl)-N-methyl-1H-pyrazole-3-carboxamide | Intermediate 2 and CAS: 15366-34-4 and 74-89-5 Procedure 10 (using MeOH in step 2, part i) | (400 MHz, $CDCl_3$) δ: 8.64 (dd, J = 5.5, 0.7 Hz, 1H), 8.01 (d, J = 2.6 Hz, 1H), 7.56 (dd, J = 2.2, 0.6 Hz, 1H), 7.49 (dd, J = 5.6, 2.2 Hz, 1H), 7.37 (tq, J = 1.4, 0.7 Hz, 1H), 7.21 (ddq, J = 9.1, 1.3, 0.6 Hz, 2H), 7.04 (d, J = 2.6 Hz, 1H), 6.96 (s, 1H), 4.26 (s, 2H), 3.03 (d, J = 5.0 Hz, 3H). | m/z 379.4 (M + H)+ (ES+), at 1.64 min, 100% (Method 10) |
| 56 | 2-(4-(3-fluoro-5-(trifluoromethyl)benzyl) pyridin-2-yl)-N-methyl-2H- | Intermediate 1 and CAS: 1084802-21-0 and 74-89-5 | (400 MHz, $CDCl_3$) δ: 8.56 (dd, J = 5.1, 0.7 Hz, 1H), 8.32 (s, 1H), 7.96 (dq, J = 1.4, 0.7 Hz, 1H), 7.29 (tt, J = 1.6, 0.7 Hz, 1H), 7.26 (dd, J = 5.7, | m/z 380.3 (M + H)+ (ES+), at 1.64 min, 100% (Method 10) |

TABLE 3-continued

| Ex. No. | Name | Intermediate/ procedure | $^1$H NMR | LCMS |
|---|---|---|---|---|
| Examples table | | | | |
| | 1,2,3-triazole-4-carboxamide | Procedure 10 (using MeOH in step 2, part i) | 1.4 Hz, 1H), 7.19 (ddt, J = 5.0, 1.3, 0.6 Hz, 1H), 7.10 (dt, J = 9.0, 1.8 Hz, 1H), 7.01 (s, 1H), 4.15 (s, 2H), 3.02 (d, J = 5.0 Hz, 3H). | |
| 57 | 1-(4-(3-fluoro-5-(trifluoromethyl)benzyl) pyridin-2-yl)-/,4-dimethyl-1H-pyrazole-3-carboxamide | Intermediate 1 and CAS: 6076-12-6 and 74-89-5 Procedure 10 (using MeOH in step 2, part i) | (400 MHz, $CDCl_3$) δ: 8.34 (dd, J = 5.1, 0.7 Hz, 1H), 8.33 (q, J = 0.9 Hz, 1H), 7.78 (dq, J = 1.5, 0.7 Hz, 1H), 7.29 (tq, J = 1.4, 0.7 Hz, 1H), 7.26-7.21 (m, 1H), 7.12-7.06 (m, 1H), 7.00 (ddd, J = 5.0, 1.3, 0.7 Hz, 1H), 6.96 (d, J = 4.0 Hz, 1H), 4.09 (s, 2H), 3.00 (d, J = 5.0 Hz, 3H), 2.41 (d, J = 1.0 Hz, 3H). | m/z 393.2 (M + H)+ (ES+), at 4.54 min, 100% (Method 9) |
| 58 | 2-(4-(3-fluoro-5-(trifluoromethyl)benzyl) pyridin-2-yl)-N,5-dimethyl-2H-1,2,3-triazole-4-carboxamide | Intermediate 1 and CAS: 60419-70-7 and 74-89-5 Procedure 10 (using MeOH in step 2,part i) | (400 MHz, $CDCl_3$) δ: 8.54 (dd, J = 5.0, 0.7 Hz, 1H), 7.91 (dq, J = 1.4, 0.7 Hz, 1H), 7.29 (dq, J = 1.6, 0.8 Hz, 1H), 7.28-7.23 (m, 1H), 7.14 (ddd, J = 5.1, 1.4, 0.7 Hz, 1H), 7.13-7.06 (m, 1H), 7.00 (s, 1H), 4.14 (s, 2H), 3.00 (d, J = 5.0 Hz, 3H), 2.68 (s, 3H). | m/z 394.3 (M + H)+ (ES+), at 1.69 min, 97% (Method 10) |
| 59 | 1-(2-((3-fluoro-5-(trifluoromethyl)phenyl) (hydroxy)methyl)pyridin-4-yl)-3-methyl-1H-pyrazole-4-carboxamide | Intermediate 2 and CAS: 85290-78-4 and 12125-02-9 Procedure 15 | (400 MHz, DMSO-$d_6$) δ: 9.10 (d, J = 0.6 Hz, 1H), 8.57 (dd, J = 5.5, 0.6 Hz, 1H), 8.01 (dt, J = 2.3, 0.6 Hz, 1H), 7.67 (tt, J = 1.5, 0.7 Hz, 1H), 7.63-7.60 (m, 1H), 7.60-7.53 (m, 2H), 7.51 (s, 1H), 7.18 (s, 1H), 6.68 (s, 1H), 5.91 (s, 1H), 2.44 (s, 3H). | m/z 395.2 (M + H)+ (ES+), at 1.21 min, 100% (Method 8) |

Biological Activity

GPR52 Agonist Functional cAMP Assay

HEKf suspension cells were infected for 24 h with 0.1% v/v human GPR52 expressing BacMam virus, a modified baculovirus designed for mammalian gene expression. Following BacMam infection, cells were pelleted by centrifugation (335 g, 5 min), resuspended in cell freezing medium (Sigma) and frozen at −150° C. until required. On experiment day, 25 nL GPR52 compound dilutions, prepared in DMSO, were stamped onto proxiplates (PerkinElmer) by a LabCyte ECHO acoustic dispenser. Frozen cells were thawed and resuspended in assay stimulation buffer (Cisbio) containing 0.5 mM 3-iso-butyl-1-methylxanthine (IBMX, Sigma) to achieve a density of 2000 cells per well. 10 μl cells were added to assay plates using a Multidrop Combi Reagent Dispenser (ThermoFisher) before centrifugation (335 g, 1 min). Cells were incubated with compounds at 37° C. for 30 min prior to addition of cAMP detection reagents (HiRange cAMP kit, Cisbio) which were prepared according to the manufacturer's instructions. Plates were shaken for 1 h at room temperature before reading on a PHERAstar FS plate reader (BMG Labtech) using standard HTRF settings. HTRF ratios were obtained by dividing the acceptor emissions (665 nm) by the donor emissions (620 nm) and multiplying by 10,000. Data were normalised to DMSO (0%) and maximal 3-(2-(3-chloro-5-fluorobenzyl)benzo[b]thiophen-7-yl)-N-(2-methoxyethyl)benzamide (compound 7m in J. Med. Chem., 2014, 57, 5226) responses (100%) and fit to a 4-parameter logistical fit to generate agonist $pEC_{50}$s and maximal responses which are presented in Table 4 below.

TABLE 4

| Ex. No. | $pEC_{50}$ average | $E_{max}$ (%) |
|---|---|---|
| GPR52 $pEC_{50}$ data | | |
| 1 | 6.9 | 90 |
| 2 | 6.3 | 90 |
| 3 | 6.5 | 86 |

TABLE 4-continued

| Ex. No. | $pEC_{50}$ average | $E_{max}$ (%) |
|---|---|---|
| GPR52 $pEC_{50}$ data | | |
| 4 | 6.5 | 84 |
| 5 | 7.8 | 94 |
| 6 | 7.9 | 97 |
| 7 | 6.9 | 93 |
| 8 | 7.7 | 96 |
| 9 | 7.0 | 85 |
| 10 | 7.1 | 83 |
| 11 | 6.6 | 86 |
| 12 | 7.3 | 95 |
| 13 | 7.4 | 93 |
| 14 | 7.5 | 95 |
| 15 | 7.1 | 92 |
| 16 | 7.5 | 93 |
| 17 | 8.0 | 93 |
| 18 | 7.1 | 92 |
| 19 | 7.8 | 99 |
| 20 | 7.8 | 96 |
| 21 | 7.4 | 96 |
| 22 | 7.8 | 96 |
| 23 | 7.6 | 87 |
| 24 | 7.6 | 91 |
| 25 | 8.0 | 99 |
| 26 | 7.0 | 87 |
| 27 | 7.6 | 97 |
| 28 | 7.5 | 95 |
| 29 | 5.9 | 86 |
| 30 | 6.8 | 93 |
| 31 | 7.7 | 87 |
| 32 | 6.7 | 75 |
| 33 | 6.9 | 87 |
| 34 | 6.2 | 77 |
| 35 | 6.4 | 83 |
| 36 | 6.9 | 87 |
| 37 | 7.1 | 96 |
| 38 | 7.7 | 93 |
| 39 | 8.2 | 101 |
| 40 | 8.6 | 101 |
| 41 | 7.5 | 98 |
| 42 | 7.5 | 100 |
| 43 | 8.0 | 101 |
| 44 | 8.4 | 101 |
| 45 | 6.7 | 91 |

TABLE 4-continued

| GPR52 $pEC_{50}$ data | | |
|---|---|---|
| Ex. No. | $pEC_{50}$ average | $E_{max}$ (%) |
| 46 | 7.3 | 88 |
| 47 | 6.3 | 52 |
| 48 | 5.8 | 36 |
| 49 | 7.2 | 93 |
| 50 | 8.0 | 82 |
| 51 | 6.3 | 83 |
| 52 | 7.0 | 100 |
| 53 | 7.1 | 97 |
| 54 | 7.1 | 92 |
| 55 | 6.9 | 83 |
| 56 | 7.0 | 84 |
| 57 | 8.5 | 87 |
| 58 | 7.8 | 92 |
| 59 | 6.7 | 79 |

Pharmacokinetic Profiling

The pharmacokinetic profiles of Example 39 were assessed in male Sprague-Dawley rats via intravenous (IV) and oral (per os, PO) routes of delivery. Pharmacokinetic data (mean values ±standard deviation) for Example 39 of the invention are detailed in Table 5.

Methods: For pharmacokinetic analysis, groups of three male Sprague-Dawley rats, ranging in weight between 200 and 230 g, were administered a single dose of Example 39 via IV or PO route, using the doses, dose volumes and vehicles specified in Table 5. Following dosing, blood samples were taken at several time points (pre-dose, 2 min, 5 min, 15 min, 30 min, 1 h, 3 h, 6 h, 12 h and 24 h for IV administration and pre-dose, 5 min, 15 min, 30 min, 1 hr, 2 h, 4 h, 8 h, 12 h and 24 h for PO administration) via serial tail vein bleeds, and centrifuged to separate plasma for analysis by LC-MS/MS. WinNonlin v8.2 statistics software (Pharsight Corporation, California, USA) was used to generate pharmacokinetic parameters using non-compartmental analysis.

Brain Penetration

Plasma and brain exposure were evaluated to assess the brain penetration of Example 39, following IV administration. Unbound brain-to-plasma ratio ($K_{p,uu}$) was calculated, as detailed in Table 5, following experimental determination of binding in rat plasma and brain homogenate.

Methods: For brain penetration assessment, male Sprague-Dawley rats (n=3) were administered a single 1 mg/kg dose (formulated in 10% DMAC+10% Solutol HS15+80% saline) via the IV route. After 10 min post-dose, animals were sacrificed and brains extracted, homogenised with 2 volumes (w/v) of 50 mM sodium phosphate buffer (pH 7.4), and analysed by LC-MS/MS. Blood samples were removed at the same time point via tail vein bleed, centrifuged and the plasma analysed by LC-MS/MS.

To permit calculation of unbound brain-to-plasma ratio ($K_{p,uu}$), test compound binding in rat plasma and brain homogenate was performed, using Rapid Equilibrium Dialysis (RED). Test compound prepared in DMSO (1 μM final, 0.2% DMSO) was added to (i) undiluted male Sprague Dawley rat plasma and (ii) rat brain tissue homogenised with 2 volumes (w/v) of sodium phosphate buffer (pH 7.4), and dialysed against phosphate buffer for 5 h at 37° C. After incubation, the contents of each plasma/brain and buffer compartment were removed and mixed with equal volumes of control dialysed buffer or plasma/brain to maintain matrix similarity for analysis. Proteins were then precipitated by the addition of acetonitrile containing an analytical internal standard (allowing ratio of test compound versus internal standard to be derived), centrifuged and the supernatant removed for analysis by LC-MS/MS. Fraction unbound (F j in plasma and brain was calculated using the following formula, then used to correct total plasma and brain concentrations to derive the $K_{p,uu}$:

$$\text{Fraction bound} = (\text{Total plasma or brain ratio}) - (\text{Total buffer ratio})/\text{Total plasma or brain ratio}$$

$$\text{Fraction unbound } (F_u, \text{ brain or plasma}) = 1 - \text{Fraction bound}$$

For correction of dilution in brain binding assay:

$$\text{Undiluted } F_u, \text{ brain} = (1/\text{dilution factor})/((1/F_u \text{ diluted})) - 1) + (1/\text{dilution factor})$$

Where dilution factor = 4

TABLE 5

| Caffeine-induced locomotor activity in rat | | | | |
|---|---|---|---|---|
| | Rat IV pharmacokinetics (n = 3) | | | |
| | Dose (mg/kg) | Dose volume (mL/kg) | Dosing vehicle | Clearance (mL/min/kg) |
| Example 39 | 1 | 5 | 10% DMAC + 10% Solutol HS15 + 80% saline | 8.8 ± 1.1 |
| | Rat PO pharmacokinetics (n = 3) | | | |
| | Dose (mg/kg) | Dose volume (mL/kg) | Dosing vehicle | Bioavailability (%) |
| Example 39 | 3 | 5 | 10% DMAC + 10% Solutol HS15 + 80% water | 77.4 ± 14.9 |
| | Rat IV brain penetration, 10 min (n = 3) | | | |
| | Dose (mg/kg) | Dose volume (mL/kg) | Dosing vehicle | $K_{p, uu}$ |
| Example 39 | 1 | 5 | 10% DMAC + 10% Solutol HS15 + saline | 0.42 ± 0.08 |

Caffeine, a non-selective adenosine receptor antagonist, is a psychostimulant which increases rodent locomotor activity principally via blockade of $A_{2A}$ receptors (Br. *J. Pharmacol.*, 2000, 129, 1465). These receptors are densely expressed on the terminals of GABAergic striatopallidal neurons in the indirect pathway of the basal ganglia, in which dopamine D2 receptors are co-expressed (*J. Comp. Neurol.*, 1998, 401, 163; *J. Comp. Neurol.*, 2001, 431, 331). Tonic activation of $A_{2A}$ receptors decreases the affinity of D2 receptors to dopamine and antagonism of $A_{2A}$ receptors facilitates dopaminergic signalling (*Curr. Pharm. Des.*, 2008, 14, 1468). A number of antipsychotic agents have been shown to block hyperlocomotion induced by caffeine (*Pharmacol. Biochem. Behav.*, 1994, 47, 89; *Naunyn-Schmiedeberg's Arch. Pharmacol.*, 2016, 389, 11).

Male Sprague-Dawley rats (200-250 g) were housed in groups with a 12 h light/dark cycle (lights on at 07.00), at an ambient temperature of 21±2° C. and with standard pelleted diet and water adlibitum. Testing was carried out in the light phase. On the day of the experiment, animals were habituated to the locomotor cages for a 60-minute period. Subsequently, they were dosed with vehicle or Example 39 (0.1, 0.3, 1 and 3 mg/kg) by the oral route and returned to the appropriate locomotor cage. Example 39 was formulated in a vehicle of 10% DMAC, 10% solutol (Kolliphor HS15) and 80% water (v/v/v). Sixty minutes later, animals were dosed with vehicle (saline) or caffeine (15 mg/kg) by the subcutaneous route. Locomotor activity was assessed for a 2 h period after caffeine treatment. Data are back-transformed means, adjusted for differences between treatment groups in activity during the 30 minutes prior to treatment with test compound or vehicle (n=10-12). Analysis was by general linear model with treatment, cohort and rack as factors. SEMs were calculated from the residuals of the statistical model. Example 39 was compared to caffeine by Williams' test.

As shown in FIG. 1, treatment with Example 39 caused a dose-dependent reduction of the caffeine-induced hyperlocomotor response, reaching statistical significance at 1 and 3 mg/kg.

BRIEF DESCRIPTION OF THE FIGURES

FIG. 1: The effect of acute treatment with Example 39 (0.1, 0.3, 1 and 3 mg/kg, PO) on caffeine-induced hyperlocomotor activity. Significant differences vs caffeine are represented as * $p<0.05$,  $p<0.01$. * $p<0.001$.

The invention claimed is:

1. A compound of Formula (1):

(1)

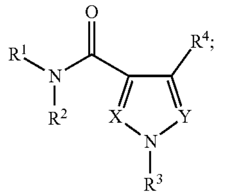

or a pharmaceutically acceptable salt thereof, wherein;

X is N or $CR^5$;

Y is N or $CR^6$;

$R^1$ is H, $C_{1-6}$ alkyl optionally substituted with OH or 1 to 6 fluorine atoms, $C_{3-6}$ cycloalkyl optionally substituted with OH or 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by an O atom which is not directly attached to the N or attached to a carbon atom which is directly attached to the N; or $R^1$ is joined to $R^2$ to form a 4, 5, 6 or 7-membered ring which is optionally substituted with OH or 1 to 6 fluorine atoms;

$R^2$ is H or $C_{1-3}$ alkyl optionally substituted with OH or 1 to 6 fluorine atoms; or $R^2$ is joined to $R^1$ to form a 4, 5, 6 or 7-membered ring which is optionally substituted with OH or 1 to 6 fluorine atoms;

$R^4$, $R^5$ and $R^6$ are independently selected from H, CN, halo, $C_{1-6}$ alkyl optionally substituted with OH or 1 to 6 fluorine atoms, $C_{3-6}$ cycloalkyl optionally substituted with OH or 1 to 6 fluorine atoms and $C_{1-6}$ alkoxy optionally substituted with 1 to 6 fluorine atoms, wherein when the $C_{1-6}$ alkyl or $C_{3-6}$ cycloalkyl group is not substituted with OH, one atom of the $C_{1-6}$ alkyl or $C_{3-6}$ cycloalkyl group may be optionally replaced by O;

$R^3$ is a group of the formula:

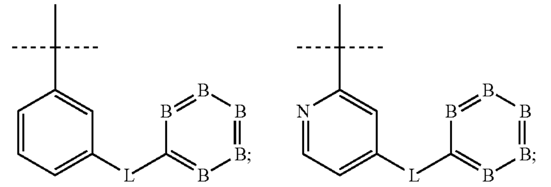

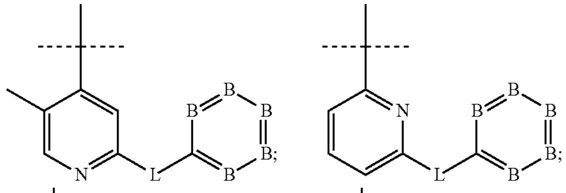

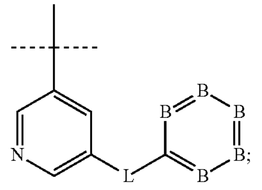

or

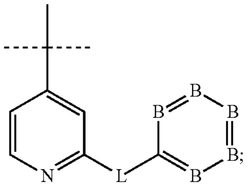

L is $CH_2$ or CHOH; and the group:

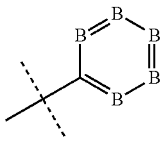

is:

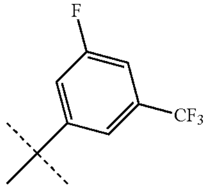

or

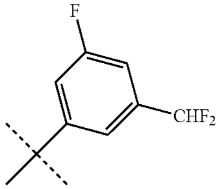

.

2. The compound according to claim 1, wherein $R^1$ is selected from: H, methyl, oxetanyl, $CH_2CH_2OH$ and $CH_2CH_2OCH_3$, or wherein $R^1$ is joined to $R^2$ to form a 5-membered ring.

3. The compound according to claim 1, wherein $R^2$ is H or methyl, or is joined to $R^1$ to form a 5-membered ring.

4. The compound according to claim 1, which is a compound of formula (2a):

(2a)

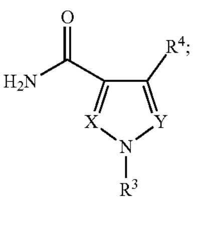

or a salt thereof.

5. The compound according to claim 1, wherein X is N, CH, $CCH_3$ or $CCH_2OH$.

6. The compound according to claim 1, wherein Y is N, CH or $CCH_3$.

7. The compound according to claim 1, wherein $R^4$ is selected from: H, methyl, methoxy, Cl, $CHF_2$, $CF_3$, ethyl, CN, cyclopropyl, $CH_2OH$ and $CH_2OCH_3$.

8. The compound according to claim 1, wherein, $R^5$ and $R^6$ are independently selected from H, methyl and $CH_2OH$.

9. The compound according to claim 1, which is a compound of formula (3a), (3b), (3c) or (3d):

(3a)

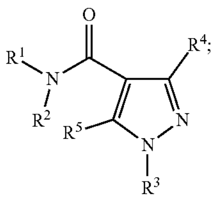

(3b)

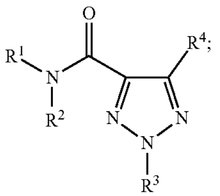

(3c)

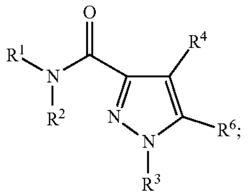

(3d)

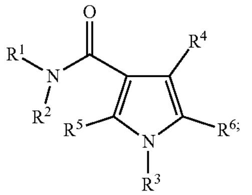

or a pharmaceutically acceptable salt thereof.

10. The compound according to claim 1, wherein $R^3$ is:

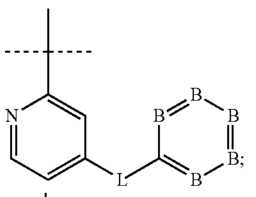

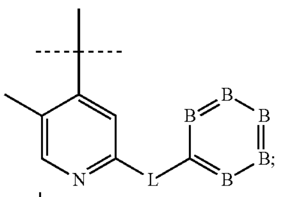

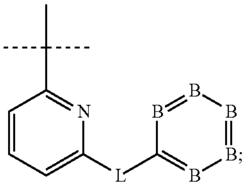

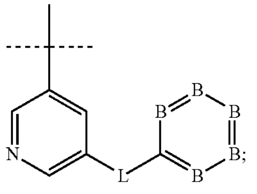

or

-continued

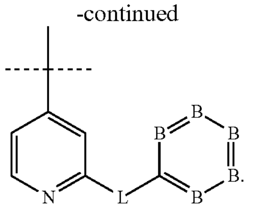

11. The compound according to claim 1, wherein L is $CH_2$.

12. The compound according to claim 1 which is selected from the group consisting of:

1-(4-(3-fluoro-5-(trifluoromethyl)benzyl)pyridin-2-yl)-1H-pyrazole-4-carboxamide;

1-(2-(3-fluoro-5-(trifluoromethyl)benzyl)pyridin-4-yl)-1H-pyrazole-4-carboxamide;

1-(4-(3-fluoro-5-(trifluoromethyl)benzyl)pyridin-2-yl)-N-methyl-1H-pyrazole-4-carboxamide;

2-(4-(3-fluoro-5-(trifluoromethyl)benzyl)pyridin-2-yl)-2H-1,2,3-triazole-4-carboxamide;

1-(4-(3-fluoro-5-(trifluoromethyl)benzyl)pyridin-2-yl)-3-methyl-1H-pyrazole-4-carboxamide;

1-(4-(3-fluoro-5-(trifluoromethyl)benzyl)pyridin-2-yl)-3,5-dimethyl-1H-pyrazole-4-carboxamide;

1-(4-(3-fluoro-5-(trifluoromethyl)benzyl)pyridin-2-yl)-5-methyl-1H-pyrazole-4-carboxamide;

1-(2-(3-fluoro-5-(trifluoromethyl)benzyl)pyridin-4-yl)-3-methyl-1H-pyrazole-4-carboxamide;

1-(4-(3-fluoro-5-(trifluoromethyl)benzyl)pyridin-2-yl)-1H-pyrazole-3-carboxamide;

1-(4-(3-fluoro-5-(trifluoromethyl)benzyl)pyridin-2-yl)-4-methyl-1H-pyrazole-3-carboxamide;

1-(2-(3-fluoro-5-(trifluoromethyl)benzyl)pyridin-4-yl)-3-methoxy-1H-pyrazole-4-carboxamide;

2-(2-(3-fluoro-5-(trifluoromethyl)benzyl)pyridin-4-yl)-5-methyl-2H-1,2,3-triazole-4-carboxamide;

2-(4-(3-fluoro-5-(trifluoromethyl)benzyl)pyridin-2-yl)-5-methyl-2H-1,2,3-triazole-4-carboxamide;

1-(4-(3-fluoro-5-(trifluoromethyl)benzyl)pyridin-2-yl)-3-methoxy-1H-pyrazole-4-carboxamide;

1-(6-(3-fluoro-5-(trifluoromethyl)benzyl)pyridin-2-yl)-4-methyl-1H-pyrazole-3-carboxamide;

(1-(2-(3-fluoro-5-(trifluoromethyl)benzyl)pyridin-4-yl)-3-methyl-1H-pyrazol-4-yl) (pyrrolidin-1-yl) methanone;

1-(2-(3-fluoro-5-(trifluoromethyl)benzyl)pyridin-4-yl)-N,3-dimethyl-1H-pyrazole-4-carboxamide;

1-(2-(3-fluoro-5-(trifluoromethyl)benzyl)pyridin-4-yl)-N,N,3-trimethyl-1H-pyrazole-4-carboxamide;

1-(2-(3-fluoro-5-(trifluoromethyl)benzyl)pyridin-4-yl)-3-methyl-N-(oxetan-3-yl)-1H-pyrazole-4-carboxamide;

1-(2-(3-fluoro-5-(trifluoromethyl)benzyl)pyridin-4-yl)-N-(2-hydroxyethyl)-3-methyl-1H-pyrazole-4-carboxamide;

1-(2-(3-fluoro-5-(trifluoromethyl)benzyl)pyridin-4-yl)-N-(2-methoxyethyl)-3-methyl-1H-pyrazole-4-carboxamide;

3-chloro-1-(2-(3-fluoro-5-(trifluoromethyl)benzyl)pyridin-4-yl)-1H-pyrazole-4-carboxamide;

3-(difluoromethyl)-1-(2-(3-fluoro-5-(trifluoromethyl) benzyl)pyridin-4-yl)-1H-pyrazole-4-carboxamide;

1-(2-(3-fluoro-5-(trifluoromethyl)benzyl)pyridin-4-yl)-3-(trifluoromethyl)-1H-pyrazole-4-carboxamide;

3-ethyl-1-(2-(3-fluoro-5-(trifluoromethyl)benzyl)pyridin-4-yl)-1H-pyrazole-4-carboxamide;

3-cyano-1-(2-(3-fluoro-5-(trifluoromethyl)benzyl)pyridin-4-yl)-1H-pyrazole-4-carboxamide;

3-cyclopropyl-1-(2-(3-fluoro-5-(trifluoromethyl)benzyl) pyridin-4-yl)-1H-pyrazole-4-carboxamide;

1-(4-(3-fluoro-5-(trifluoromethyl)benzyl)pyridin-2-yl)-N,5-dimethyl-1H-pyrazole-3-carboxamide;

1-(2-(3-fluoro-5-(trifluoromethyl)benzyl)pyridin-4-yl)-1H-pyrazole-3-carboxamide;

1-(4-(3-fluoro-5-(trifluoromethyl)benzyl)pyridin-2-yl)-5-methyl-1H-pyrazole-3-carboxamide;

1-(4-(3-fluoro-5-(trifluoromethyl)benzyl)pyridin-2-yl)-N-methyl-1H-pyrazole-3-carboxamide;

1-(4-(3-fluoro-5-(trifluoromethyl)benzyl)pyridin-2-yl)-N,N-dimethyl-1H-pyrazole-3-carboxamide;

(1-(4-(3-fluoro-5-(trifluoromethyl)benzyl)pyridin-2-yl)-1H-pyrazol-3-yl) (pyrrolidin-1-yl) methanone;

1-(4-(3-fluoro-5-(trifluoromethyl)benzyl)pyridin-2-yl)-N-(oxetan-3-yl)-1H-pyrazole-3-carboxamide;

1-(4-(3-fluoro-5-(trifluoromethyl)benzyl)pyridin-2-yl)-N-(2-hydroxyethyl)-1H-pyrazole-3-carboxamide;

1-(4-(3-fluoro-5-(trifluoromethyl)benzyl)pyridin-2-yl)-N-(2-methoxyethyl)-1H-pyrazole-3-carboxamide;

1-(4-(3-(difluoromethyl)-5-fluorobenzyl)pyridin-2-yl)-3-methyl-1H-pyrazole-4-carboxamide;

1-(4-(3-(difluoromethyl)-5-fluorobenzyl)pyridin-2-yl)-1H-pyrazole-3-carboxamide;

1-(4-(3-fluoro-5-(trifluoromethyl)benzyl)pyridin-2-yl)-5-(hydroxymethyl)-3-methyl-1H-pyrazole-4-carboxamide;

1-(4-(3-fluoro-5-(trifluoromethyl)benzyl)pyridin-2-yl)-N-(2-hydroxyethyl)-5-(hydroxymethyl)-3-methyl-1H-pyrazole-4-carboxamide;

1-(2-(3-fluoro-5-(trifluoromethyl)benzyl)pyridin-4-yl)-5-(hydroxymethyl)-3-methyl-1H-pyrazole-4-carboxamide;

1-(2-(3-fluoro-5-(trifluoromethyl)benzyl)pyridin-4-yl)-N-(2-hydroxyethyl)-5-(hydroxymethyl)-3-methyl-1H-pyrazole-4-carboxamide;

1-(4-(3-fluoro-5-(trifluoromethyl)benzyl)pyridin-2-yl)-5-(hydroxymethyl)-N,3-dimethyl-1H-pyrazole-4-carboxamide;

1-(4-(3-(difluoromethyl)-5-fluorobenzyl)pyridin-2-yl)-5-(hydroxymethyl)-3-methyl-1H-pyrazole-4-carboxamide;

1-(4-{[3-(difluoromethyl)-5-fluorophenyl] methyl}pyridin-2-yl)-N,3-dimethyl-1H-pyrazole-4-carboxamide;

1-(4-(3-(difluoromethyl)-5-fluorobenzyl)pyridin-2-yl)-N-methyl-1H-pyrazole-3-carboxamide;

1-(6-(3-fluoro-5-(trifluoromethyl)benzyl)pyridin-2-yl)-3-(hydroxymethyl)-1H-pyrazole-4-carboxamide;

1-(6-(3-fluoro-5-(trifluoromethyl)benzyl)pyridin-2-yl)-3-(hydroxymethyl)-N-methyl-1H-pyrazole-4-carboxamide;

1-(4-(3-fluoro-5-(trifluoromethyl)benzyl)pyridin-2-yl)-4-(hydroxymethyl)-1H-pyrazole-3-carboxamide;

1-(4-(3-fluoro-5-(trifluoromethyl)benzyl)pyridin-2-yl)-4-(hydroxymethyl)-N-methyl-1H-pyrazole-3-carboxamide;

1-(6-(3-fluoro-5-(trifluoromethyl)benzyl)pyridin-2-yl)-4-(hydroxymethyl)-1H-pyrazole-3-carboxamide;

1-(2-(3-fluoro-5-(trifluoromethyl)benzyl)-5-methylpyridin-4-yl)-3-methyl-1H-pyrazole-4-carboxamide;

1-(4-(3-fluoro-5-(trifluoromethyl)benzyl)pyridin-2-yl)-3-(hydroxymethyl)-5-methyl-1H-pyrazole-4-carboxamide;

1-(4-(3-fluoro-5-(trifluoromethyl)benzyl)pyridin-2-yl)-5-(hydroxymethyl)-1H-pyrazole-3-carboxamide;

1-(2-(3-fluoro-5-(trifluoromethyl)benzyl)pyridin-4-yl)-N-methyl-1H-pyrazole-3-carboxamide;

2-(4-(3-fluoro-5-(trifluoromethyl)benzyl)pyridin-2-yl)-N-methyl-2H-1,2,3-triazole-4-carboxamide;

1-(4-(3-fluoro-5-(trifluoromethyl)benzyl)pyridin-2-yl)-N,4-dimethyl-1H-pyrazole-3-carboxamide;

2-(4-(3-fluoro-5-(trifluoromethyl)benzyl)pyridin-2-yl)-N,5-dimethyl-2H-1,2,3-triazole-4-carboxamide;

1-(2-((3-fluoro-5-(trifluoromethyl)phenyl) (hydroxy) methyl) pyridin-4-yl)-3-methyl-1H-pyrazole-4-carboxamide;

or a pharmaceutically acceptable salt thereof.

13. The compound according to claim 1 having GPR52 receptor modulator activity.

14. The compound according to claim 1 for use as a GPR52 receptor agonist.

15. A pharmaceutical composition comprising a compound as defined in claim 1 and a pharmaceutically acceptable excipient.

16. A method of treatment of a disorder or symptom is selected from schizophrenia, positive symptoms of schizophrenia, negative symptoms of schizophrenia, cognitive symptoms of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, anhedonia, agitation, Alzheimer's disease, Parkinson's disease, Huntington's disease, vascular dementia, Lewy body disease, frontotemporal dementia, Tourette's syndrome, hyperprolactinemia, pituitary adenoma, prolactinoma, craniopharyngioma, Cushing's disease, diabetes insipidus, non-functioning tumours, obesity, posttraumatic stress disorder (PTSD), akathisia and associated movements, athetosis, ataxia, ballismus, hemiballismus, chorea, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, tremor, Wilson's disease, schizotypal personality disorder, delusional disorder, brief psychotic disorder, schizophreniform disorder, schizoaffective disorder, substance- or medication-induced psychotic disorder, delusions, hallucinations, disorganized thinking, grossly disorganized or abnormal motor behavior, catatonia, major depressive disorder, bipolar I disorder, bipolar II disorder, cyclothymic disorder, substance- or medication-induced bipolar and related disorders, bipolar and related disorders due to another medical condition, separation anxiety disorder, selective mutism, specific phobia, social anxiety disorder, panic disorder, agoraphobia, generalized anxiety disorder, substance- or medication-induced anxiety disorder, anxiety disorders due to another medical condition, delirium, major neurocognitive disorder, minor neurocognitive disorder, amnesia, dementia, developmental coordination disorder, stereotypic movement disorder, a post-stroke effect, dentatorubral-pallidoluysian atrophy, diminished emotional expression, avolition, alogia and asociality, which comprises administering a therapeutically effective amount of a compound according to claim 1 to a patient in need thereof.

17. The method according to claim 16, wherein the disorder or symptom is selected from schizophrenia, positive symptoms of schizophrenia, negative symptoms of schizophrenia, cognitive symptoms of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, neurocognitive disorder, delirium, anhedonia, agitation, Alzheimer's disease, Parkinson's disease, Huntington's disease, vascular dementia, Lewy body disease, frontotemporal dementia, Tourette's syndrome, hyperprolactinemia, obesity, and posttraumatic stress disorder (PTSD).

18. The compound according to claim 1, wherein said compound is:

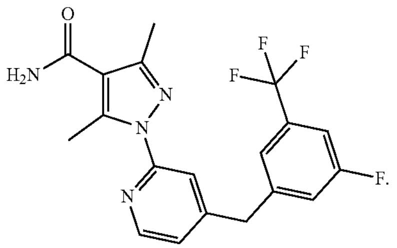 [SMILES: Cc1nn(-c2cc(Cc3cc(F)cc(C(F)(F)F)c3)ccn2)c(C)c1C(N)=O]

19. The compound according to claim 1, wherein said compound is:

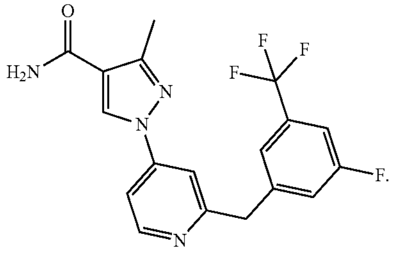 [SMILES: Cc1nn(-c2ccnc(Cc3cc(F)cc(C(F)(F)F)c3)c2)cc1C(N)=O]

20. The compound according to claim 1, wherein said compound is:

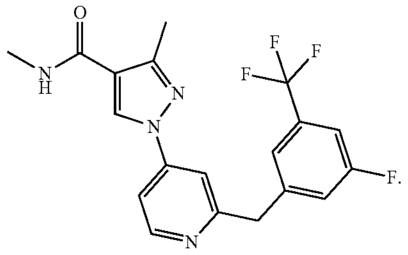 [SMILES: CNC(=O)c1cn(-c2ccnc(Cc3cc(F)cc(C(F)(F)F)c3)c2)nc1C]

21. The compound according to claim 1, wherein said compound is:

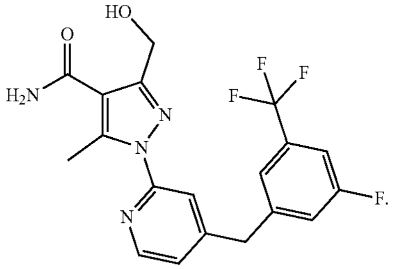 [SMILES: Cc1c(C(N)=O)c(CO)nn1-c1cc(Cc2cc(F)cc(C(F)(F)F)c2)ccn1]

22. The compound according to claim 1, wherein said compound is:

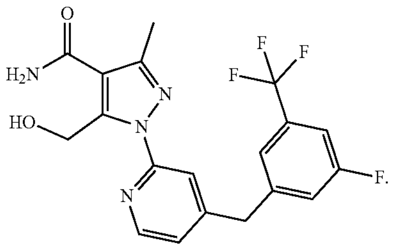 [SMILES: Cc1nn(-c2cc(Cc3cc(F)cc(C(F)(F)F)c3)ccn2)c(CO)c1C(N)=O]

23. The compound according to claim 1, wherein said compound is:

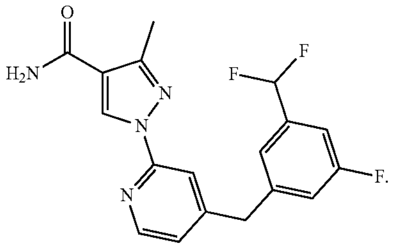 [SMILES: Cc1nn(-c2cc(Cc3cc(F)cc(C(F)F)c3)ccn2)cc1C(N)=O]

24. The compound according to claim 1, wherein said compound is:

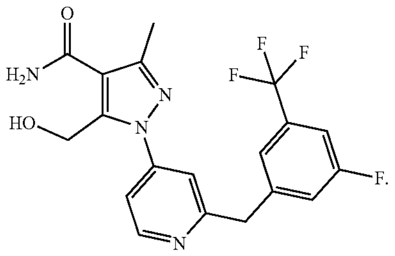 [SMILES: Cc1nn(-c2ccnc(Cc3cc(F)cc(C(F)(F)F)c3)c2)c(CO)c1C(N)=O]

25. The compound according to claim 1, wherein said compound is:

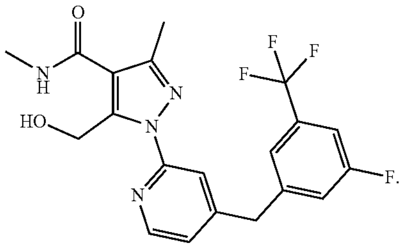 [SMILES: CNC(=O)c1c(C)nn(-c2cc(Cc3cc(F)cc(C(F)(F)F)c3)ccn2)c1CO]

26. The compound according to claim 1, wherein said compound is:

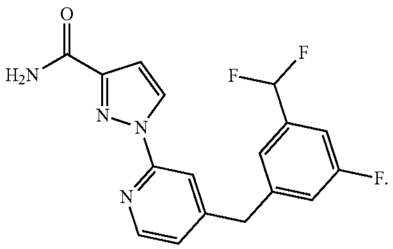 [SMILES: NC(=O)c1ccn(-c2cc(Cc3cc(F)cc(C(F)F)c3)ccn2)n1]

27. The compound according to claim 1, wherein said compound is:

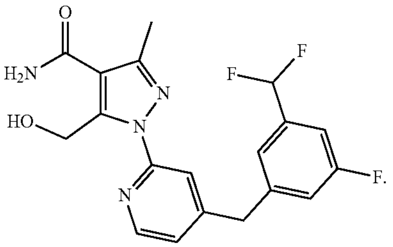 [SMILES: Cc1nn(-c2cc(Cc3cc(F)cc(C(F)F)c3)ccn2)c(CO)c1C(N)=O]

28. A pharmaceutically acceptable salt of the compound as defined in claim 18.

29. A pharmaceutically acceptable salt of the compound as defined in claim 19.

30. A pharmaceutically acceptable salt of the compound as defined in claim 20.

31. A pharmaceutically acceptable salt of the compound as defined in claim 21.

32. A pharmaceutically acceptable salt of the compound as defined in claim 22.

33. A pharmaceutically acceptable salt of the compound as defined in claim 23.

34. A pharmaceutically acceptable salt of the compound as defined in claim 24.

35. A pharmaceutically acceptable salt of the compound as defined in claim 25.

36. A pharmaceutically acceptable salt of the compound as defined in claim 26.

37. A pharmaceutically acceptable salt of the compound as defined in claim 27.

* * * * *